United States Patent
Rajan et al.

(10) Patent No.: US 10,230,783 B2
(45) Date of Patent: Mar. 12, 2019

(54) TELEHEALTH WIRELESS COMMUNICATION HUB DEVICE AND SERVICE PLATFORM SYSTEM

(71) Applicant: QUALCOMM Incorporated, San Diego, CA (US)

(72) Inventors: Rajeev Rajan, San Diego, CA (US); Mark Jerger, San Diego, CA (US); Robert Ganton, San Diego, CA (US); Kumar Senthil, San Diego, CA (US); Jatin Kadakia, San Diego, CA (US); Vishwajeet Lohakarey, San Diego, CA (US); Thien Lee, San Diego, CA (US); Christopher Talbot, San Diego, CA (US); Kabir Suresh Kasargod, San Diego, CA (US); Riddhiman Das, Kansas City, MO (US)

(73) Assignee: QUALCOMM Incorporated, San Diego, CA (US)

( * ) Notice: Subject to any disclaimer, the term of this patent is extended or adjusted under 35 U.S.C. 154(b) by 0 days.

(21) Appl. No.: 14/874,741

(22) Filed: Oct. 5, 2015

(65) Prior Publication Data
US 2016/0029420 A1  Jan. 28, 2016

Related U.S. Application Data

(62) Division of application No. 13/349,938, filed on Jan. 13, 2012.
(Continued)

(51) Int. Cl.
*H04W 76/11* (2018.01)
*H04L 29/08* (2006.01)
(Continued)

(52) U.S. Cl.
CPC ............ *H04L 67/025* (2013.01); *A61B 5/002* (2013.01); *A61B 5/0008* (2013.01);
(Continued)

(58) Field of Classification Search
CPC ..... A61B 5/0008; A61B 5/002; A61B 5/0022; G06F 19/3412; G06F 19/3418;
(Continued)

(56) References Cited

U.S. PATENT DOCUMENTS

| 4,870,325 A | 9/1989 | Kazar |
| 6,239,716 B1 | 5/2001 | Pross et al. |

(Continued)

FOREIGN PATENT DOCUMENTS

| CN | 1571375 A | 1/2005 |
| CN | 1886944 A | 12/2006 |

(Continued)

OTHER PUBLICATIONS

Braden, "Requirements for Internet Hosts—Communication Layers," Newwork Working Group, Internet Engineering Task Force, Request for Comment: 1122, pp. 1-117, Oct. 1989.
(Continued)

*Primary Examiner* — Khaled M Kassim
(74) *Attorney, Agent, or Firm* — Bala Ramasamy; The Marbury Law Group

(57) ABSTRACT

Methods and devices provide a wireless communications hub device and services enabling remote access to electronic medical or fitness devices in a manner that simplifies device networking. A wireless communication hub device may include a processor and wireless communication transceivers configured to connect to cellular and/or WiFi networks to access a remote server, and wired and/or wireless local networks for connecting to electronic medical or fitness devices. The wireless communication hub device may plug
(Continued)

into a power source, connect to an electronic medical or fitness device, and communicate via a second wireless network with an associated server-based service. The system enables discovery of the wireless communication hub device and connected electronic medical or fitness devices. The associated remote server based service platform services may provide drivers for various electronic medical or fitness devices, store and forward data, and provide remote access to the various electronic medical or fitness devices.

16 Claims, 40 Drawing Sheets

Related U.S. Application Data

(60) Provisional application No. 61/433,193, filed on Jan. 14, 2011, provisional application No. 61/566,939, filed on Dec. 5, 2011.

(51) Int. Cl.
*A61B 5/00* (2006.01)
*G06F 19/00* (2018.01)
*H04W 8/00* (2009.01)
*H04W 12/08* (2009.01)
*G16H 40/40* (2018.01)
*H04W 4/70* (2018.01)
*H04M 3/42* (2006.01)

(52) U.S. Cl.
CPC ............ *A61B 5/0022* (2013.01); *G06F 19/00* (2013.01); *G06F 19/3418* (2013.01); *G16H 40/40* (2018.01); *H04W 4/70* (2018.02); *H04W 8/005* (2013.01); *H04W 12/08* (2013.01); *H04W 76/11* (2018.02); *G06F 19/3481* (2013.01); *H04M 3/42382* (2013.01)

(58) Field of Classification Search
CPC ........... G06F 19/3481; H04M 3/42382; G16H 40/40; H04L 67/025; H04W 12/08; H04W 4/70; H04W 76/021; H04W 76/11; H04W 8/005
See application file for complete search history.

(56) References Cited

U.S. PATENT DOCUMENTS

| | | | |
|---|---|---|---|
| 6,301,484 B1 | 10/2001 | Rogers et al. | |
| 6,396,466 B1 | 5/2002 | Pross et al. | |
| 6,418,535 B1 | 7/2002 | Kulakowski et al. | |
| 6,548,967 B1 | 4/2003 | Dowling et al. | |
| 7,039,021 B1 | 5/2006 | Kokudo | |
| 7,136,672 B2 | 11/2006 | Kitano et al. | |
| 7,164,907 B2 | 1/2007 | Cochran et al. | |
| 7,202,607 B2 | 4/2007 | Kazar et al. | |
| 7,391,406 B2 | 6/2008 | Yamamoto et al. | |
| 7,618,345 B2 | 11/2009 | Corbalis et al. | |
| 7,761,261 B2 | 7/2010 | Shmueli et al. | |
| 7,902,771 B2 | 3/2011 | Shteynberg et al. | |
| 8,213,971 B2 | 7/2012 | Papineau et al. | |
| 8,271,443 B1* | 9/2012 | Swift | G06F 11/1456 707/640 |
| 8,301,180 B1* | 10/2012 | Gailloux | H04L 12/5875 455/412.1 |
| 8,364,857 B2 | 1/2013 | Pyers et al. | |
| 8,937,930 B2 | 1/2015 | Sprigg et al. | |
| 9,035,568 B2 | 5/2015 | Ganton et al. | |
| 2003/0005092 A1* | 1/2003 | Nelson | G06F 21/88 709/220 |
| 2003/0005100 A1* | 1/2003 | Barnard | H04L 29/12113 709/223 |
| 2003/0157947 A1* | 8/2003 | Fiatal | H04L 12/5895 455/466 |
| 2004/0064453 A1 | 4/2004 | Ruiz et al. | |
| 2004/0073411 A1 | 4/2004 | Alston et al. | |
| 2004/0088180 A1 | 5/2004 | Akins et al. | |
| 2004/0125813 A1 | 7/2004 | Tanaka et al. | |
| 2005/0097191 A1 | 5/2005 | Yamaki et al. | |
| 2005/0248944 A1 | 11/2005 | Sloan | |
| 2005/0269580 A1 | 12/2005 | D'Angelo | |
| 2006/0089542 A1 | 4/2006 | Sands | |
| 2007/0005867 A1 | 1/2007 | Diamant | |
| 2007/0011374 A1 | 1/2007 | Kumar | |
| 2008/0059239 A1* | 3/2008 | Gerst | A61B 5/0002 705/3 |
| 2008/0097908 A1* | 4/2008 | Dicks | A61B 5/0022 705/50 |
| 2009/0058635 A1* | 3/2009 | LaLonde | A61N 1/37282 340/539.11 |
| 2009/0076350 A1* | 3/2009 | Bly | A61B 5/0006 600/301 |
| 2009/0171166 A1* | 7/2009 | Amundson | A61B 5/0002 600/301 |
| 2009/0287405 A1* | 11/2009 | Liu | G01C 21/20 701/119 |
| 2009/0296718 A1* | 12/2009 | Gefflaut | H04L 12/4679 370/395.53 |
| 2010/0017471 A1 | 1/2010 | Brown et al. | |
| 2010/0049885 A1 | 2/2010 | Chandra et al. | |
| 2010/0073659 A1 | 3/2010 | Mikami | |
| 2010/0115279 A1* | 5/2010 | Frikart | G06F 19/3406 713/171 |
| 2010/0211967 A1 | 8/2010 | Ramaswamy et al. | |
| 2010/0269157 A1 | 10/2010 | Experton | |
| 2010/0300856 A1 | 12/2010 | Pance et al. | |
| 2010/0315021 A1 | 12/2010 | Lau et al. | |
| 2010/0318578 A1* | 12/2010 | Treu | G06F 19/3418 707/802 |
| 2011/0090086 A1* | 4/2011 | Dicks | A61B 5/1112 340/573.4 |
| 2011/0109444 A1 | 5/2011 | Edwards et al. | |
| 2011/0167133 A1* | 7/2011 | Jain | H04L 67/12 709/219 |
| 2011/0167250 A1* | 7/2011 | Dicks | A61B 5/1112 713/2 |
| 2011/0179405 A1* | 7/2011 | Dicks | G06F 8/61 717/168 |
| 2011/0205965 A1* | 8/2011 | Sprigg | G06F 9/4411 370/328 |
| 2011/0210674 A1 | 9/2011 | Melanson | |
| 2011/0234409 A1 | 9/2011 | Soliman | |
| 2012/0094612 A1* | 4/2012 | Taylor | H04M 1/72577 455/73 |
| 2012/0182143 A1* | 7/2012 | Gaines | A61B 5/0022 340/539.12 |
| 2012/0182939 A1 | 7/2012 | Rajan et al. | |

FOREIGN PATENT DOCUMENTS

| | | |
|---|---|---|
| CN | 1976310 A | 6/2007 |
| CN | 101084649 A | 12/2007 |
| CN | 101253813 A | 8/2008 |
| CN | 101601040 A | 12/2009 |
| EP | 1411751 A2 | 4/2004 |
| EP | 1659830 A1 | 5/2006 |
| EP | 1753180 A1 | 2/2007 |
| EP | 1753190 A1 | 2/2007 |
| EP | 1887756 A2 | 2/2008 |
| EP | 2209353 A2 | 7/2010 |
| JP | H06311012 A | 11/1994 |
| JP | H06350435 A | 12/1994 |
| JP | H1070540 A | 3/1998 |
| JP | H11243589 A | 9/1999 |
| JP | 2001111544 A | 4/2001 |
| JP | 2002123493 A | 4/2002 |
| JP | 2002125062 A | 4/2002 |
| JP | 2002324052 A | 11/2002 |
| JP | 2003101545 A | 4/2003 |

(56) References Cited

FOREIGN PATENT DOCUMENTS

| | | |
|---|---|---|
| JP | 2003196128 A | 7/2003 |
| JP | 2003318922 A | 11/2003 |
| JP | 2004207820 A | 7/2004 |
| JP | 2004208101 A | 7/2004 |
| JP | 2004304240 A | 10/2004 |
| JP | 2004304623 A | 10/2004 |
| JP | 2005228979 A | 8/2005 |
| JP | 2006005789 A | 1/2006 |
| JP | 2006086675 A | 3/2006 |
| JP | 2006203306 A | 8/2006 |
| JP | 2006245308 A | 9/2006 |
| JP | 2007006320 A | 1/2007 |
| JP | 2007281904 A | 10/2007 |
| JP | 2007528618 A | 10/2007 |
| JP | 2007334581 A | 12/2007 |
| JP | 2009010099 A | 1/2009 |
| JP | 2009516455 A | 4/2009 |
| JP | 2009123452 A | 6/2009 |
| JP | 2009260193 A | 11/2009 |
| JP | 2010100041 A | 5/2010 |
| WO | WO-2001017297 | 3/2001 |
| WO | WO-0227640 A2 | 4/2002 |
| WO | WO-2005048629 A1 | 5/2005 |
| WO | WO-2005069769 A2 | 8/2005 |
| WO | WO-2008052293 A1 | 5/2008 |
| WO | WO-2009032134 A2 | 3/2009 |
| WO | WO-2009135124 A2 | 11/2009 |
| WO | WO-2010038918 A1 | 4/2010 |
| WO | WO-2010063758 A1 | 6/2010 |
| WO | WO-2010077851 A2 | 7/2010 |
| WO | 2010144720 A1 | 12/2010 |
| WO | WO-2011063300 A1 | 5/2011 |
| WO | 2012167200 A1 | 12/2012 |

OTHER PUBLICATIONS

Chen Y., et al., "A Smart Gateway for Health Care System Using Wireless Sensor Network," IEEE, 2010 Fourth International Conference on Sensor Technologies and Applications (SENSORCOMM), Jul. 18-25, 2010, pp. 545-550.

Continua Certification Version 1.0, Continua Health Alliance, Feb. 23, 2009, http://www.continuaalliance.org/static/cms_workspace/Continua_Certification_Public.pdf.

Continua Health Alliance, Apr. 15, 2014, 3 pages, http://www.continuaalliance.org/index.html.

Continua Health Alliance Certification Process, Apr. 14, 2014, 5 pages, http://www.continuaalliance.org/products/cert-process.html.

Datawarehouse, "OLTP vs. OLAP," Mar. 24, 2014, Retrieved from the Internet < URL: http://datawarehouse4u.info/OLTP-vs-OLAP.html >, 2 pages.

Fernando T N C et al., "Ethernet frame tunneling over GPRS/EDGE for universal network monitoring", Industrial and Information Systems (ICIIS), 2009 International Conference on, IEEE, Piscataway, NJ, USA, Dec. 28, 2009 (Dec. 28, 2009), pp. 55-61, XP031647988, ISBN: 978-1-4244-4836-4.

Hirofuchi T et al, "USB/IP—a Peripheral Bus Extension for Device Sharing over IP Network", Proceedings of the USENIX Annual Technical Conference, XX, XX, Jan. 1, 2005 (Jan. 1, 2005), pp. 47-60, XP007901448.

Jerger, et al., "Memoirs of an eHealth Device Development," 2011 IEEE 13th International Conference on e-Health Networking, Applications and Services, pp. 332-337, 2011.

Mitchell B., "Wireless Standards—802.11a, 802.11 b/g/n, and 802.11ac, The 802.11 Family explained," Apr. 14, 2014, 2 pages, About.com Guide, http://compnetworking.about.com/cs/wireless80211/a/aa80211standard.html.

Part 11 :Wireless LAN Medium Access Control (MAC) and Physical Layer (PHY) Specifications, ANSI/IEEE Std 802.11, XX, XX, Jun. 12, 2003 (Jun. 12, 2003), pp. 34-88, XP002382009.

Vicente K.S., "ANT Wireless. Go Beyond," Apr. 15, 2014, 2 pages, http://www.thisisant.com.

Wi-Fi Alliance, "Who We Are," Apr. 15, 2014, 2 pages, http://www.wi-fi-org/Wireless Standards 802.11.

Wikipedia, "IEEE 802.11," Wireless Standards 802.11, Apr. 13, 2014, 15 pages, http://en.wikipedia.org/wiki/802.11.

Wikipedia, "Online Analytical Processing," Mar. 24, 2014, 7 pages, http:///en.wikipedia.org/wiki/online_analytical_processing.

Murakami A., et al., "Collection of Information of Equipment and an Alarm Monitoring System for an Intensive Care Area", Medical Informatics, Japan, Japan Association for Medical informatics, Mar. 31, 2008,Issue 27, No. 5, (Serial No. 127), pp. 415 to 423.

* cited by examiner

TELEHEALTH WIRELESS COMMUNICATION HUB DEVICE AND SERVICE PLATFORM SYSTEM

RELATED APPLICATIONS

This application is a divisional application of, and claims the benefit of priority to, U.S. Non-Provisional patent application Ser. No. 13/349,938 entitled "Telehealth Wireless Communication Hub Device and Service Platform System" filed Jan. 13, 2012 which claims the benefit of priority to U.S. Provisional Patent Application No. 61/433,193 entitled "Telehealth Wireless M2M Communication Hub And Service Platform System" filed Jan. 14, 2011, and U.S. Provisional Patent Application No. 61/566,939 entitled "Telehealth Wireless M2M Communication Hub And Service Platform System" filed Dec. 5, 2011. The entire contents of all three applications are hereby incorporated herein by reference.

FIELD OF THE INVENTION

The present invention relates generally to computer networks, and more particularly to a wireless communication hub for coupling medical devices to remote medical service and support providers by way of an intermediate server.

BACKGROUND

There is an ever growing population of electronic medical devices, many of them configured for home use. While the capabilities of such medical devices are significant, little integration of such medical devices, medical systems, and medical institutions have been accomplished. One of the challenges preventing such integration is that most electronic medical devices have been developed without regard to communication interfaces. Thus, no standard communication protocols or technologies have been implemented that could serve as an integrating backbone.

BRIEF DESCRIPTION OF THE DRAWINGS

The accompanying drawings, which are incorporated herein and constitute part of this specification, illustrate exemplary embodiments of the invention, and together with the general description given above and the detailed description given below, serve to explain the features of the invention.

DETAILED DESCRIPTION

Figure 1A:
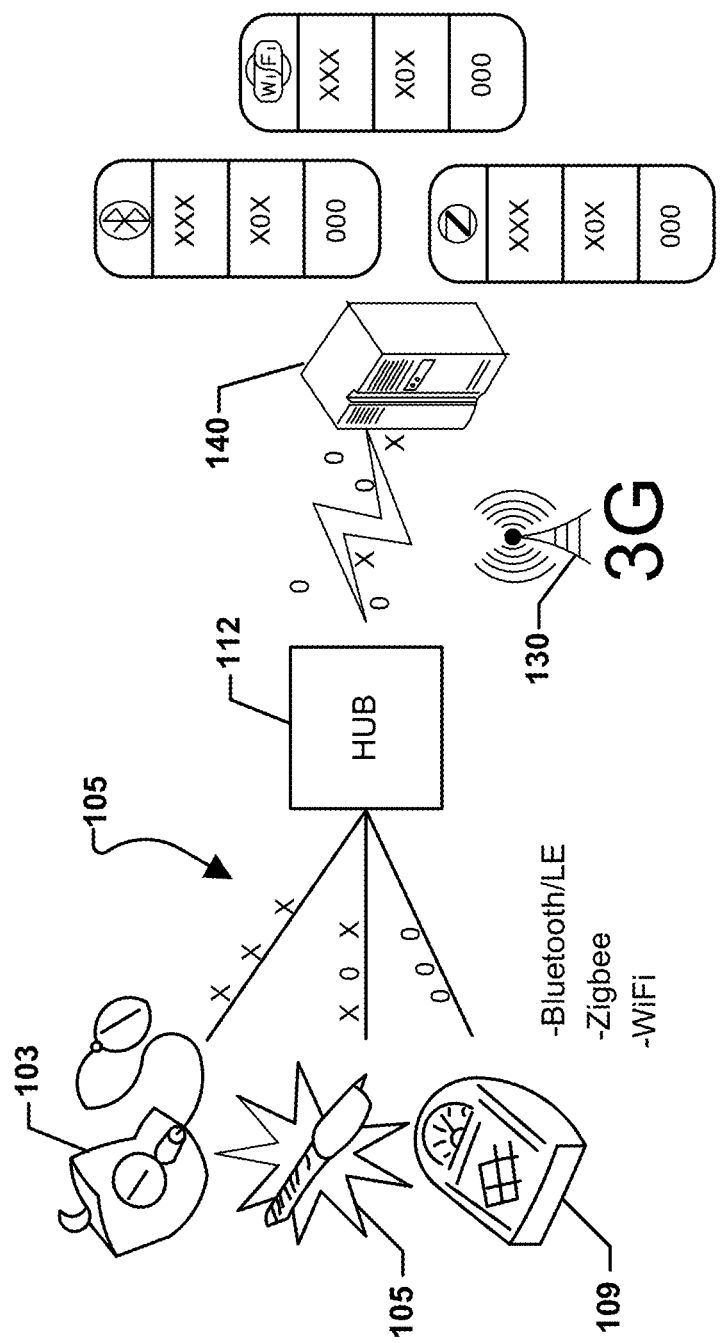
FIGS. 1A-1C are communication system block diagrams illustrating communication systems suitable for use with various embodiments.

The various embodiments will be described in detail with reference to the accompanying drawings. Wherever possible, the same reference numbers will be used throughout the drawings to refer to the same or like parts. References made to particular examples and implementations are for illustrative purposes, and are not intended to limit the scope of the invention or the claims.

As used herein, the terms "computer," "personal computer" and "computing device" refer to any programmable computer system that is known or that will be developed in the future. In a preferred embodiment a computer will be coupled to a network such as described herein. A computer system may be configured with software instructions to perform the processes described herein.

As used herein, the terms "component," "module," "system," and the like are intended to refer to a computer-related entity, either hardware, a combination of hardware and software, software, or software in execution. For example, a component may be, but is not limited to being, a process running on a processor, a processor, an object, an executable, a thread of execution, a program, and/or a computer. By way of illustration, both an application running on a server and the server can be a component. One or more components may reside within a process and/or thread of execution and a component may be localized on one computer and/or distributed between two or more computers.

As used herein, the term "device" refers to any electronic device, several examples of which are mentioned or described herein. In a preferred embodiment, a device includes a communication port enabling the device to be coupled to another computing device or a network.

Various aspects will be presented in terms of systems that may include a number of components, modules, and the like. It is to be understood and appreciated that the various systems may include additional components, modules, etc. and/or may not include all of the components, modules, etc. discussed in connection with the figures. Also, it is to be understood and appreciated that a number of components and modules may be combined into integrated circuits or chipsets. A combination of these approaches may also be used.

The various embodiments described herein provide devices, systems and methods that enable connecting any number of a variety of electronic medical devices to remote medical suppliers, services and facilities via a machine to machine (M2M) communication hub which communicates data to and from a remote service platform server in order to simplify networking of personal medical devices with telemedicine systems and databases. The various embodiments include a communication hub device (referred to herein interchangeably as a wireless M2M communication hub, virtual personal hub (VPH), communication hub device, wireless communication hub device, and/or hub) which includes a processor and communication transceivers configured to provide a communication link between electronic medical and fitness equipment which may be in a user's home, office, or medical/fitness facility and an external server which can receive and process medical and/or fitness data. In particular, the wireless communication hub device is configured to connect to wireless wide are networks (WWAN) (e.g., cellular telephone) and/or WiFi communication networks to provide one side of a communication link, and to medical, fitness and personal sensors via wireless (e.g., BlueTooth®) and wired (e.g., USB) local communication links to provide the other side of the communication link. Thus, the wireless communication hub device can serve as the connection gateway between a variety of different types of medical, fitness and personal sensor devices which can only communicate locally, and remote servers, remote facilities, and data server/storage systems which can use the data of such devices but are only coupled to the Internet. In order to accommodate the different data structures, communication protocols, systems, and driver software of any of a variety of electronic devices, the wireless communication hub device may communicate, such as via WWAN or WiFi wireless communication links, with a remote server that provides a service platform of functionalities. Such a service platform server may then facilitate the communication of data between users of the device data on one side, and the details of communicating with and controlling a wide variety of electronic devices on the patient's end.

Electronic medical and fitness devices have been developed by a large number of manufacturers who have focused on the medical aspects of their products, and have only recently considered or added communication capabilities. As a result, there has been little if any cooperation on communication protocols and technologies. Thus, the universe of electronic medical and fitness equipment lacks any kind of coordination or standards that would facilitate connecting such devices to the facilities and services that could use the data. To solve this problem, the various embodiments provide a wireless gateway or hub that is capable of collecting the healthcare data from any of a variety of electronic medical and fitness devices, such as in the home setting, and sending this data over the wireless communication network, such as a cellular telephone wireless network (i.e., WANN), back to a centralized server. The wireless communication hub device may include a variety of wireless communication transceivers, such as WiFi, Bluetooth, Zigbee, and ANT+ transceivers, in order to enable the wireless communication hub device to communicate with devices that do not have a standard communication capability and/or do not comply with a widely used communication standard. In the future, electrical medical and fitness devices may be configured with a standard wireless data link, such as Bluetooth®, in which case the wireless communication hub device may be simplified to utilize that single standard local area wireless communication transceiver.

In an embodiment, the wireless communication hub device may be used in the home setting to enable electronic medical and fitness devices to communicate data regarding a patient in the residence to remote users of such data. In an embodiment, the wireless communication hub device may be plugged into a standard wall electrical socket to receive power, and then search out and pair with wireless electronic medical and fitness devices, such as blood pressure monitors, glucose meters, treadmills, etc. using the wireless communication links of such devices. Such pairing and establishing the communication links may be accomplished automatically, thereby minimizing the configuration and setup burden for the patient. The wireless communication hub device may collect data provided by the various electronic medical and fitness devices in the home, package the data into suitable packets for communication via wireless and Internet communication links, and send the data packets back to the central server (i.e., a service platform server or virtual personal hub (VPH) server) using a wireless wide area network (WWAN) communication link, such as an LTE, 3G or 4G cellular communication network. In order to enable the greatest ease of setup, lack of complexity and security for this medical communication system, the wireless communication hub device and the central server (i.e., service platform server) may be configured to provide for automatic device discovery, communication links setup, security key exchange, data addressing, and device configuration. Thus in an embodiment, a patient may simply plug the wireless communication hub device into an electrical outlet to establish a communication network between the wireless electronic medical and fitness devices in the patient's home and those facilities and services that can utilize the medical and fitness data generated by such devices. Using suitable encryption mechanisms, the data may be transferred securely while maintaining the appropriate security required under government regulations (e.g., HIPPA).

In a simple embodiment, the wireless communication hub device may be configured as a small, integrated module that can be plugged into a power source, such as a standard utility wall socket, and attached (wirelessly or via a wired connection like USB) to one or more medical or fitness devices (e.g., a blood pressure sensor, a glucose monitor, a pedometer, a treadmill, etc.). The wireless communication hub device may be configured with processor-executable software to enable connected electronic medical and fitness devices to be used from any computer attached to a local area network or the Internet. An associated Internet server-based service platform enables discovery of the wireless communication hub device and connected electronic medical and fitness devices. The wireless communication hub device may also be accessed from the Internet through the associated server-based service.

The various embodiments of the wireless communication hub device ("hub" or "2net HUB" in the drawings), minimize the complexity of networking electronic medical and fitness devices by eliminating many of the requirements conventionally imposed on a host system and local network. Wireless communication hub devices can be placed in any location, stationary or mobile, and are configured so that the electronic medical and fitness devices connected to the wireless communication hub device appear to the accessing computers as if they are locally connected. This is accomplished by way of intelligence and connectivity in the wireless communication hub device, the associated server-based service and, optionally, software that may be hosted on the accessing computer.

The various embodiments also simplify the traditionally challenging technical processes of networking electronic medical and fitness devices, such as setup and initialization, security, driver management, and device sharing by way of a server-based supporting service element. This service may also enable valuable communication and data utilization capabilities, such as batch operation support; access via the Web and intelligent sharing across user defined and controlled groups.

In order to provide a "universal" hub to handle health-sensitive data from any of a variety of electronic medical and fitness devices, a number of different radios may be implemented within the wireless communication hub device. Multiple radios each potentially serving multiple devices increases the complexity of design, but simplifies the process of establishing communication networks between electronic medical and fitness devices and remote users of data from those devices. Employing multiple radios in the wireless communication hub device enables manufacturers of various electronic medical and fitness devices to be able to pair up with the hub without significant changes to their devices, thus enabling them to avoid the need to be concerned with communication protocols and data encryption. This enables the wireless communication hub device to function as a data-in/data-out device, with its only function being to collect, package and faithfully transfer data to the service platform server.

In addition to supporting multiple radio protocols, including Bluetooth®, WiFi and ANT+, a software scheme may be implemented within the wireless communication hub device to accommodate a wide range of customizations. To support this, the hub processor may be configured with a high-functionality operating system, such as the Android operating system.

A wireless communication hub device may be configured to use software interface models that mirror the types of devices that can be connected to computers via USB (Universal serial bus) or FireWire ports. In short, the wireless communication hub device embodiments can broaden and extend the value of many connected electronic medical and fitness devices. Employing the wireless communication hub device, electronic medical and fitness devices can be placed virtually anywhere, shared across groups, accessed via the Internet or local networks, and supported by extended services which enable new use models and revenue opportunities.

In order to comply with regulations imposed on medical equipment, the wireless communication hub device may be developed under ISO 13485 standards that are required for medical devices. This would enable wireless communication hub device systems to be sold in combination with one or more medical devices as a system.

In an embodiment, the wireless communication hub device may be configured to receive and send messages over a cellular wireless network, such as simple message service (SMS) messages. As an example, a SMS message may be sent from a remote server (i.e., service platform server) to the wireless communication hub device, or from the wireless communication hub device to the remote server. The SMS messages may be any type SMS message, such as SMS messages having a payload (i.e., includes payload data) and SMS messages that are payload-less (i.e., includes no payload data). In an embodiment, the receipt of an SMS message may trigger the wireless communication hub device to perform a task. In this manner, just the reception of an SMS message, regardless of its payload or lack of payload, triggers the communication hub device to takes an action which may be predefined, such as contacting the remote server for further instructions. In an embodiment, the remote server may send an SMS message to the wireless communication hub device to activate the wireless communication hub device. In a further embodiment, the wireless communication hub device may be configured to establish a connection with the remote server, such as a data connection or WWAN connection, in response to receiving an SMS message. In an embodiment, if a data call between the remote server and the wireless communication hub device cannot be established, the remote server may send an SMS message to the wireless communication hub device. In an embodiment, the remote server may send an SMS message to the wireless communication hub device if the remote server needs to immediately establish a data call with the wireless communication hub device. In an embodiment, the remote server may determine that the period of time since the remote server last received data from the wireless communication hub device has passed an established minimum connection periodicity (i.e., a predetermined connection periodicity value), and may transmit an SMS message to the wireless communication hub device to ensure continuity of communication with the remote server.

In the various embodiments, SMS messages may be sent to and from the wireless communication hub device to direct or manage: the updating of software, updating of firmware, running diagnostics and reporting of the results of diagnostics, the update of pairings with the electronic medical and fitness devices, checks of security settings of the wireless communication hub device. As mentioned above, in an embodiment, the SMS message need not include a payload, and the reception alone may trigger an action. In an embodiment, a payload of the SMS message may include an indication for the wireless communication hub device to execute a task and/or data for use by the wireless communication hub device. In an embodiment, the information in a payload-less SMS message, such as the originating phone number, may be an indication to the wireless communication hub device to execute a certain task. In this manner, different originating phone numbers may be indications of different tasks to be executed. In an embodiment, an SMS message may enable selective data retrieval, such as by including an indication of a specific portion of stored data on the wireless communication hub device to be transmitted to the remote server.

In an embodiment, the wireless communication hub device may transmit a SMS message to a remote server (e.g., a service platform server). In an embodiment, SMS messages may be initiated by the wireless communication hub device in response to determining the unavailability of a primary network connection with the remote server, such as when the primary data connection is lost. In an embodiment, SMS messages may be sent from the wireless communication hub device to the remote server to convey an exception within the electronic medical and fitness devices. In an embodiment, SMS messages may be sent by the wireless communication hub device to upload data to the remote server. In an embodiment, SMS messages may be sent and/or received by the wireless communication hub device to troubleshoot the data call or network coverage issues.

FIG. 1A illustrates system components that may be included in the communication system that is enabled by the various embodiments. As illustrated in FIG. 1A, a variety of electronic medical or fitness devices 102, 104, 108 (e.g., a blood pressure sensor, a glucose sensor, and a scale) may transmit data via a local network 105 (such as a local area wireless network (e.g., WiFi, Bluetooth, Zigbee, and ANT+) or wired network (e.g., USB)) to the wireless communication hub device 112, which packages the data encrypted and transmits it via a wireless communication link, such as a wireless wide area network 130 (e.g., 3G cellular wireless network), to a service platform server 140 where the data may be unpacked and stored in a database or transferred to other systems where the data may be stored and processed. FIG. 1A also provides a high-level illustration of the flow of data from various electronic medical and fitness devices through the hub over three short range radio protocols. The various embodiments, the data collected from each device may be encrypted and securely managed from end-to-end so that each data set is stored in its own, perhaps proprietary format, by the device and by technology. In this manner, the wireless communication hub device acts as a gateway that securely enables wireless transport of data or information from the various electronic medical and fitness devices through the service platform server to the caregiver or provider's servers and databases located in the Internet cloud.

For example, when a medical device, such as a blood pressure monitor or weight scale, is in the vicinity of the wireless communication hub device, the data received from that device (e.g., blood pressure readings, wait, etc.) may be sent to databases within the Internet cloud. Additionally, the system may enable caregivers and medical facilities to send a command or diagnostic message to a medical or fitness device within the patient's home, in which case such commands can be routed via the Internet to the service platform server which can then transmit them via the established wireless communication link to the wireless communication hub device, which can then communicate them to the intended medical or fitness device.

Figure 1B:
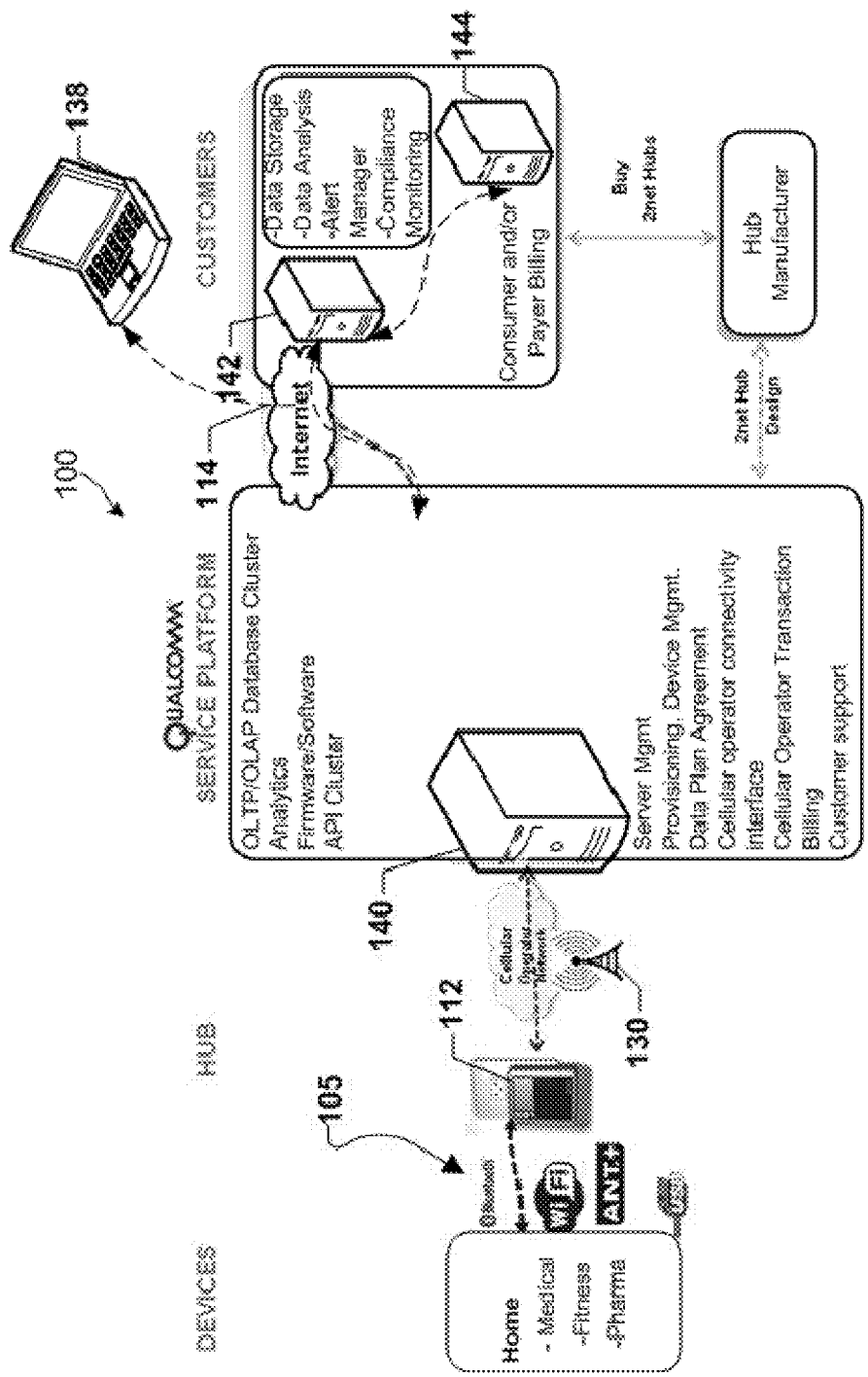
Figure 1C:
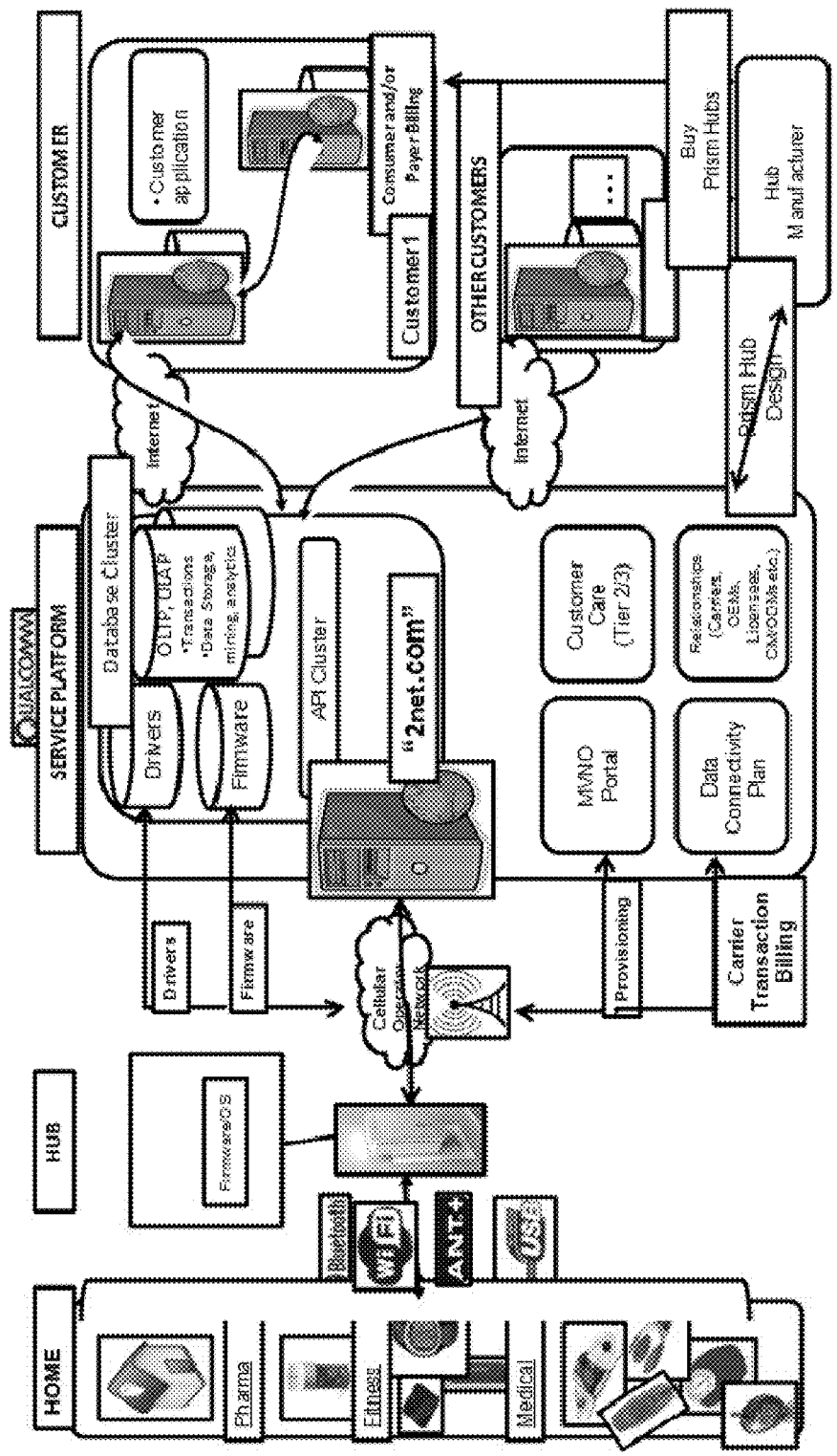

FIG. 1B illustrates a communication network 100 and some of the functionality and functional modules that may be implemented within the service platform server 140, as well as functions that may be accomplished by customer and caregiver servers 142, 144 receiving data via the Internet 114 from the service platform server 140. FIG. 1C illustrates the communication system in more detail.

As illustrated in FIGS. 1B and 1C, the service platform server 140 may include memory and maintain its own database for storing or buffering data received from various medical and fitness devices. The service platform server 140 may also perform some analytics on the received data, such as comparing data to alarm settings to determine whether any urgent actions or alarms should be communicated to the patient or to healthcare providers. The service platform server 140 may also be configured with provisioning and device management software, data plan agreement management software, cellular operator connectivity interface functionality, cellular billing functionality and customer support services. The references to 3G cellular wireless networks herein are for example purposes only. In some embodiments, lower-cost "2G" components and networks may be utilized. However, in order to remain compatible with cellular wireless networks as cellular providers transition their systems to higher capability LTE, 3G, and 4G networks, embodiments may implement LTE, 3G and/or 4G radio technology and communication protocols.

The wireless communication hub device system 100 may include two core elements, the wireless communication hub device 112 and a service platform server ("2net Service Platform" in the figures) 140. The wireless communication hub device 112 may be sold to consumers and may be attached by USB, FireWire or wireless communication links to wireless electronic medical and fitness devices 102, 104, 108. The service platform server 140 is coupled to the Internet 114 and provides a variety of service platform services, such as secure access to the wireless communication hub device 112 to enable receiving data from and connecting to the electronic medical and fitness devices 102, 104, 108.

The wireless communication hub device 112 may connect to electronic medical and fitness devices 102, 104, 108 via direct (i.e., wired) connections, such as a USB connection, a FireWire connection, or local area network connection (e.g., Ethernet), as well as wireless communication links, such as Bluetooth, WiFi, ZigBee and ANT+ wireless communication networks.

The service platform server 140 may be configured to provide a variety of data and communication services related to wireless communication hub devices 112, the electronic medical and fitness devices 102, 104, 108 that may be connected to them, and data that may be obtained from such electronic medical and fitness devices 102, 104, 108. Such services are generally referred to herein as "service platform services." One service platform service provided by the service platform server 140 may support user-authenticated discovery and communication between the electronic medical and fitness devices 102, 104, 108 connected to the wireless communication hub device 112 and remote computer(s) 138 accessing the electronic medical and fitness devices 102, 104, 108. This capability may enable health care providers and medical data users to setup accounts that provide access to the electronic medical and fitness devices 102, 104, 108 coupled to one or more wireless communication hub devices 112 registered to them. Authentication may be accomplished by the service platform server 140 with respect to the wireless communication hub device 112, electronic medical and fitness devices 102, 104, 108 coupled to the wireless communication hub device 112, a computer 138 accessing the service platform server 140 via the Internet 114, and/or the user of a computer 138 using any known device and user authentication methods. This service may employ a custom protocol to communicate with particular electronic medical and fitness devices 102, 104, 108 connected to a wireless communication hub device 112.

The service platform services may also handle normal interfacing and device management issues, such as allowing wireless communication hub devices 112 to enter an idle mode to minimize over-the-air (OTA) usage charges, and waking up an idle wireless communication hub device 112 when needed. Like the wireless communication hub device's 112 handling of electronic medical and fitness devices 102, 104, 108, the data protocol between the service platform server 140, the wireless communication hub device 112, and the accessing computer(s) 138 can be generic, enabling support for almost any current and future electronic medical and fitness devices 102, 104, 108 or server based data system. The wireless communication hub device 112 may register connected electronic medical and fitness devices with the service platform server 140, making electronic medical and fitness devices available to authorized remote servers 142, 144 and computers 138 (e.g., a physician's personal computer).

The service platform provides client services enabling access to the remote electronic medical and fitness devices 102, 104, 108 may be facilitated for any type of computer 138 capable of hosting the software necessary to access the service platform server, regardless of whether that computer 138 has the native ability to host locally connected electronic medical and fitness devices 102, 104, 108. Thus, accessing computer(s) 138 may include mobile devices (e.g., phones, smartphones, etc.) with applications capable of accessing the data from the service platform server 140. The service platform services may also include "machine to machine" (M2M) applications where the remotely accessing computer 138 supports no direct human interaction.

Another service of service platform services may be the setup and configuration of the wireless communication hub device 112, including support for the addition and removal of connected electronic medical and fitness devices 102, 104, 108, and connectivity by remote computers 138 (e.g., the personal computer of an attending physician). For example, an attending physician may login to the service platform service, identify the position's patient, authenticate himself, and thereby gain access to medical data from electronic medical devices within the patient's home so as to determine the current condition of the patient. The various embodiments enable this telemedical communication system to be established simply by plugging a wireless communication hub device 112 into a power outlet within the patient's home and providing the physician with the URL for the service platform server 140.

Another service of the service platform services may be user-based authentication using mechanisms that can be used to associate an authenticated user and computer 138 with the wireless communication hub device 112 and its connected electronic medical and fitness devices 102, 104, 108. Data, particularly personal information and medical data, transmitted between the wireless communication hub device 112, the service platform server 140 and computers 138 may be encrypted by the wireless communication hub device 112 to enhance the privacy of the transmitted data and comply with the HIPPA regulations.

The service platform services may also enable accessing electronic medical and fitness devices 102, 104, 108 from any Internet-connected computer (e.g., web kiosks) when a user is away from the user's personal computer 138. The service platform services may also include storage, relaying and utilization of data obtained from electronic medical and fitness devices 102, 104, 108 connected to a wireless communication hub device 112. Such utilization of electronic medical and fitness device data made possible by the various embodiments may enable a variety of useful applications.

In a further embodiment, intelligence in the wireless communication hub device 112 and service platform server 140 may enhance the efficiency of wireless data transmission, facilitating an appearance of persistence in the connection to the electronic medical and fitness devices 102, 104, 108 while minimizing wireless/cellular network overhead. In this manner, the service platform server 140 may "host" the latest data or status from electronic medical and fitness devices 102, 104, 108 for access by computer(s) 138 enabling the appearance that the electronic medical and fitness devices 102, 104, 108 are continuously connected to a computer 138 (e.g., a physician's personal computer) accessing the electronic medical and fitness devices 102, 104, 108 via the service platform server 140. This appearance of continuous connectivity may be achieved without the need to maintain a constant communication link between the electronic medical and fitness devices 102, 104, 108, the wireless communication hub device 112 and the service platform server 140. Depending upon the nature of the electronic medical and fitness device 102, 104, 108, data provided by the electronic medical and fitness device 102, 104, 108, status states of electronic medical and fitness device 102, 104, 108, or current circumstances, establishment of an active communication link to transmit updated data from the electronic medical and fitness device 102, 104, 108 may be accomplished on an as-needed basis. By configuring the wireless communication hub device 112 and the service platform server 140 with intelligence, a wide variety of electronic medical and fitness device 102, 104, 108 applications may be supported while minimizing communication costs.

As mentioned above, users' personal computer(s) 138 may be provisioned with wireless communication hub device driver software modules. The basic function of such driver software may be to support transparent access to electronic medical and fitness devices 102, 104, 108 connected to a wireless communication hub device 112. Such driver software may provide virtualized access to the USB or FireWire port across a local network or a wide area network (e.g., the Internet 114), and may be used to support secure access to wireless communication hub devices 112 through the service platform server 140. Such driver software may be made available from a service platform services website (such as may be hosted by the service platform server 140), and may include the necessary encryption keys to access specific electronic medical and fitness devices 102, 104, 108 coupled to a wireless communication hub device 112 associated with a patient. Such encryption keys may be generated during the electronic medical and fitness device 102, 104, 108 setup, registration and configuration phase.

Unlike a common single physical cable connection between the electronic medical and fitness devices 102, 104, 108 and an attached computer 138, the virtual nature of the connectivity to the electronic medical and fitness devices 102, 104, 108 via the wireless communication hub device 112 allows more than a single computer to access the same remote electronic medical and fitness device 102, 104, 108 at a given time. Likewise, the electronic medical and fitness devices 102, 104, 108 connected to the wireless communication hub device 112 may be accessed by a number of different remotely accessing computers 138. Further, the connectivity and access permissions configuration may be changed at any time by remote computers 138 interfacing with the service platform server 140.

Third-party servers 142, 144 may communicate with the service platform server 140 via the Internet 114 to receive data from or communicate data to electronic medical and fitness devices 102, 104, 108 connected to a wireless communication hub device 112.

An example of an application of the communication network 100 illustrated in FIGS. 1A and 1B is the transmission of data from medical or fitness device 102 (e.g., a blood pressure ("BP") sensor). Once the wireless communication hub device 112 is installed and registered with the service platform server 140, it can be connected to the medical and fitness device, such as a medical or fitness device 102 (e.g., a blood pressure ("BP") sensor), by a cable (e.g., a USB cable or FireWire cable) or a wireless communication link (e.g., a Bluetooth®). Once connected, the wireless communication hub device 112 may report the connection with the medical or fitness device 102 (e.g., a blood pressure ("BP") sensor) to the service platform server 140 which may maintain data records for storing data received from the sensor, medical device or fitness device. Data records may be maintained in a user account, in an account associated with the communication hub device and/or each medical or fitness device.

Data packets received from the medical or fitness device 102 (e.g., a blood pressure ("BP") sensor) by the wireless communication hub device 112 may be encapsulated in IP packets which are relayed as cellular data communications to a cellular wireless network 130 which applies them to the Internet 114 for delivery to the service platform server 140. By tunneling the data packets received from the medical or fitness device 102 (e.g., a blood pressure ("BP") sensor) to the service platform server 140 within encapsulated IP packets, the wireless communication hub device 112 does not have to be configured with driver software module(s) for interacting with the medical or fitness device 102 (e.g., a blood pressure ("BP") sensor). Instead, the encapsulating IP packets from the wireless communication hub device 112 may be received by the service platform server 140, which unpacks the packets so the medical or fitness device 102 (e.g., a blood pressure ("BP") sensor) data may be processed by the driver software module appropriate for the medical or fitness device 102 resident on the service platform server 140 and the translated data may be stored on the service platform server 140. In this manner the processing of the electronic medical or fitness device data in the service platform server 140 using a driver appropriate for the electronic medical or fitness device 102 may enable storage of translated data that may be in a useful format to various data users.

With the medical or fitness device 102 (e.g., a blood pressure ("BP") sensor) data stored on the service platform server 140, this medical or fitness device 102 (e.g., a blood pressure ("BP") sensor) data may be made accessible via the Internet 114 to other entities which may have use for the medical or fitness device 102 (e.g., a blood pressure ("BP") sensor) data. For example, the stored medical or fitness device 102 (e.g., a blood pressure ("BP") sensor) data may be transmitted to a doctor's computer 138 or hospital server 142 as hypertext transfer protocol IP (HTTP/IP) packets, such as in response to queries posed to a website hosted by the service platform server 140. In an embodiment, the doctor's computer 138 may use a driver appropriate for the electronic medical or fitness device 102 to view the electronic medical or fitness device data.

The communication network 100 may also enable hardware manufacturers to control or limit the distribution of driver software in order to maintain control over the data or electronic medical and fitness devices for which they are responsible. For example, some medical device manufacturers may choose to maintain device drivers as proprietary software so that data from their products can only be interpreted by their in-house servers. Such limitations may be appropriate to prevent storage of sensitive patient information on databases accessible via the Internet 114. Such limitations may also be appropriate to ensure that medical devices cannot be reprogrammed or controlled by unauthorized individuals. To support such an implementation, the service platform server 140 may forward unprocessed data packets received from such a proprietary sensor (e.g., a blood pressure sensor) as encapsulated IP packets to the device manufacturer's server 144 via the Internet 114, or another network (not shown). The manufacturer's server 144 may then use its proprietary driver software to interpret the data received from the electronic medical and fitness device.

As noted above, the communication link to the electronic medical and fitness devices 102, 104, 108 (e.g., blood pressure sensor) enabled by the service platform server 140 and wireless communication hub device 112 can support reverse communications in a similar manner. Thus, a medical facility or manufacture of the electronic medical and fitness device may transmit settings commands to the device using the communication links illustrated in FIG. 1B. For example, a doctor receiving readings from the medical or fitness device 102 (e.g., a blood pressure ("BP") sensor) via a medical server 142 may transmit a message to be displayed on a screen of the medical or fitness device 102 (e.g., a blood pressure ("BP") sensor) or another electronic medical and fitness device coupled to the wireless communication hub device 112.

One challenge faced by those who set up local wireless networks involves discovering and establishing communication links with all devices that may be accessed via the network. This challenge is simplified by the services provided by the wireless communication hub device 112 and the service platform server 140.

When the wireless communication hub device 112 is installed and initially activated, it may report to the service platform server 140 all of the commercial devices coupled to it by wired (e.g., USB connector, FireWire) or wireless links (e.g., BlueTooth® link). As part of the registration process the service platform server 140 may assign unique IPv6 addresses to each of the electronic medical and fitness devices 102, 104, 108 coupled to the wireless communication hub device 112. These IPv6 addresses can then be used by a local computer 138 to access specific electronic medical and fitness devices 102, 104, 108 via the wireless communication hub device 112. Thus, to access a particular electronic medical and fitness device 102, 104, 108, a user may use a personal computer 138 coupled to the Internet 114 via a local wireless router to access the service platform server 140. After registering with the service platform server 140, such as by entering a username and password or exchanging verification keys, the user may request and receive a listing of all electronic medical and fitness devices 102, 104, 108 coupled to the wireless communication hub device 112, including their IPv6 addresses. Once the user's personal computer 138 has the IPv6 addresses of the electronic medical and fitness devices 102, 104, 108, the computer 138 may then access particular electronic medical and fitness devices 102, 104, 108 via wireless communications through the wireless router to the wireless communication hub device 112. Command signals, such as data access requests, transmitted by the local computer 138 that are addressed to a particular electronic medical and fitness device 102, 104, 108, using the IPv6 address provided by the service platform server 140 will be relayed by the wireless communication hub device 112. Thus, one of the service platform services enabled by the various embodiments is simplified network establishment with electronic medical and fitness devices coupled to the wireless communication hub device 112.

The various embodiments of the wireless communication hub device and the service platform services can enable rapid and efficient deployment of existing and future electronic medical and fitness devices (e.g., cameras, etc.) to locations and circumstances which may not currently lend themselves well to such deployments. For example, a battery powered wireless communication hub device may be coupled to electronic medical devices without the need for running cables, configuring routers and networks, or configuring the devices. Connectivity and configuration, including providing drivers for receiving the camera imagery can be handled automatically by the wireless communication hub device and the service platform services. In this manner, a telemedicine communication link can be established to a patient or an ad hoc medical station at a scene of an accident, in a sporting event (e.g., a marathon) or on the battlefield without the need for an infrastructure any more complex than access to a cellular communication network.

Figure 2:
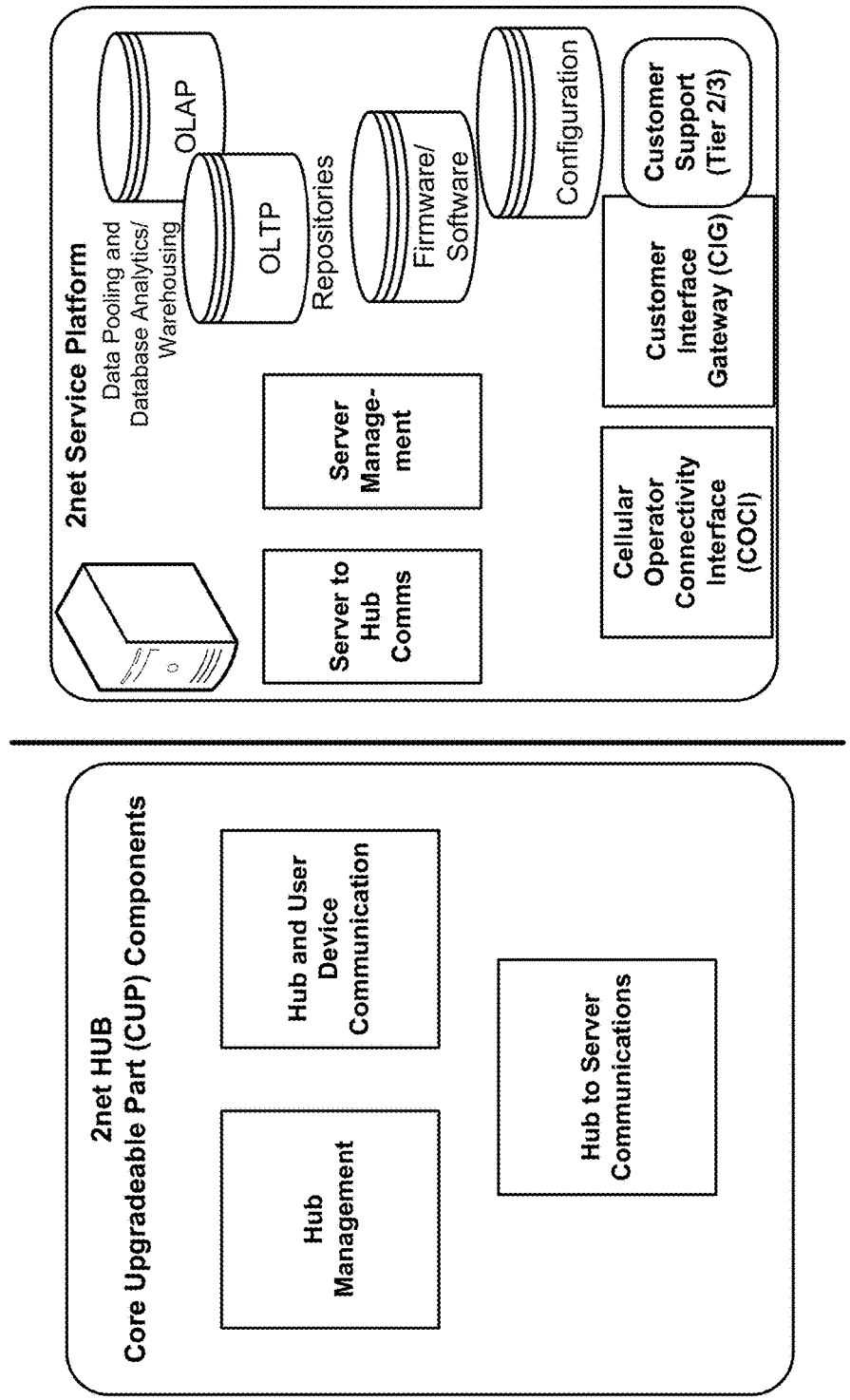
FIG. 2 illustrates functional components of various embodiments.

FIG. 2 shows a high-level block diagram of the key components of the wireless communication hub device and the Service Platform hosted on the service platform server.

Figure 3A:
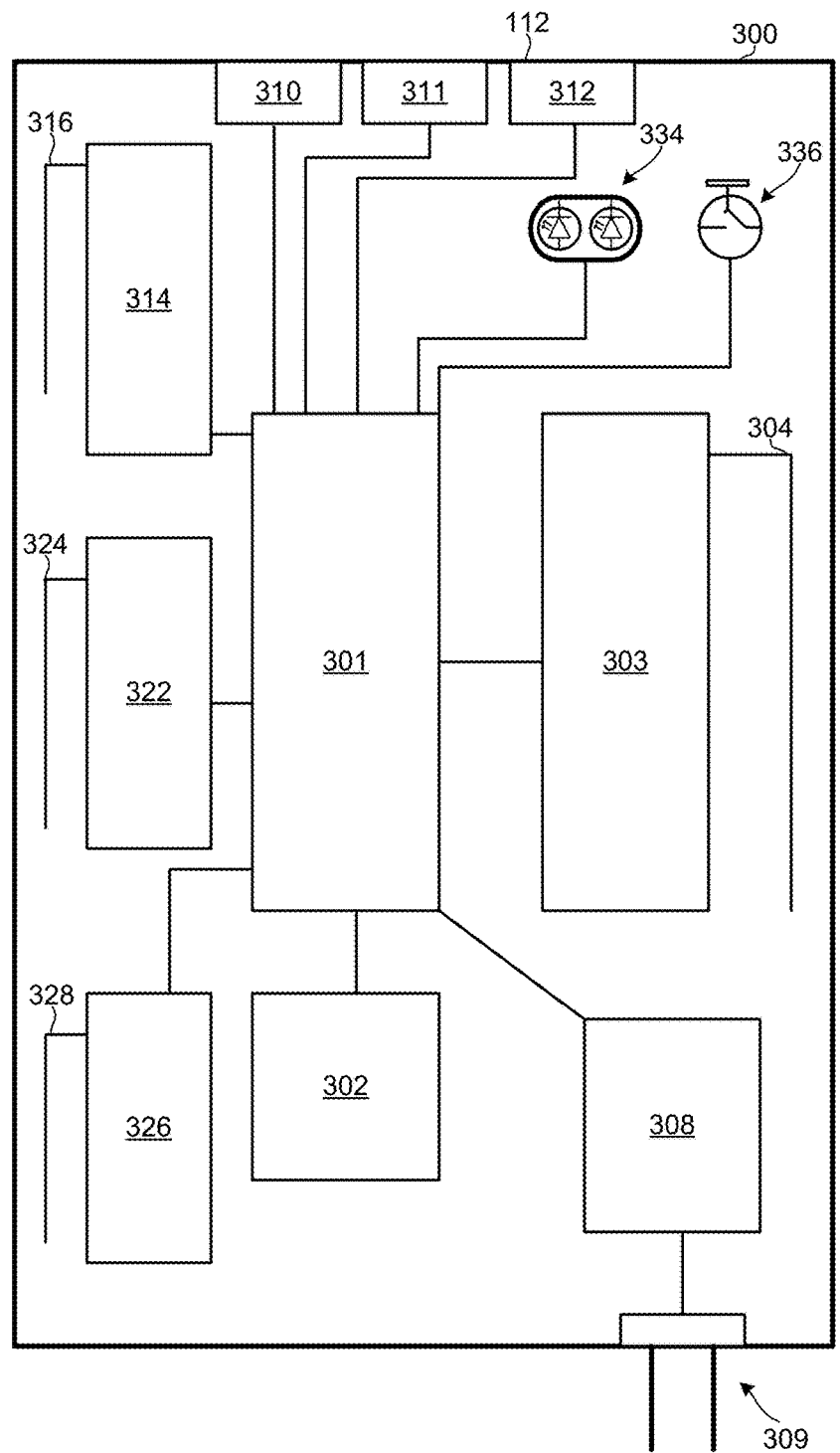
FIGS. 3A and 3B are component block diagrams of a wireless communication hub device according to an embodiment.
Figure 3B:
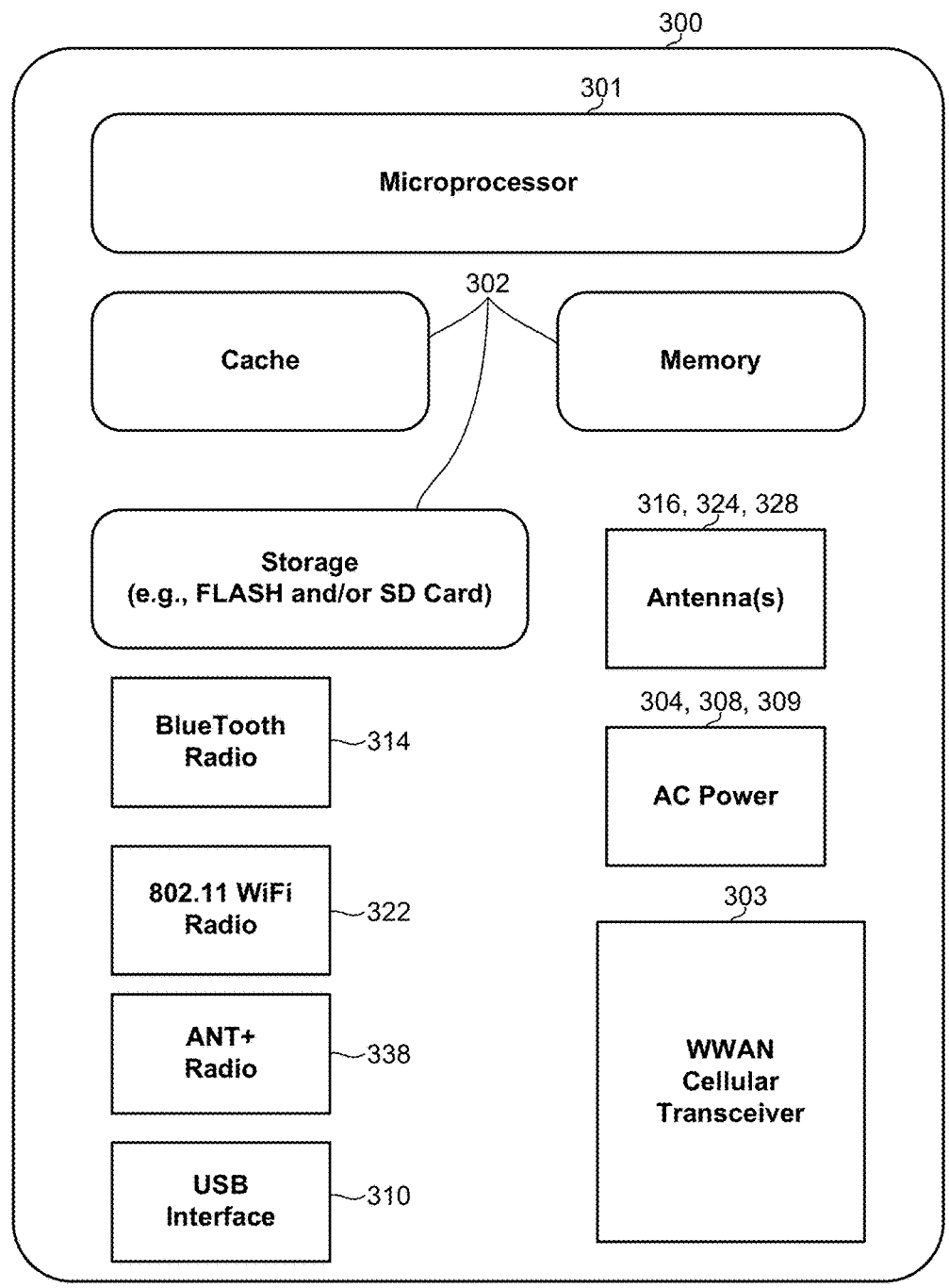

Example components of a wireless communication hub device 112 embodiment are illustrated in FIGS. 3A and 3B.

The wireless communication hub device 112 may be configured in a case or housing 300 and may include a programmable processor 301 that is coupled to internal memory 302, and to a WWAN transceiver 303 (e.g., a cellular telephone transceiver) which is coupled to an antenna 304. A power supply 308 may be coupled to the processor 301 and other components. In some embodiments, the power supply 308 may include a battery. In a preferred embodiment, the power supply 308 may be electrically connected to a power plug 309 for plugging into a standard utility wall socket. The processor 301 may also be coupled to one or more wired network connection sockets, such as a USB port 310, a FireWire port 311 and/or an Ethernet socket 312. In a simple embodiment, only a single USB port 310 may be provided. In other embodiments, the wireless communication hub device 112 may include multiple USB ports 310, FireWire ports 311, and Ethernet sockets 312 to enable connecting a number of electronic medical and fitness devices via data cables. Providing an optional Ethernet socket 312 within the wireless communication hub device 112 may enable connecting the hub directly to a LAN or local network router. The number of ports may differ among the various embodiments depending upon the physical design of the housing and the particular market or application for which the wireless communication hub device 112 is configured.

In preferred embodiments, the wireless communication hub device 112 may include one or more wireless local area network transceivers for coupling to electronic medical and fitness devices via wireless communication links. For example, the processor 301 may be coupled to a Bluetooth® transceiver 314, which is connected to an antenna 316, and to an IEEE 802.11 (i.e., WiFi) transceiver 322, which is coupled to an antenna 324, for establishing wireless indication links to electronic medical and fitness devices. As described above, a WiFi transceiver 322 may also be connected to the processor 301 for use in coupling the wireless communication hub device 112 to a local area wireless router. Other local wireless transceivers may also be included, such as a Zigbee transceiver (not shown) for coupling to a Zigbee protocol network or an ANT+ transceiver 338 (FIG. 3B) for coupling to an ANT+ protocol network. In some embodiments, the wireless communication hub device 112 may include a global positioning system (GPS) receiver 326 coupled to the processor 301 and to an antenna 328. It should be noted that instead of having multiple antennas 304, 316, 324, 328, the wireless communication hub device 112 may include a single integrated antenna, or two or more transceivers may share a common antenna. Also, in some embodiments, the wireless communication hub device 112 may not include wired network connection sockets (i.e., USB port 310, FireWire port 311 and Ethernet socket 312 are optional), and instead include only one or more wireless local area network transceivers for coupling to electronic medical and fitness devices via wireless communication links.

Since the wireless communication hub device is intended to be simple for users to implement, it may include a very rudimentary user interface. For example, the processor 301 may be coupled to one or more light emitting diodes (LEDs) 334 for communicating status, and to one or more buttons 332 for receiving simple user command inputs (e.g., push to activate or restart).

While FIG. 3A shows the various components of the wireless communication hub device 112 as separate integrated circuits, several components may be integrated into a single very large-scale integrated (VLSI) chip or assembled as an integrated chipset on a single circuit board as is well-known in the art. For example, many modern cellular telephone transceivers, such as the Gobi™ cellular chipset module manufactured by QUALCOMM, Inc., include a powerful processor, transceivers for connecting to WiFi networks and Bluetooth enabled devices, a built-in GPS receiver, and circuitry for connecting to wired connections such as a data port for receiving USB, FireWire and/or Ethernet connections. Thus in an embodiment, the wireless communication hub device 112 may be assembled by configuring a Gobi™ module (or similar cellular transceiver) within a housing 300 with an appropriate power supply 308, one or more antennas 304, one or more LEDs 334, one or more buttons 332, and connections to sockets for receiving USB, Firewire, Ethernet or other wired inputs. Configuring a wireless communication hub device around a sophisticated cellular transceiver module, like the Gobi™ module, can provide 3G cellular, WiFi, and Bluetooth connectivity in a single small package.

The processor 301 within a wireless communication hub device 112 may be configured with processor-executable instructions (which may be stored in memory 302) to enable the processes and communications of the various embodiments described herein. Such software may include the processes required to communicate with a cellular wireless network 130 as well as establishing local networks with electronic medical and fitness devices. Such software may also include a custom protocol for managing communications between the wireless communication hub device 112 and the service platform server 140, as well as with a user's personal computer 138. Such software may also control processes for identifying and communicating with electronic medical and fitness devices even without having a device driver installed on the processor 301, including packaging received data for transmission to the service platform server 140 by "tunneling" via the Internet. Such software may also include processes to minimize the cost of operation or maximize battery life (when implemented in a battery powered configuration) by causing the cellular transceiver to go into an idle mode, and wake up in response to inputs from electronic medical and fitness devices or signals received from a service platform server 140 as described herein. For example, the service platform server 140 may send an SMS message (with or without a message payload) to the communication hub device to prompt it to exit the idle mode and accomplish a predetermined or specified action, such as contacting the service platform server for instructions.

In an embodiment, the wireless communication hub device 112 may enable direct connection to a personal computer 138, such as via a USB port 310 or Ethernet socket 312. In this embodiment, a personal computer 138 may access electronic medical and fitness devices coupled to the wireless communication hub device 112 as though they were connected directly to the computer.

As noted above, the wireless communication hub device 112 may be battery powered, powered by conventional household AC current, or powered by 12 volt DC current from an automobile (e.g., from a cigarette lighter). Thus, the power supply 308 will be configured to receive power from whatever form of external source the device is configured to receive, and configure the power as required by the processor 301 and transceiver circuitry. In battery powered implementations, the power supply 308 may also include circuitry for monitoring the charge of a battery (not shown separately) and providing charging power to the battery when the connector plug 309 is plugged into a power socket. Power supply circuitries which can perform such functions are well-known in the electronic device arts.

The wireless communication hub device 112 may include LEDs 334 that illuminate in different colors, such as a three color LED set which can emit yellow, green and red lights to indicate different status conditions. Such LEDs may be configured to flash or emit continuous light in response to commands from the processor 301.

Figure 3C:
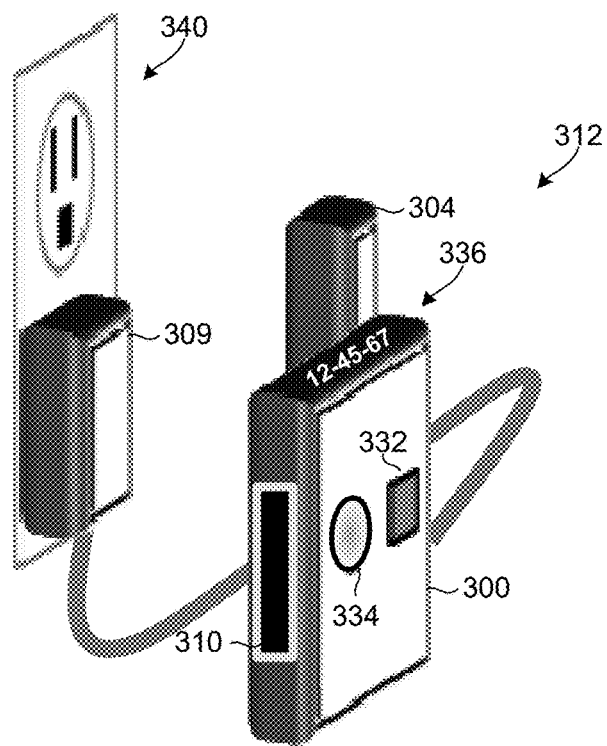
FIGS. 3C and 3D are perspective views of alternative configurations of a wireless communication hub device according to an embodiment.
Figure 3D:
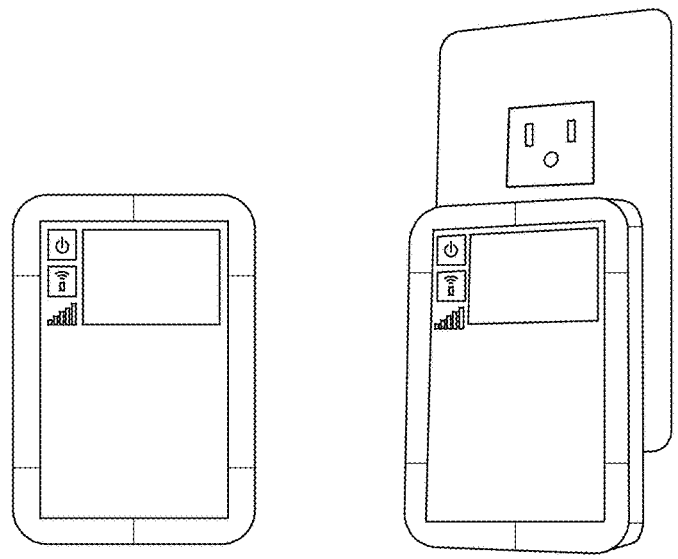

The wireless communication hub device 112 may be configured in a variety of forms. Two examples of a basic small device that plugs into a wall socket are illustrated in FIGS. 3C and 3D. As illustrated, the wireless communication hub device 112 may be packaged within a compact housing 300 that exhibits a multicolor LED 334 and features a single push button 332 and one or more USB ports 310 (and/or other ports/sockets). A unique serial number 336 may be printed on the housing 300 to facilitate registration of the wireless communication hub device 112 with the service platform server 140 as described more fully below. An antenna 304 may be provided as part of the housing 300. An electrical plug 309 may be provided as part of the housing 300 or as a separate module (as shown) that is configured to plug into a standard wall socket 340. In some embodiments, the power supply 308 may be included as part of a module including the plug 309.

Figure 3E:
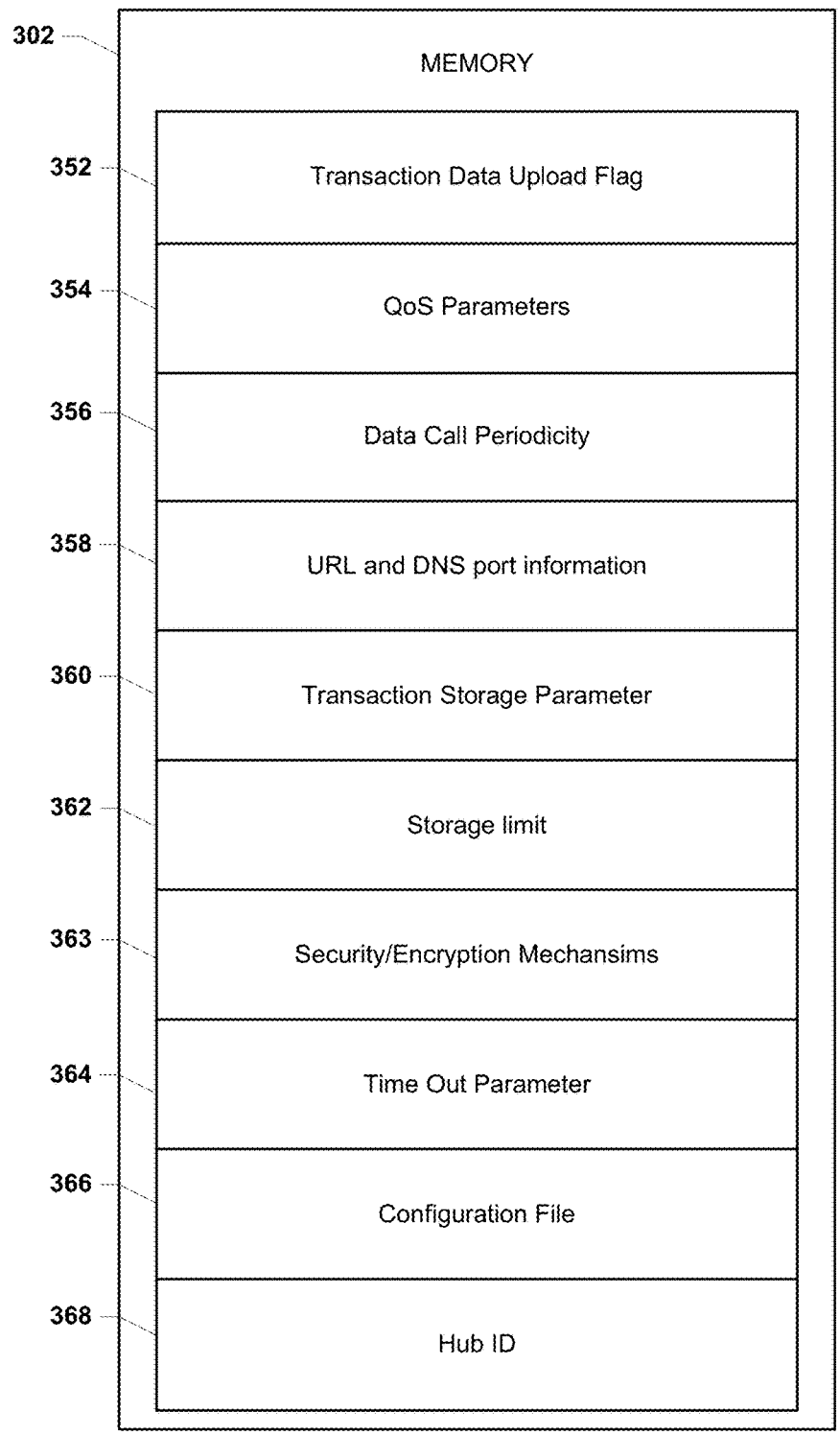
FIG. 3E is a data structure diagram illustrating potential configurability functions and parameters of a wireless communication hub device according to an embodiment.

FIG. 3E is a data structure diagram illustrating potential configurability functions and parameters that may be stored in a memory 302 resident in a wireless communication hub device 112 of the various embodiments. The memory 302 may contain: transaction data upload flags 352, such as a flag indicating if transaction data is to be uploaded off-peak or not; Quality of Service (QoS) parameters, such as minimum QoS levels required before transmitting data; data call periodicity parameters 356, such as a parameter indicating how many times a day the wireless communication hub device should establish a data call with the service platform server and/or a parameter indicating how often keep alive pings should be sent to the service platform server to keep a given communication link open (i.e., alive); URL and DNS port information 358, such as the URL and port for DNS resolution of the service platform server (e.g., www.2net.com/data:56) and/or a backup URL; a transaction storage limit parameter 360, such as a maximum threshold of number of transactions per customer that should be stored on the wireless communication hub device before uploading data to the service platform server; a storage limit 362, such as an amount of transaction data to store (i.e., data size or total number of transactions) and/or a maximum storage capacity; security/encryption mechanisms 363 (e.g., advanced encryption standard (AES) encryption); a time out parameter 364, such as a parameter indicating how long between receiving electronic medical and fitness device data to wait before timing out; a configuration file 366, such as applications or software to support electronic medical and fitness device discovery, pairing, and authentication; and a hub ID 368, such as the wireless communication hub device's identification code (e.g., a six-digit number printed on the housing). In the various embodiments, the memory 302 may contain additional parameters, functions, algorithms, software, and/or controls as necessary to perform the methods and functions discussed herein.

Figure 4A:
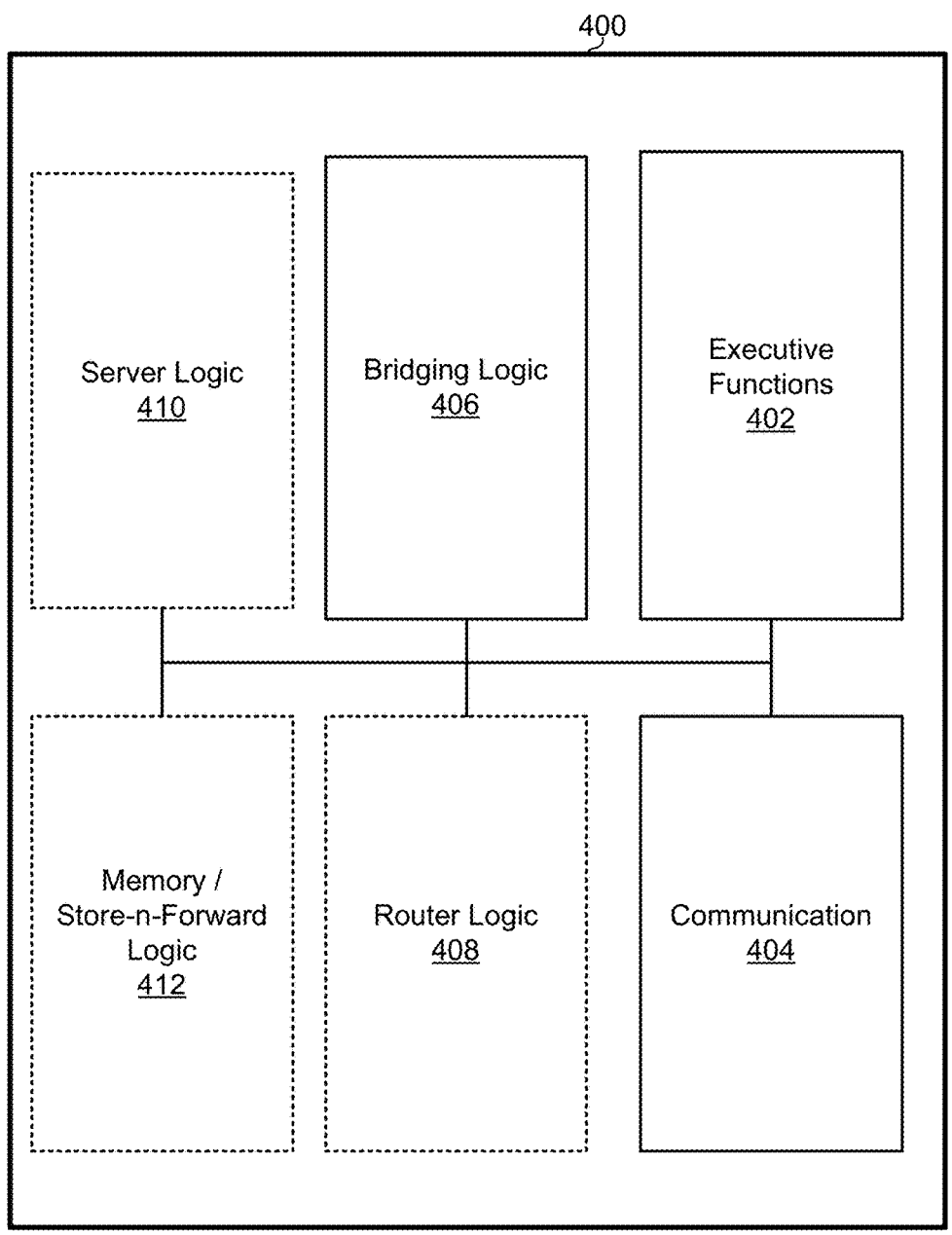
FIGS. 4A and 4B are software/hardware module block diagrams of a wireless communication hub device according to an embodiment.
Figure 4B:
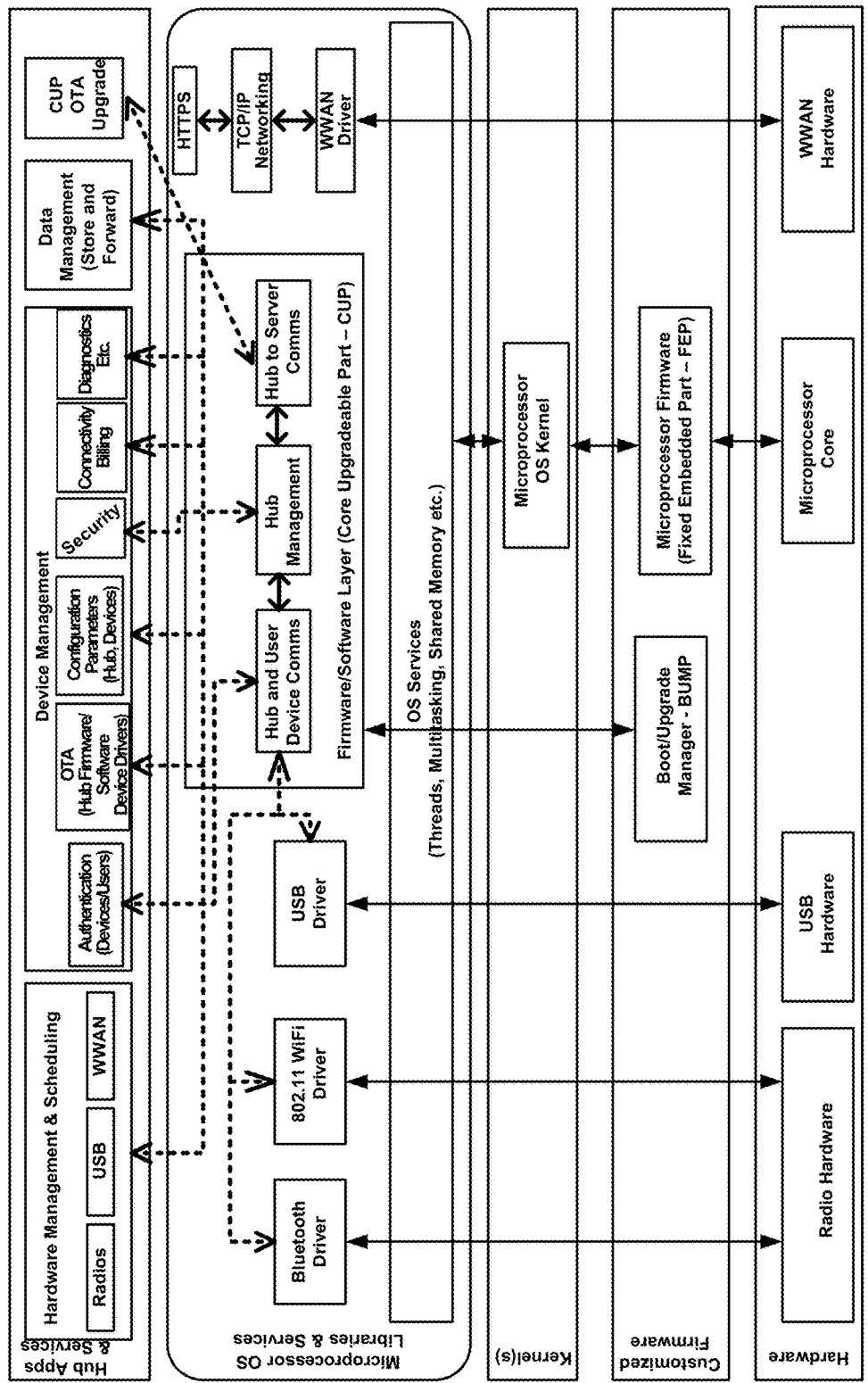

FIGS. 4A and 4B illustrate functional modules that may be implemented within a wireless communication hub device system 400 as software modules, hardware components, or combinations of hardware and software modules. A wireless communication hub device system 400 may include executive functions 402 implemented in a processor 301 which oversee the overall processes and coordinate the other modules. A communication module 404 may include the transceivers and software for operating the transceivers as well as coordinating communication functions with the executive functions 402. The communication module 404 may include the processing necessary to comply with various communication protocols, as well as negotiating communication links, verifying data transmissions, and performing the other common functionality of digital communication systems. A bridging logic module 406 may also be coupled to the executive functions 402 and configured to perform the processes associated with providing a communication link between electronic medical and fitness devices and an external computer, such as the service platform server 140. The bridging logic module 406 may include the logic to package data received from electronic medical and fitness devices into IP packets for tunneling to the service platform server 140, for example. Similarly, the bridging logic module 406 may include the logic to unpack command packets received from the service platform server 140 and provide the embedded commands to the appropriate electronic medical and fitness device.

In various embodiments, the wireless communication hub device system 400 may include additional modules, such as router logic 408 to enable the device to perform typical processes of a conventional router.

Also, the router logic 408 may include algorithms and implement methods for polling connected electronic medical and fitness devices for data according to their respective priority, importance to the user's health, or an order request by the remote server. Also, the wireless communication hub device system 400 may include server logic 410 to enable the device to perform typical processes of a server. Further, embodiments of the wireless communication hub device system 400 may include memory and store-and-forward logic 412 for receiving and storing data from electronic medical and fitness devices and relaying that data at a later time to a destination computer. Router, server and store-and-forward processes and logic are well-known in the computer arts.

FIG. 4B illustrates in more detail relationships and interactions between hardware components and software modules implemented within an example embodiment communication hub device.

Figure 5:
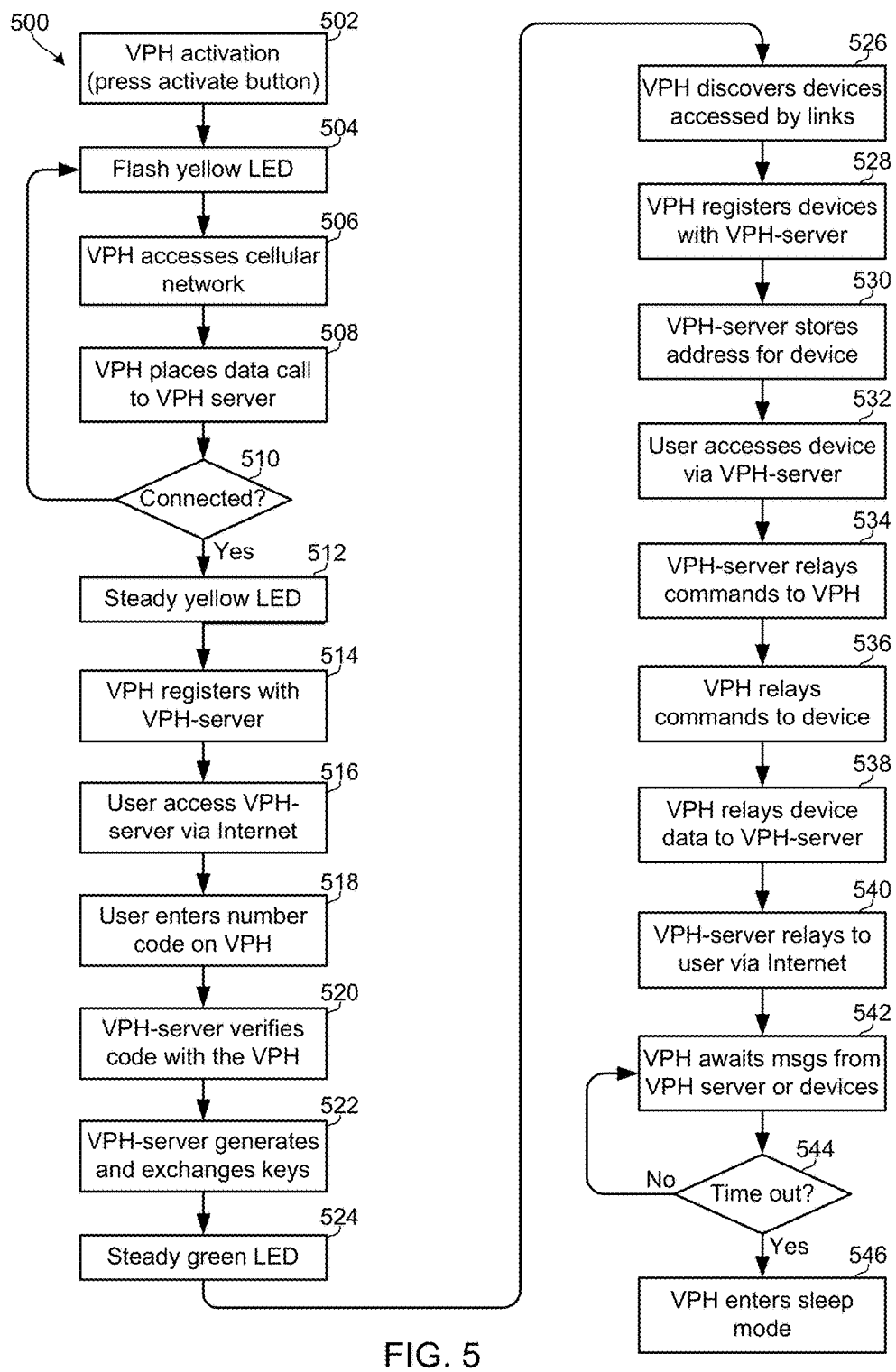
FIG. 5 is a process flow diagram of an embodiment method for initializing and utilizing a wireless communication hub device.

Initial configuration and some of the operations of the wireless communication hub device are illustrated in FIG. 5 as example method 500. A beneficial characteristic of the wireless communication hub device system is simple, fast and reliable setup. To enable simplified setup, the wireless communication hub device 112 may be configured with a single button, which when pushed initiates activation. The wireless communication hub device 112 may also include a code 336 printed on the housing 300. The wireless communication hub device 112 may be pre-configured to establish wireless communication links with a cellular service (e.g., a CDMA, 3G, 4G, etc.) and communicate directly with the service platform server 140 via the Internet 114. After pushing the activation button, a user can access an Internet web site of a service platform server 140 and enter the device's code 336 into a webpage to identify the user as the owner of the wireless communication hub device 112. Thereafter, the service platform server 140 may download any required driver software to the user's computer.

Referring to FIG. 5, at block 502 the wireless communication hub device 112 may initiate the activation process in response to receiving an activation indication (e.g., an indication of a press of the activation button). Alternatively, in some embodiments activation may be initiated when the device is first plugged into a power source, such as a wall socket 340. As activation begins, at block 504 the wireless communication hub device 112 may begin to flash the LED 334. For example, the processor 301 may flash a yellow LED to indicate that the wireless communication hub device 112 is connecting with a cellular network. Simultaneously, at block 506 the wireless communication hub device 112 may attempt to make a connection with a cellular data network. At block 508, once the processor 301 determines that the transceiver 302 has established a connection to a cellular network, the processor 301 may place a data call via the cellular network to the service platform server (i.e., VPH-server) 140. At determination block 510, the processor 301 may monitor the cellular transceiver 302 to determine if a connection has been established with the service platform server 140. As long as the transceiver 302 is in the process of establishing a communication link to the service platform server 140 (i.e., determination 510="No"), the processor 301 continues to flash the yellow LED.

Once the processor 301 determines that a communication link is established with the service platform server 140 (i.e., determination 510="Yes"), at block 510, the processor 301 may apply steady power to the yellow LED (e.g., to indicated that the registration and configuration process is underway). At block 514, at the same time the processor 301 may communicate the identifier of the hub device 112 to the service platform server 140 to identify itself and register with the service platform server 140. The wireless communication hub device 112 may stay in this state for some pre-configured period of time (e.g., 5 minutes). During this time, at block 516 the user may access the service platform server 140 from any computer with a web browser and access to the Internet. At block 518 first time users may set up an account on the service platform server 140 by entering the number printed on the wireless communication hub device 112 along with a user name and password. In an embodiment, the number used to identify a hub device 112 to the service platform server 140 may be a six-digit number. At block 520, the service platform server 140 validates the number entered by the user with the number provided by the hub device 112 during its own online registration. If the user entered code and the code communicated by the wireless communication hub device 112 match, at block 522 the service platform server 140 may generate encryption and authentication keys to be used in future communications with the wireless communication hub device 112 and the user's computer, and transmits those keys to the device and the user's computer to complete the registration process. As part of the registration process the user's computer may download driver software that may be used to communicate with the wireless communication hub device 112 and/or the service platform server 140. Such drivers may be pre-configured to enable secure communications with the specific wireless communication hub device 112 (i.e., the device with the same six-digit number received by the service platform server 140). Also as part of the registration process, the service platform server 140 may download to the wireless communication hub device 112 data and software to support the various functions, such as software updates for the hub device, appropriate peripheral drivers for interfacing with peripheral devices coupled to the hub device, communication look up tables (e.g., updated IP addresses), etc.

Once the registration and configuration process has been completed, at block 524 the processor 301 may illuminate a steady green LED (e.g., to indicate to the user that the hub device 112 is registered with the service platform server 140).

It should be noted that the registration process illustrated in FIG. 5 is but one example of how a wireless communication hub device 112 may be set up and registered with a user account maintained on a service platform server 140. Other mechanisms for registering wireless communication hub devices 112 and correlating them with user accounts maintained on the service platform server 140 may also be implemented. For example, the correlation of the wireless communication hub device 112 (e.g., based upon its six-digit number) with a user account maintained on the service platform server 140 may be accomplished at the point-of-sale of the wireless communication hub device 112. In such an implementation, the user information necessary to identify or set up a user account may be obtained by the cashier or entered by the user into the point-of-sale terminal which transmits that information along with the six-digit code to the service platform server 140. Thus, when the user leaves the store after purchasing a wireless communication hub device 112, the system may be ready to begin services as soon as it is plugged into a wall socket and connected to electronic medical or fitness devices (i.e., peripheral devices).

Referring once again to FIG. 5, once the configuration and registration process is completed, the wireless communication hub device 112 can be moved to any location that has cellular wireless network connectivity. Different electronic medical or fitness devices may be plugged into the wireless communication hub device 112. In an embodiment, the wireless communication hub device 112 may discovery electronic medical or fitness devices plugged into or wirelessly linked to it, step 526. As electronic medical or fitness devices coupled to the wireless communication hub device 112 are identified, the wireless communication hub device 112 may identify the electronic medical or fitness devices to the service platform server 140, step 528, such as by transmitting their media access control (MAC) identifier (ID). The service platform server 140 may store the electronic medical or fitness device identifier in data fields associated with the user or the particular wireless communication hub device 112, step 530. The service platform server 140 may also assign an IPv6 address to each electronic medical or fitness device which also may be stored in the data records of the service platform server 140.

A further feature that may be included in service platform services involves downloading the driver software appropriate for particular electronic medical and fitness devices to a user's computer 138. In this service, the wireless communication hub device 112 informs the service platform server 140 about the connected electronic medical or fitness devices during the registration and device discovery process described above. The service platform server 140 may be configured to store driver software for most electronic medical or fitness devices available in the marketplace, including historical versions of driver software that may be appropriate for older electronic medical or fitness devices. Thus, when the wireless communication hub device 112 identifies the connected electronic medical or fitness devices to the service platform 140, such as by providing MAC IDs of each electronic medical or fitness device, the service platform server 140 may identify the proper driver software stored in its memory or associated database and download the appropriate drivers to a user's computer 138 when the user accesses the service platform server 140. This downloading of driver software may be accomplished when the user first registers with the service platform server 140 or associates a computer 138 with the user's account and a particular wireless communication hub device 112. Also, the service platform server 140 may keep a data record of the MAC IDs of the attached peripheral devices and the driver software that has been downloaded to particular user computers 138. Using such records, the service platform server 140 may determine when a user computer 138 requires a new or updated driver, and download the appropriate driver software when updates are received or when new electronic medical or fitness devices are connected to the wireless communication hub device 112. In this manner, users' computers 138 can be provisioned automatically with the latest driver software required for the electronic medical and fitness devices plugged into the user's wireless communication hub device 112 without having to keep track of the driver software, download the drivers themselves, or bother with the CDs containing driver software that come with electronic medical or fitness devices. Thus, this service platform can help to simplify the user experience of using a variety of electronic medical or fitness devices.

As mentioned above, the wireless communication hub device 112 can support local network operations, such as when a user wishes to connect the wireless communication hub device 112 to their local network by way of an Ethernet or WiFi connection. In such embodiments, the user may provide the relevant information to the service platform server 140 (e.g., by accessing the service platform server 140 via a web browser) which then configures the wireless communication hub device 112 using the entered information. If successful, the wireless communication hub device 112 may leverage the local network to access the Internet 114 and gain access to the service platform server 140 without using a cellular network 130 (e.g., a 3G cellular data network). If a failure occurs in this registration process, the wireless communication hub device 112 may switch back to cellular connectivity and inform the service platform server 140 that the attempt to switch to local connectivity failed. When the wireless communication hub device 112 is connected to a local area network or WiFi network, locally connected computers 138 may directly access the wireless communication hub device 112 and electronic medical and fitness devices coupled to the wireless communication hub device 112. In an embodiment, this may be accomplished using IPv6 addresses provided by the service platform server 140. In an embodiment, additional computers 138 may connect to the wireless communication hub device 112 provided they have been granted access to the wireless communication hub device 112 by the user who performed the initial setup.

FIG. 5 also illustrates some normal operation processes that may be conducted once the wireless communication hub device 112 has been registered with the service platform server 140. For example, a user may request access to an electronic medical or fitness device from a personal computer 138 by accessing the service platform server 140, step 532. This may be accomplished by the user accessing the service platform server 140 via the Internet 114 from any computer 138 hosting a web browser. Upon accessing a service platform server 140 webpage, the user may be prompted to enter a username and password (or some other form of user/account identification and verification). When the user is verified, the service platform server 140 may present a menu (e.g., in the form of an HTTP webpage) of peripheral devices coupled to the wireless communication hub device 112, and accept a data request or configuration command for a particular electronic medical or fitness device from the user's computer 138. When this data request or command is received, the service platform server 140 may relay the data request or command to the wireless communication hub device, step 534. In some cases, the request for data from a user's computer 138 may require the wireless communication hub device 140 to use a driver for the particular electronic medical or fitness device in order to format the data request or command so that it can be received and processed by the electronic medical or fitness device. In this manner, a user may be able to access a particular electronic medical or fitness device (e.g., a webcam, heart rate monitor, pedometer, etc) from any computer 138 with Internet access, including computers 138 that are not equipped with the appropriate device driver software. The wireless communication hub device 112 receives the data request or commands from the server platform server 140 and relays them on to the particular electronic medical or fitness device, step 536. In some cases the data request or command may be encapsulated within IP packets with the packet payload including the data request or command in the format required by the device driver as formatted by the service platform server 140. In such cases, the wireless communication hub device 112 unpacks the data request or command and relays it to the electronic medical or fitness device via the wired or wireless connection established with the electronic medical or fitness device.

If an electronic medical or fitness device provides data for communication to the service platform server 140 or a user computer 138 (such as may occur in response to a data request messages discussed above), such data is received by the hub device 112 and relayed to the service platform server 140, step 538. In some cases, the wireless communication hub device 112 may encapsulate the device data within IP packets so that the data can be tunneled through the Internet 114 for processing by the service platform server 140 using an appropriate driver software. As described above, the data messages may be transmitted to the Internet address of the service platform server 140 via a cellular or local area network connection to the Internet 114. Electronic medical or fitness device data packets are received by the service platform server 140, processed if necessary, and relayed to a user computer 138 (if appropriate) via the Internet 114, step 540.

When not actively responding to a data request or relaying data from an electronic medical or fitness device, the wireless communication hub device 112 may await messages from the service platform server 140 or a computer 138 coupled to the wireless communication hub device or to a local area network, step 542. To minimize costs associated with maintaining a data connection via a cellular data network, the wireless communication hub device 112 may be configured to terminate an active data connection when activity ceases for a predetermined amount of time ("timeout interval"). Thus, the processor 301 of the wireless communication hub device 112 may be configured to determine whether the timeout interval has transpired since a last communication event, determination 544. If the timeout interval has not expired (i.e., determination 544="No"), the wireless communication hub device 112 may continue to monitor the open cellular data communication link for messages from the service platform server 140. Once the timeout interval has expired (i.e., determination 544="Yes"), the wireless communication hub device 112 may terminate the open cellular data communication link and enter a "sleep" mode, step 546. In embodiments in which the wireless communication hub device 112 is plugged into an inexhaustible power supply, such as an AC wall socket, the sleep mode may involve terminating the open cellular data communication link but continuing to monitor messages or telephone calls placed to the telephone number of the wireless communication hub device 112. For example, as described more fully below with reference to FIG. 8A, the wireless communication hub device 112 may be configured to receive a simple message service (SMS) message during the sleep mode which prompts the wireless communication hub device 112 to place a data call to the service platform server 140 and initiate a new data communication link. In embodiments in which the wireless communication hub device 112 is battery powered, the sleep mode may further entail reducing processing performed on the wireless communication hub device in order to economize battery consumption.

Another example method for activating the wireless communication hub device 112 and associating it with a user wireless communication hub device account may take advantage of location information from a GPS receiver that may be included in the device itself. In this implementation, when the wireless communication hub device 112 is activated, such as by being plugged into a wall outlet, the device determines its location from its GPS receiver 326. Upon establishing a communication link with the service platform server 140, the wireless communication hub device 112 may inform the server of its identification code (e.g., the six-digit number printed on the housing) along with its precise latitude and longitude coordinates. Using this coordinate information, the service platform server 140 can identify the user from public information, such as a residential address determined based upon the map coordinates from a map including address information, and then associate the wireless communication hub device 112 with a user account having the same residential address.

Figure 23:
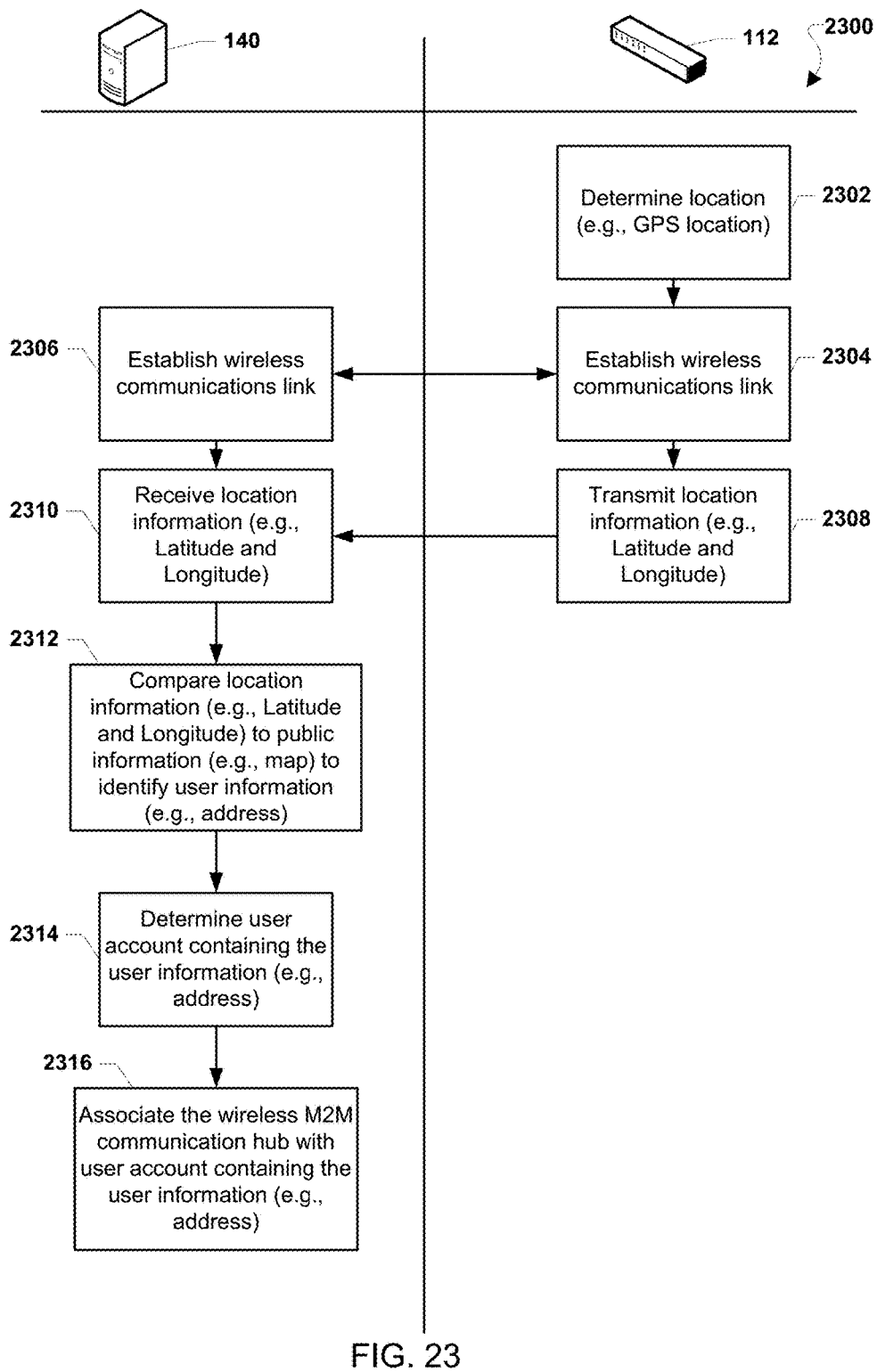
FIG. 23 is a process flow diagram illustrating an embodiment method for associating a wireless communication hub device based on location information.

FIG. 23 illustrates an embodiment method 2300 for associating a wireless communication hub device 112 with a service platform server 140 taking advantage of location information received from the wireless communication hub device 112. In an embodiment, the wireless communication hub device 112 may include a GPS receiver 326 enabling the wireless communication hub device 112 to determine its location. At block 2302 the wireless communication hub device 112 may determine its location. As an example, the wireless communication hub device 112 may utilize its GPS receiver 326 to determine the latitude and longitude at which the wireless communication hub device 112 may be located. At blocks 2304 and 2306 the wireless communication hub device 112 and service platform server 140 may establish a wireless communications link with each other. In an embodiment, in establishing the wireless link, or after establishing the wireless link, the wireless communication hub device 112 may transmit its identification code (e.g., the six-digit number printed on the housing) to the service platform server 140. At block 2308 the wireless communication hub device 112 may transmit the location information (e.g., the latitude and longitude) to the service platform server 140. At block 2310 the service platform server 140 may receive the location information (e.g., the latitude and longitude), and at block 2312 the service platform server 140 may compare the location information (e.g., the latitude and longitude) to public information to identify user information. In an embodiment, the service platform server 140 may compare the latitude and longitude to a map to determine a residential address (i.e., user information) corresponding to that latitude and longitude. At block 2314 the service platform server 140 may determine a user account containing the user information. In an embodiment, the service platform server 140 may search a database of user accounts to identify a user account with an address matching the address found using the received latitude and longitude. At block 2316 the service platform server 140 may associate the wireless M2M hub with the user account containing the user information (e.g., address).

Once the configuration and registration process is completed, the wireless communication hub device 112 can be moved to any location that has cellular wireless network connectivity. Different electronic medical and fitness devices can be plugged into the wireless communication hub device 112. In an embodiment the wireless communication hub device 112 may discovery electronic medical and fitness devices plugged into or wirelessly linked to it. As electronic medical and fitness devices coupled to the wireless communication hub device 112 are identified, the wireless communication hub device 112 may identify them to the service platform server 140, such as by transmitting their media access control (MAC) identifier (ID). The service platform server 140 may store the electronic medical and fitness device identifier in data fields associated with the user or the particular wireless communication hub device 112. The service platform server 140 may also assign an IPv6 address to each electronic medical and fitness device which also may be stored in the data records.

A further feature that may be included in service platform services involves downloading the driver software appropriate for particular electronic medical and fitness devices to a user's computer 138. In this service, the wireless communication hub device 112 informs the service platform server 140 about the connected electronic medical and fitness devices during the registration and device discovery process described above. The service platform server 140 may be configured to store driver software for most electronic medical and fitness devices available in the marketplace, including historical versions of driver software that may be appropriate for older electronic medical and fitness devices. Thus, when the wireless communication hub device 112 identifies the connected electronic medical and fitness devices to the service platform server 140, such as by providing MAC IDs of each electronic medical and fitness device, the server can identify the proper driver software stored in its memory or associated database and download the appropriate drivers to a user's computer 138 when the user accesses the server. This downloading of driver software may be accomplished when the user first registers with the service platform server 140 or associates a computer 138 with the user's account and a particular wireless M2M communication 112. Also, the service platform server 140 may keep a data record of the MAC IDs of the attached electronic medical and fitness devices and the driver software that has been downloaded to particular user computers. Using such records, the service platform server 140 may determine when a user computer 138 requires a new or updated driver, and download the appropriate driver software when updates are received or when new electronic medical and fitness devices are connected to the wireless communication hub device 112. In this manner, users' computers 138 can be provisioned automatically with the latest driver software required for the electronic medical and fitness devices plugged into their wireless communication hub device 112 without having to keep track of the driver software, download the drivers themselves, or bother with the CDs containing driver software that come with electronic medical and fitness devices. Thus, this service platform service can help to simplify the user experience of using a variety of electronic medical and fitness devices.

Figure 20:
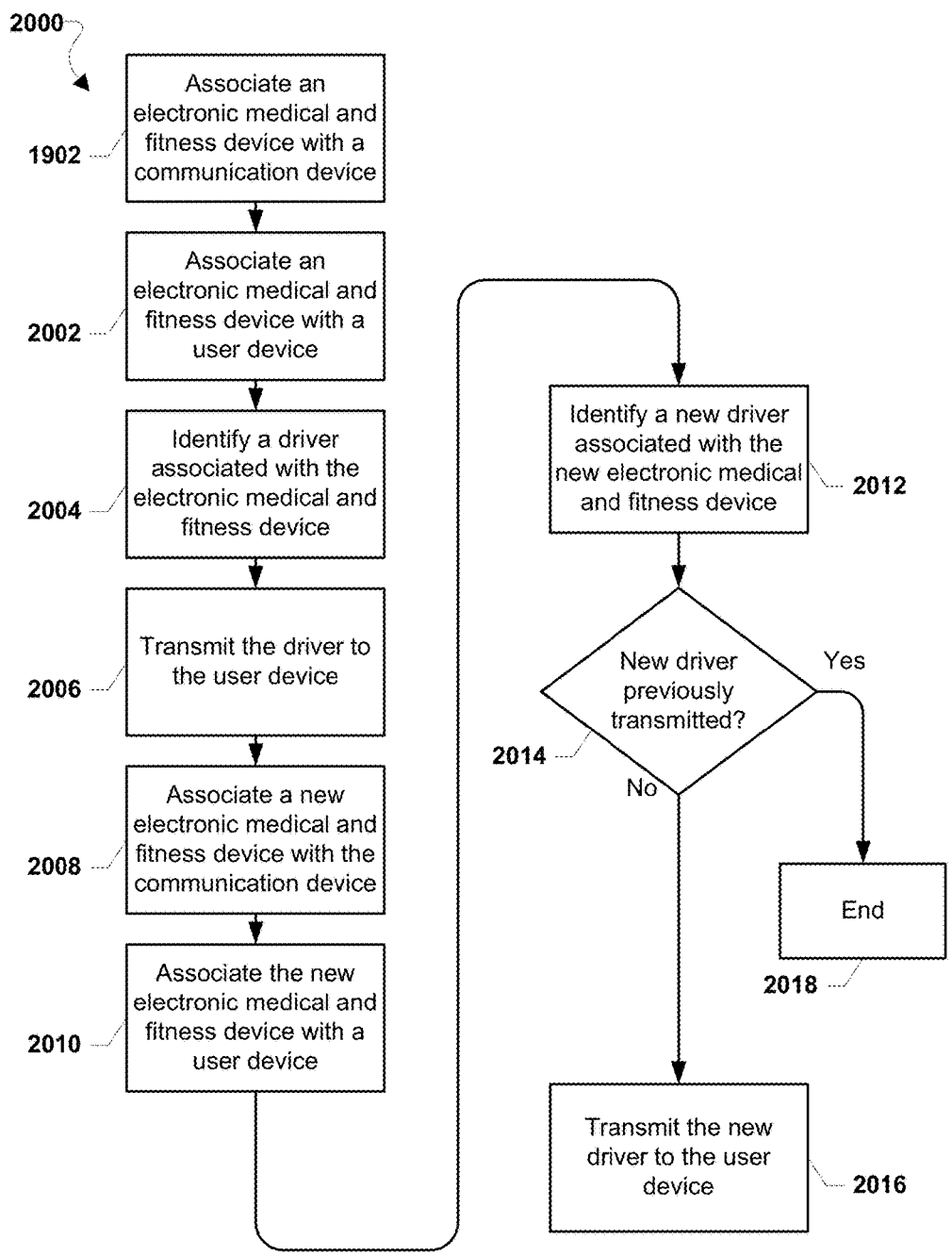
FIG. 20 is a process flow diagram illustrating an embodiment method for downloading driver software modules.

FIG. 20 illustrates an embodiment method 2000 for downloading driver software appropriate for a particular electronic medical and fitness device 102 to a user device (such as a user's computer 138). As discussed above, at block 1902 the service platform server 140 may associate an electronic medical and fitness device 102 with a communication hub device (such as the wireless communication hub device 112). At block 2002 the service platform server 140 may associate an electronic medical and fitness device with a user device (e.g., user computer 138). At block 2004 the service platform server 140 may identify a driver associated with the electronic medical and fitness device 102. At block 2006 the service platform server 140 may transmit the driver to the user device (e.g., user computer 138). In this manner, the appropriate drivers for the medical and fitness device may be downloaded to the user computer 138 without the user needing to keep track of the driver software, download the driver themselves, or bother with physical media, such as CDs, containing the driver software.

At block 2008 the service platform server 140 may associate a new electronic medical and fitness device 102 with the communication hub device (such as the wireless communication hub device 112), and at block 2010 the service platform server 140 may associate the new electronic medical and fitness device 102 with a user device. At block 2102 the service platform server 140 may identify a new driver associated with the new electronic medical and fitness device 102. At determination block 2014 the service platform server 140 may determine if the new driver has been previously transmitted to the user device (e.g., user computer 138). In an embodiment, the service platform server 140 may maintain a list of drivers transmitted to and/or already stored on a user computer 138, and may compare the new driver to that list to determine if the new driver has been previously transmitted to the user computer 138. If the new driver has not been previously transmitted (i.e., determination block 2014="No"), at block 2016 the service platform server 140 may transmit the new driver to the user device (e.g., user computer 138). If the new driver has been previously transmitted (i.e., determination block 2014="Yes"), at block 2018 the method 2000 may end. In this manner, the service platform server 140 may download the appropriate driver software when new electronic medical and fitness devices are connected to the wireless communication hub device 112.

Figure 21:
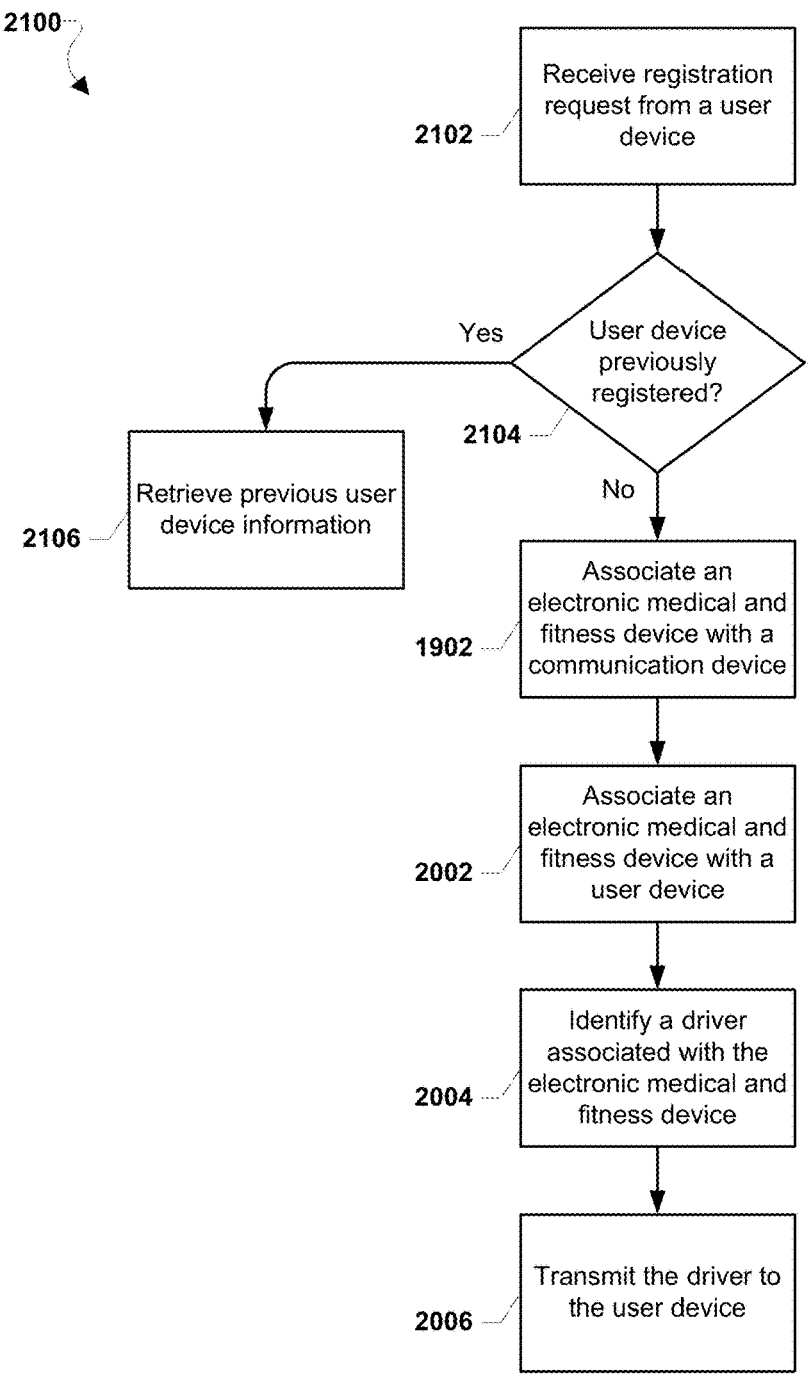
FIG. 21 is a process flow diagram illustrating another embodiment method for downloading driver software modules.

FIG. 21 illustrates an embodiment method 2100 that may be used in conjunction with method 2000 discussed above with reference to FIG. 20 to download appropriate driver software to a user device (e.g., user computer 138). At block 2102 the service platform server 140 may receive a registration request from a user device (e.g., user computer 138). In an embodiment, a registration request may be sent from the user device (e.g., user computer 138) when the user first attempts to connect with the service platform server 140. In an alternative embodiment, a registration request may be sent each time the user device (e.g., user computer 138) attempts to establish a connection with the service platform server 140. At determination block 2104 the service platform server 140 may determine if the user device (e.g., user computer 138) has previously registered with the service platform server 140. If the user device (e.g., user computer 138) had previously registered (i.e., determination block 2104="Yes"), at block 2106 the service platform server 140 may retrieve the previous user device information from memory 302. If the user device (e.g., user computer 138) had not previously registered (i.e., determination block 2104="No"), as discussed above, at block 1902 the service platform server 140 may associate an electronic medical and fitness device 102 with a communication device (such as the wireless communication hub device 112). At block 2002 the service platform server 140 may associate an electronic medical and fitness device with a user device (e.g., user computer 138). At block 2004 the service platform server 140 may identify a driver associated with the electronic medical and fitness device 102. At block 2006 the service platform server 140 may transmit the driver to the user device (e.g., user computer 138).

Figure 22:
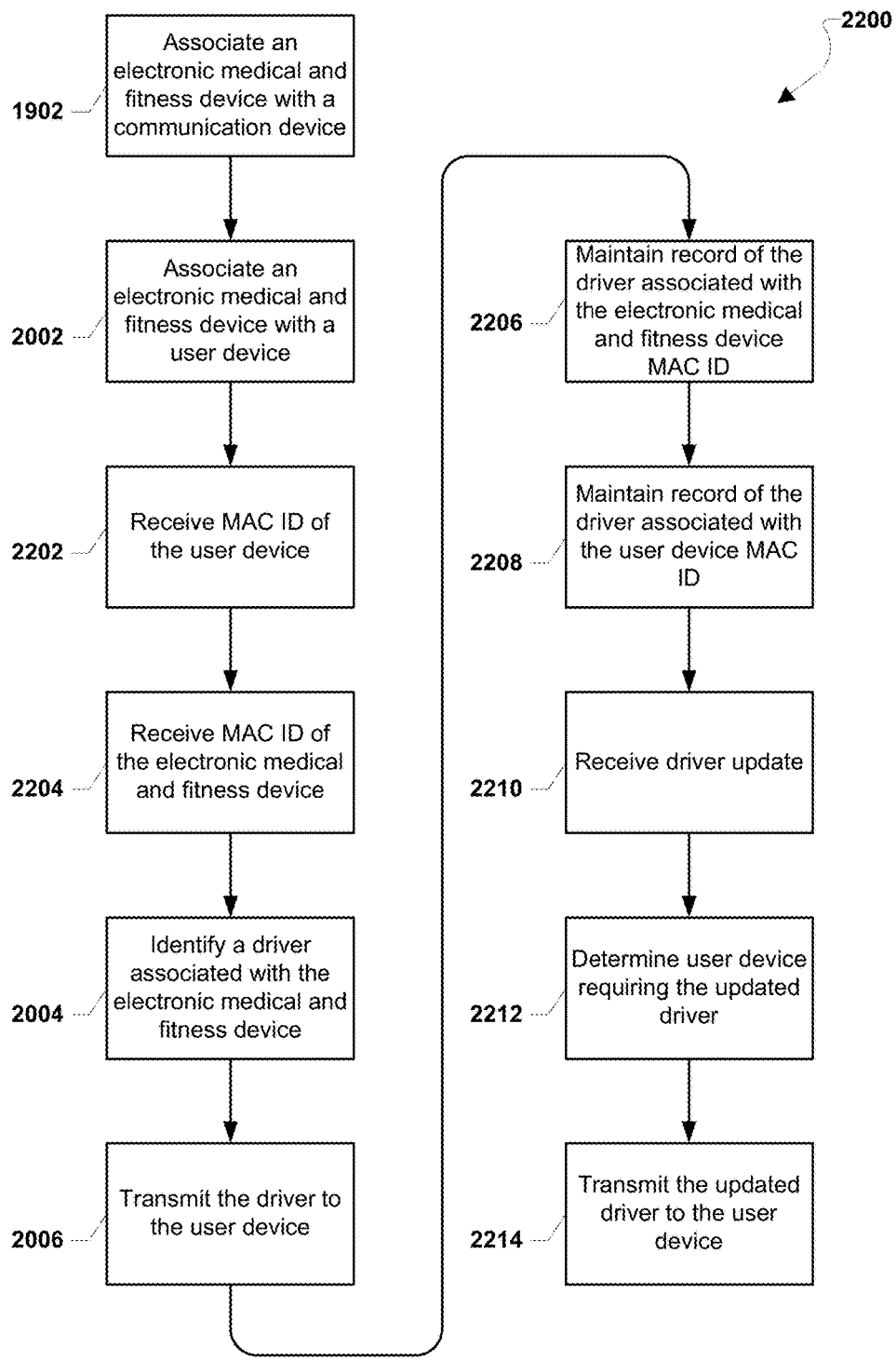
FIG. 22 is a process flow diagram illustrating a third embodiment method for downloading driver software modules.

FIG. 22 illustrates an embodiment method 2200 that may be used in conjunction with method 2000 discussed above with reference to FIG. 20 to update driver software. As discussed above, at block 1902 the service platform server 140 may associate an electronic medical and fitness device 102 with a communication device (such as the wireless communication hub device 112). At block 2002 the service platform server 140 may associate an electronic medical and fitness device with a user device (e.g., user computer 138). At block 2202 the service platform server 140 may receive a MAC ID for the user device (e.g., user computer 138). At block 2204 the service platform server 140 may receive a MAC ID for the electronic medical and fitness device 102. In an embodiment, the MAC ID for the electronic medical and fitness device 102 may be provided by the wireless communication hub device 112. As discussed above, at block 2004 the service platform server 140 may identify a driver associated with the electronic medical and fitness device 102. At block 2006 the service platform server 140 may transmit the driver to the user device (e.g., user computer 138). At block 2206 the service platform may maintain a record of the driver associated with the electronic medical and fitness device 102 MAC ID. In an embodiment, the record may be a table of MAC IDs and their associated drivers stored in a memory. At block 2208 the service platform may maintain a record of the driver associated with user device (e.g., user computer 138) MAC ID. In an embodiment, the record may be a table of MAC IDs and their associated drivers stored in a memory. In a further embodiment, a combined table of MAC IDs for both electronic medical and fitness devices 102, user devices (e.g., user computer 138), and individual users (e.g., a user account) may be stored in the memory of the service platform server 140.

At block 2210 the service platform server 140 may receive an indication that the driver has been updated. At block 2212 the service platform server 140 may determine the user device (e.g., user computer 138) that may require an updated driver. In an embodiment, the service platform server 140 may determine the user device requiring the updated driver using, at least in part, the record of the driver associated with the user device (e.g., user computer 138) MAC ID and/or the record of the electronic medical and fitness device 102 MAC ID. At block 2214 the service platform server 140 may transmit the updated driver to the user device. In this manner the appropriate drivers may be provided to the user computer 138 when updates are received.

If an electronic medical and fitness device provides data for communication to the service platform server 140 or a user computer 138 (such as may occur in response to a data request messages discussed above), such data is received by the wireless communication hub device 112 and relayed to the service platform server 140. In some cases, the wireless communication hub device 112 may encapsulate the device data within IP packets so that the data can be tunneled through the Internet for processing by the service platform server 140 using an appropriate driver software. As described above, the data messages are transmitted to the Internet address of the service platform server 140 via a cellular or local area network connection to the Internet 114. Device data packets are received by the service platform server 140, processed if necessary, and relayed to other computers/servers via the Internet 114.

Figure 6A:
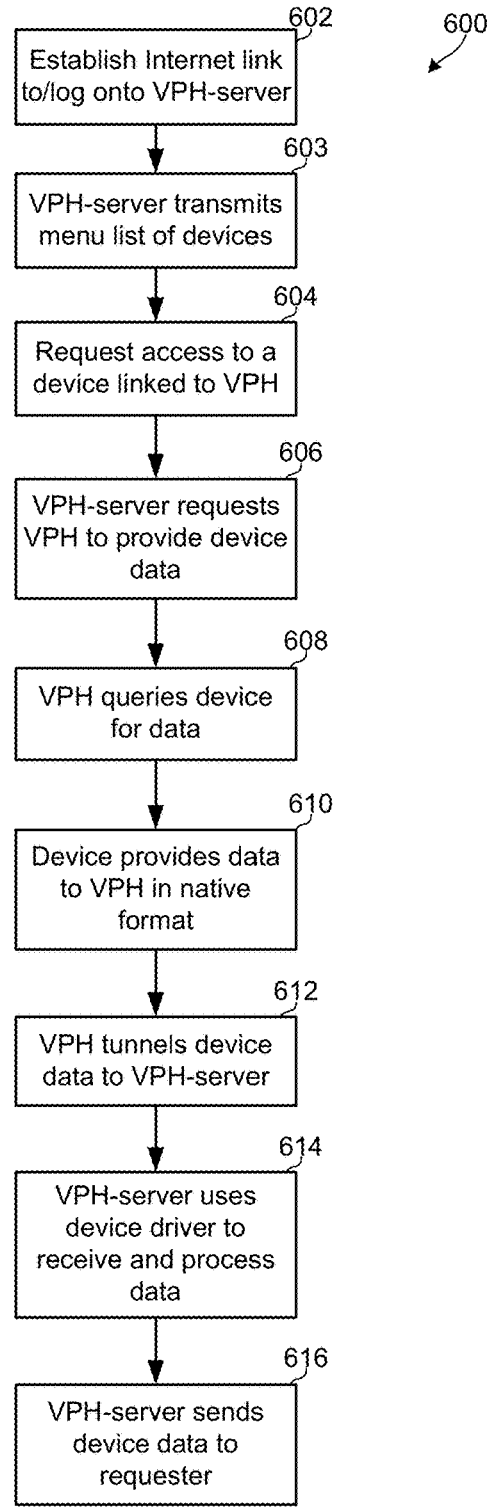
FIGS. 6A and 6B are process flow diagrams illustrating embodiment methods for tunneling data and commands to and from electronic medical and fitness devices.

As mentioned above, the wireless communication hub device 112 and the service platform server 140 may be configured to communicate data in a format that does not require the wireless communication hub device processor 301 to run a device driver for any electronic medical and fitness device. FIG. 6A illustrates an example method 600 for tunneling data and commands to and from electronic medical and fitness devices via the Internet. In the example method 600, a user may access the Internet from any computer, such as from a web kiosk computer, and access the service platform server 140 at its URL, step 602. After the user is identified and verified to the service platform server 140, service platform server 140 may generate a webpage listing a menu of electronic medical and fitness devices coupled to the wireless communication hub device 112, step 603. The user may then request access to a particular electronic medical and fitness device, 102, 104, 108 (e.g., such as a webcam to check on the user's house), step 604. This request may be accomplished, for example, by the user selecting an electronic medical or fitness device 102, 104, 108 hyperlink (e.g., a webcam hyperlink) on the menu list of available electronic medical and fitness devices listed in a webpage generated by the service platform server 140. For example, hyperlinks may be configured so that double-clicking on a webcam hyperlink in the electronic medical and fitness device menu may transmit a device access request to the service platform server 140, or transmit a code that the service platform server 140 will recognize as such.

In response to receiving a device or data access request from a user, the service platform server 140 may transmit a suitable request message to the wireless communication hub device 112 to obtain the access or data requested by the user, step 606. Upon receiving this request, the wireless communication hub device 112 may query the indicated electronic medical or fitness device for the requested data, step 608. In response, the queried electronic medical or fitness device may begin providing the requested data in its native format (i.e., in a format that requires a device driver to receive), step 610. For example, if the request is for images from an electronic medical or fitness device 102 (e.g., a webcam or blood pressure monitor), the wireless communication hub device 112 may signal the electronic medical or fitness device 102 (e.g., a webcam or blood pressure monitor) to activate and begin transmitting image data to the wireless communication hub device 112. In this embodiment, the wireless communication hub device 112 receives the native format electronic medical or fitness device data and packages the data into IP packets that can be tunneled via the Internet 114 to the service platform server 140, step 612. Methods and protocols for tunneling data via the Internet 114 are well-known in the computer communication arts.

The service platform server 140 may receive message packets from the wireless communication hub device 112, unpack the electronic medical or fitness device data from the tunneling IP packets, and use the appropriate driver software to process the received electronic medical or fitness device data, step 614. The service platform server 140 may then transmit the requested data on to the requester's computer 138 via the Internet 114 using standard IP formats, such as in the form of a webpage or video feed, step 616. Thus, in the example of a user requesting access to video images from a webcam coupled to the wireless communication hub device 112, the user may receive a video feed presented on a web browser without having to load the webcam driver software onto the computer 138.

Figure 6B:
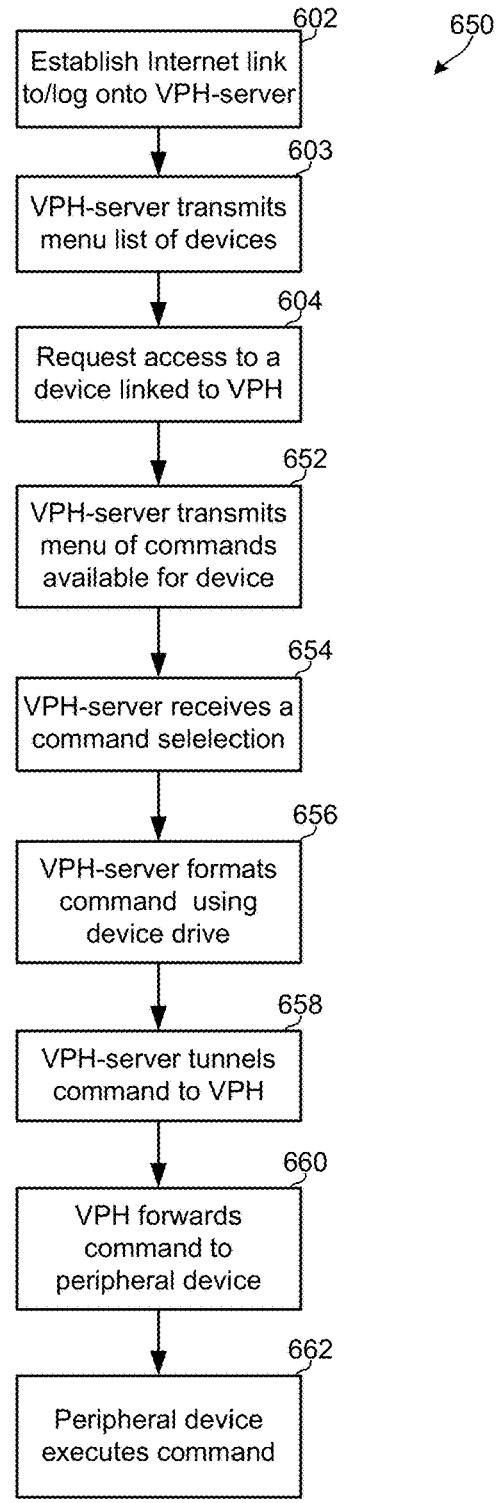

The tunneling of data and commands may also proceed from a user's computer via the service platform server 140 to the wireless communication hub device 112. For example, a user may be able to operate or configure an electronic medical and fitness device from a web kiosk computer (i.e., a computer that does not is not equipped with the appropriate device driver) using the service platform services. FIG. 6B illustrates an embodiment method 650 for tunneling command messages to an electronic medical and fitness device via the wireless communication hub device 112 similar to method 600 described above with reference to FIG. 6A except the data and commands may proceed from a user's computer 138. As described above, at block 602 a user may access the Internet from any computer, such as from a web kiosk computer, and access the service platform server 140 at its URL. After the user is identified and verified to the service platform server 140, as described above, at block 603, the service platform server 140 may generate a webpage listing a menu of electronic medical and fitness devices coupled to the wireless communication hub device 112. As described above, at block 603 the user may then request access to a particular electronic medical and fitness device 104 (e.g., such as a security system to remotely set a particular alarm state). This request may be accomplished by the user selecting a hyperlink on the menu list of available electronic medical and fitness devices listed in a webpage generated by the service platform server 140. For example, double-clicking on a security system hyperlink in the electronic medical and fitness device menu may be configured as a device access request that is transmitted to the service platform server 140. If the selected device will accept user commands, the service platform server 140 may transmit a webpage presenting a menu of the commands available for the selected electronic medical and fitness device, step 652. The user may select a particular command, such as by clicking on a hyperlink associated with the command description, the user can signal the service platform server 140 to send the corresponding command to the selected electronic medical and fitness device via the wireless communication hub device 112. Upon receiving such a command request, step 654, the service platform server 140 may format the requested command using the appropriate device driver software, step 656, and encapsulate the command within IP message packets so that it will be tunneled through the Internet 114 to the wireless communication hub device 112, step 658. Upon receiving such IP packets, the wireless communication hub device 112 unpacks the command data and transmits the command packets to the addressed electronic medical and fitness device, step 660. The electronic medical and fitness device receives and executes the command as if it had been provided directly by a computer linked to the device and configured with the appropriate device driver, step 662.

Figure 7A:
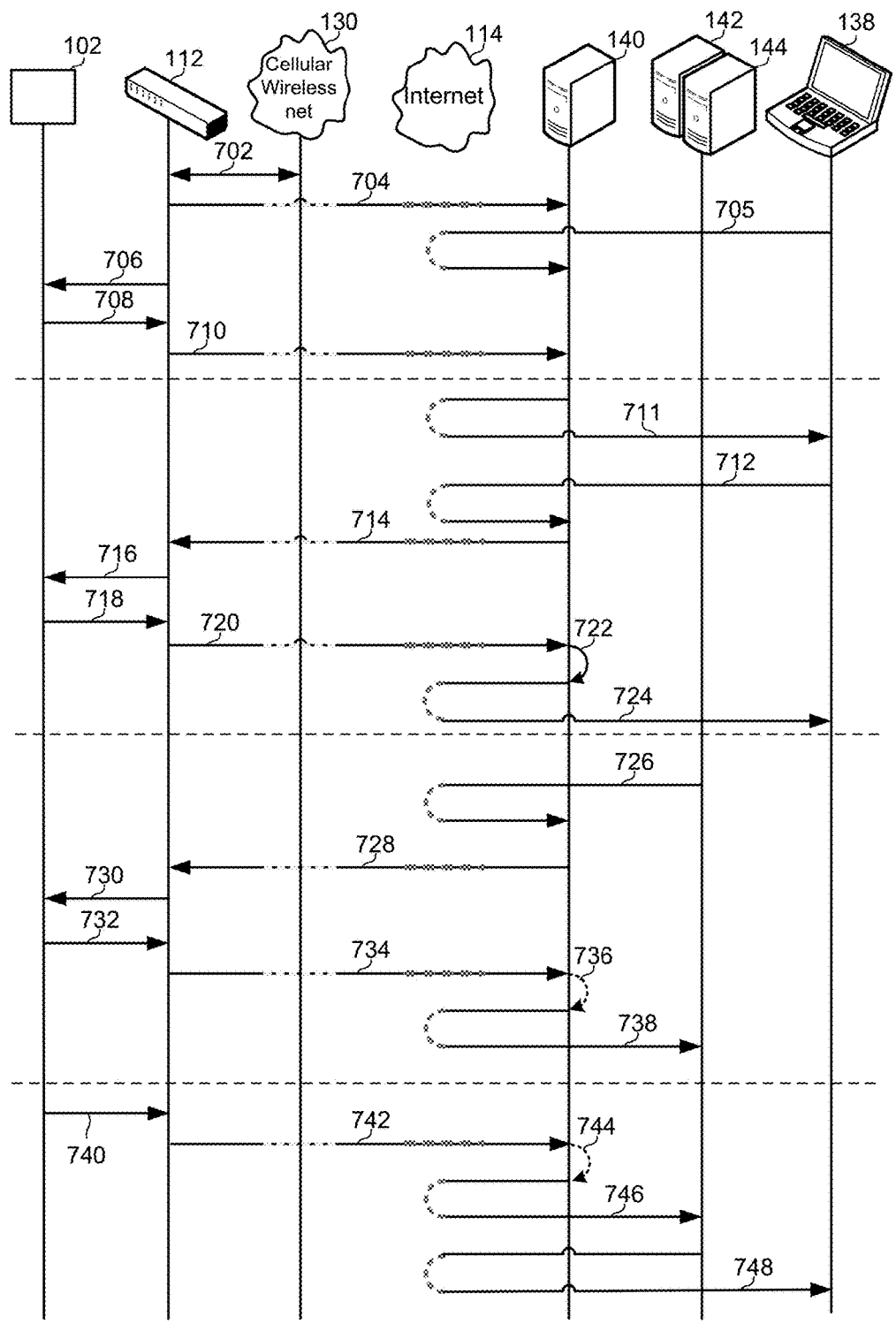
FIGS. 7A and 7B are message flow diagrams illustrating messages that may be exchanged among various components during various operations of an embodiment wireless communication hub device.
Figure 7B:
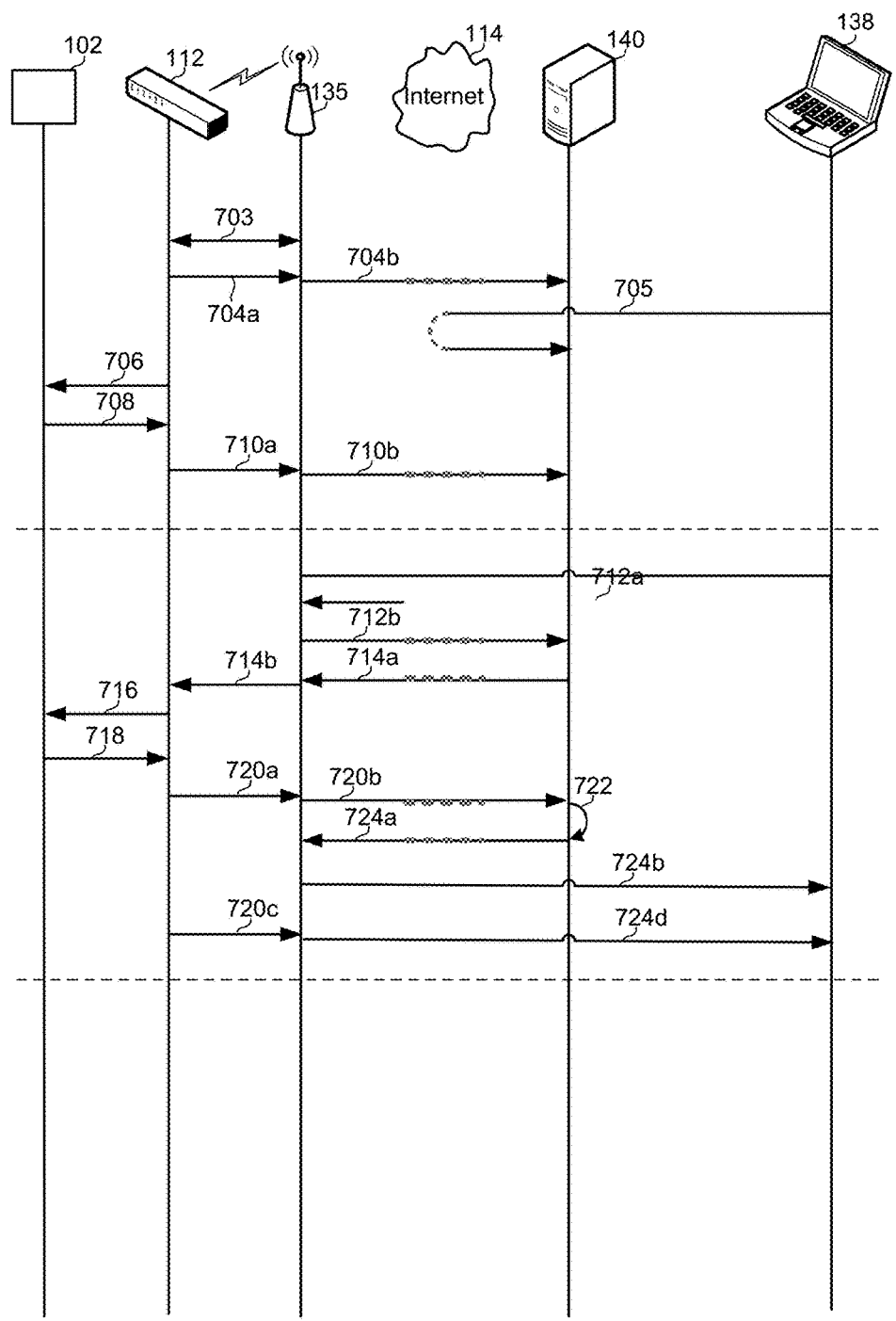

Example message flows the may be implemented in the various embodiment methods are illustrative in FIGS. 7A and 7B. Referring to FIG. 7A, when the wireless communication hub device 112 is activated, such as when it is plugged into a wall socket and the user presses the initiation button, the device may exchange the network signaling messages 702 necessary to establish a cellular data communication link with a cellular wireless network 130. Once connected to the cellular wireless network 130, the wireless communication hub device 112 may establish a data call to the service platform server 140 and transmit the device's identifier, message 704. As described above, the wireless communication hub device 112 may signal to a user when a connection is made to the service platform server 140, such as by displaying a steady yellow light, at which point the user may log into the service platform server 140 via the Internet 114 and enter registration information (e.g., as the six-digit number on the housing of the wireless communication hub device), message 705. Once the wireless communication hub device 112 is registered with the service platform server 140, it may discover the electronic medical and fitness devices 102 coupled to it, such as by transmitting device discovery messages 706 and receiving device reply messages 708. Device discovery and reply message formats are well-established in networking protocols, such as the Bluetooth® protocol. As the wireless communication hub device 112 identifies attached electronic medical and fitness devices, it may transmit information regarding them, such as their MAC ID, to the service platform server 140, message 710.

Once the registration process is completed, a user may access an electronic medical and fitness device 102 from a computer 138 by logging on to the service platform server 140. As discussed above, the service platform server 140 may send a webpage to the browser of the user's computer 138 presenting a menu of electronic medical and fitness devices 102 that may be accessed, message 711. Using such a menu or a direct command, the user may request access to a particular electronic medical and fitness device by sending an access request message 712 to the service platform server 140 via the Internet 114. In response to receiving this message, the service platform server 140 may transmit an appropriate data request message 714 over the open data communication link with the wireless communication hub device 112 via the Internet 114 and the cellular wireless network 130. The wireless communication hub device 112 relays the data request message 716 to the selected electronic medical and fitness device 102. Data generated in response to the request may be transmitted from the electronic medical and fitness device 102 to the wireless communication hub device 112 via the established cable or wireless communication link, message 718. The wireless communication hub device then relays the data, such as in an encapsulated IP packet, to the service platform server 140 over the open data communication link via the cellular wireless network 130 and the Internet 114, message 720. The service platform server 140 may unpack the device data and process it using the appropriate device driver software, processing 722, and forward the data on to the requesting computer 138 via the Internet 114, message 724.

As mentioned above, other data users, such as medical establishments or device manufacturers, may request data from electronic medical and fitness devices coupled to the wireless communication hub device 112. To do so, a third-party server 142, 144 controlled by the data user may transmit a data request message via the Internet 114 to the service platform server 140, message 726. If the service platform server 140 does not have the requested data in memory, it may transmit a data request message 728 to the wireless communication hub device 112. The wireless communication hub device 112 relays the data request message 730 to the selected electronic medical and fitness device 102. Data generated in response to the request may be transmitted from the electronic medical and fitness device 102 to the wireless communication hub device 112 via the established cable or wireless communication link, message 732. The wireless communication hub device then relays the data, such as in an encapsulated IP packet, to the service platform server 140 over the open data communication link via the cellular wireless network 130 and the Internet 114, message 734. The service platform server 140 may unpack the device data and process it using the appropriate device driver software, optional processing 736, and forward the data on to the requesting server 142, 144 via the Internet 114, message 738. In situations where the service platform server 140 does not possess the device driver for the particular electronic medical and fitness device, such as when the data requester controls device drivers, the service platform server 140 may simply relay the encapsulated device data without processing.

The service platform services may be configured to deliver data generated by an electronic medical and fitness device 102 without receiving a data request message. For example, a electronic medical and fitness device 102, such as a home security system, may generate a data message 740 that is transmitted to the wireless communication hub device 112 by an establish communication link (e.g., a USB or FireWire cable or local wireless communication link). In response to receiving such a data message 740, the wireless communication hub device 112 may place a data call to the service platform server 140 and transmit the data via the cellular wireless network 130 and the Internet 114, message 742. The service platform server 140 may unpack the device data and process it using the appropriate device driver software, optional processing 744, and forward the data on to the appropriate destination computer, such as a third-party server 142, 144 via the Internet 114 in message 746, or to a user computer 138 via the Internet 114 in message 748. In situations where the service platform server 140 does not possess the device driver for the particular electronic medical and fitness device, such as when the data generating electronic medical and fitness device is controlled by the manufacturer, the service platform server 140 may simply relayed the encapsulated device data without processing.

As mentioned above, the wireless communication hub device 112 may also be configured to communicate with the service platform server 140 via a connection to the Internet 114 through a local wireless router. Example messages that may be transmitted among various components in such a communication system are illustrated in FIG. 7B. For example, during the registration and configuration process described above with reference to FIG. 5, the wireless communication hub device 112 may discover that it can gain access to the Internet 114 via a wireless router. In that case, the wireless communication hub device 112 may establish a wireless communication link with the router in an exchange of messages 703 as provided for in the wireless protocol implemented by the router. Once connected to the router, the wireless communication hub device 112 may transmit its identification number (e.g., a unique six-digit) to the service platform server 140 via the wireless router, message 704a, which may relay the message via the Internet 114, message 704b. Similarly, the wireless communication hub device 112 may transmit information about attached electronic medical and fitness devices 102 in a wireless message 710a to the wireless router which may relay the message via the Internet 114 to the service platform server 140, message 710b. Other like numbered messages may be exchanged in the manner described above with reference to FIG. 7A.

FIG. 7B also illustrates message flows of communications between a user's personal computer 138, the wireless communication hub device 112 and electronic medical and fitness devices 102 when a local wireless router 135 is available. When a user's personal computer 138 is coupled to the local wireless router 135, it may log in to the service platform server 140 with an access message 712a sent to the local wireless router 135. The local wireless router 135 may relay the access message from the personal computer 138 to the service platform server 140 via the Internet 114, message 712b. Messages from the service platform server 140 to the wireless communication hub device 112 may be communicated via the Internet 114 to the local wireless router 135, messages 714a, which may relay them to the wireless communication hub device 112, messages 714b. Similarly, messages relaying data from electronic medical and fitness devices 102 may be transmitted from the wireless communication hub device 112 to the local wireless router 135, messages 720a, which routes them onto the service platform server 140 via the Internet 114, messages 720b. The service platform server 140 may process the data, processing 722, and forward the data on to the personal computer 138 by transmitting data messages via the Internet 114 to the wireless router, message 724a, which relays the messages to the personal computer 138, message 724b. As mentioned above, the wireless communication hub device 112 may also be configured to communicate directly with the personal computer 138 via a local network. Thus, messages from the wireless communication hub device 112 may be sent to the personal computer 138 via the local wireless router 135, message 720c, which may relay the messages directly to the personal computer 138, message 724d.

In an embodiment, the wireless communication hub device 112 may be configured to send and receive messages via a cellular communication network.

As described above, the wireless communication hub device 112 may be configured to enter an idle or "sleep mode" when there are no active interactions with electronic medical and fitness devices or with the service platform server 140. The purpose of such a sleep mode may be to minimize the operating cost of the wireless communication hub device, such as by minimizing cellular wireless network access charges when no active data communications are taking place. In such an implementation, the service platform server 140 may be configured to send a message to the wireless communication hub device 112 to "wake it up" when there is a need to communicate with the electronic medical and fitness devices. An example method 800 for accomplishing this is illustrated in FIG. 8A and example messages that may be exchanged in the process are illustrated in FIG. 8B.

Figure 8A:
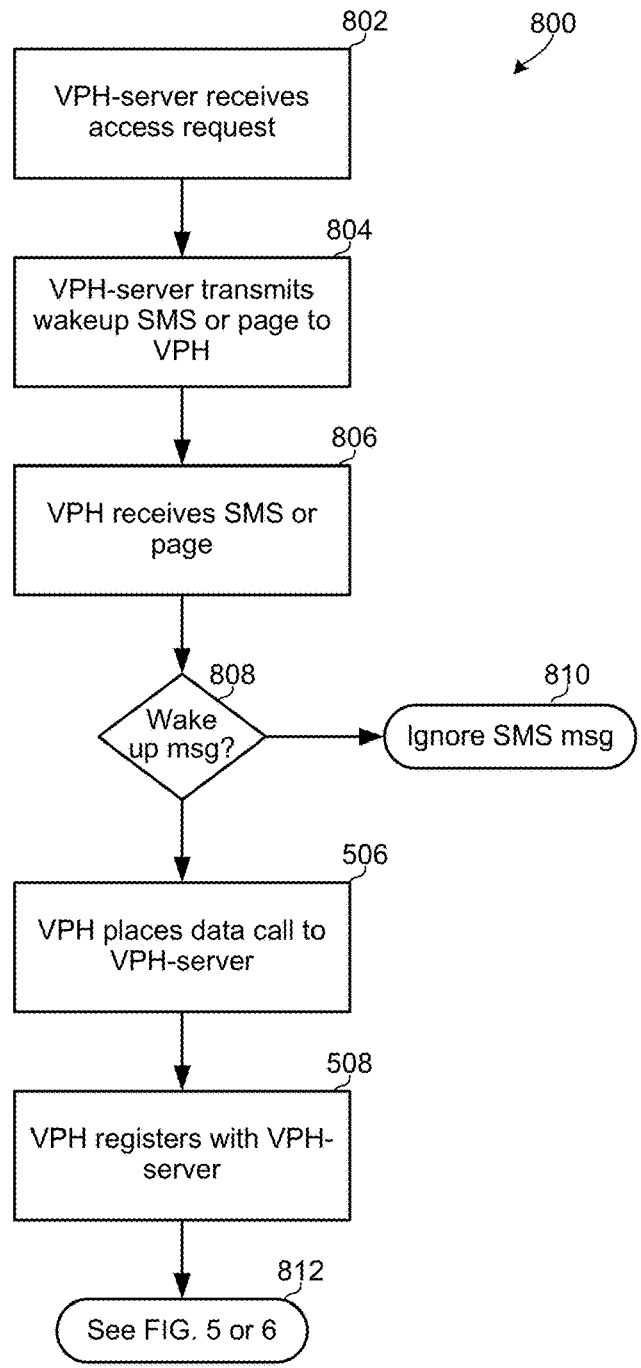
FIG. 8A is a process flow diagram of an embodiment method for activating a wireless communication hub device.
Figure 8B:
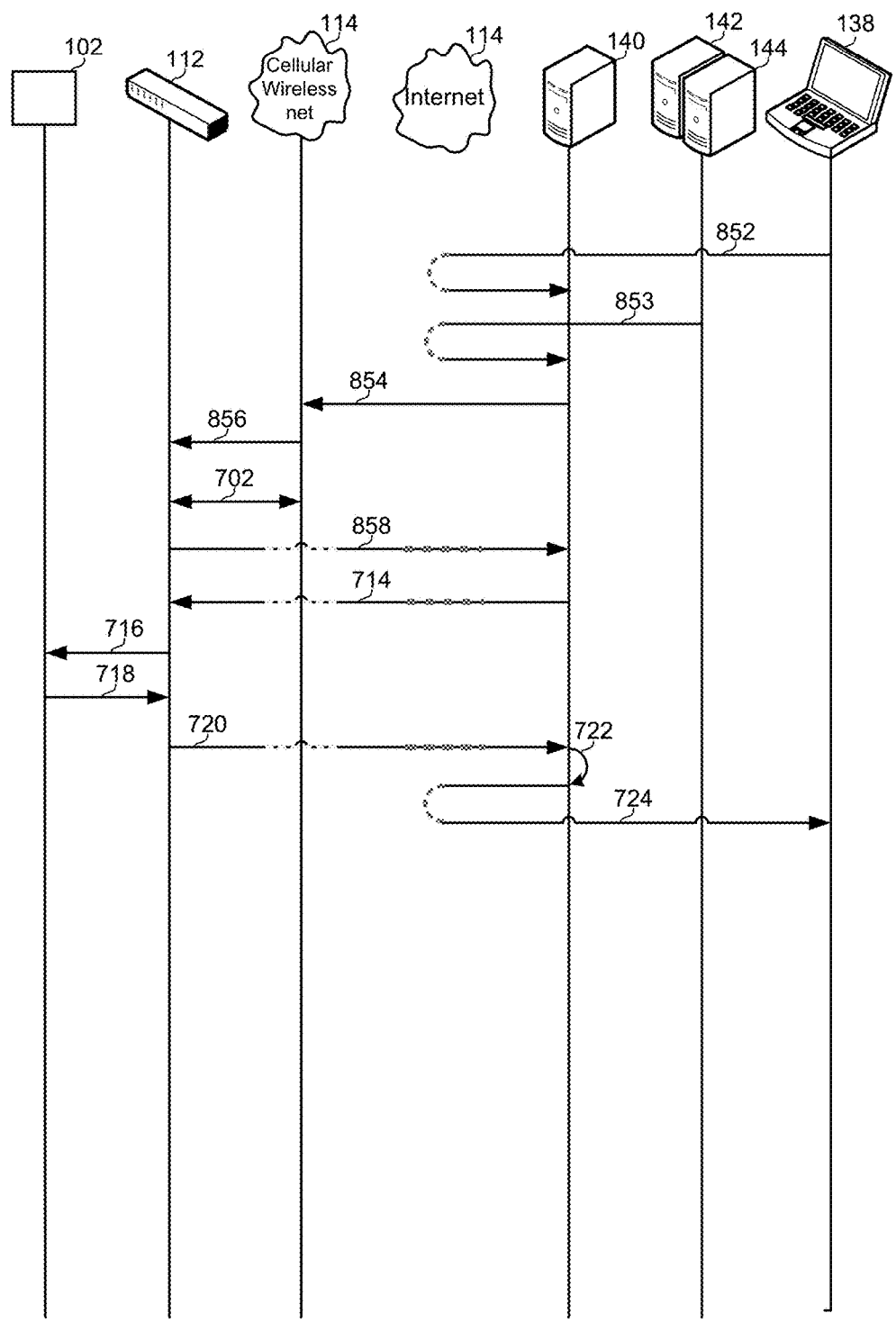
FIG. 8B is a message flow diagram illustrating messages that may be exchanged among various communication network participants during the embodiment method illustrated in FIG. 8A.

Referring to FIGS. 8A (for steps) and 8B (for messages), when the service platform server receives a request for data or access to a particular electronic medical and fitness device coupled to a wireless communication hub device 112, step 802 and messages 852, 853, the service platform server may transmit a wake-up message to the wireless communication hub device 112, step 804. Such a wake-up message may be transmitted as an SMS message which may be sent by conventional means to the cellular wireless network 130, message 854, which may deliver the message like a conventional SMS message, message 856. Such an SMS message may be addressed to a telephone number assigned to the wireless communication hub device 112 and include data or codes which the wireless communication hub device can recognize as constituting a wake-up message. In an embodiment, reception of an SMS without any message payload (i.e., no included data or codes) may prompt the communication hub device 112 to wake-up. Alternatively, the service platform server 140 may send a paging-type message to the wireless communication hub device 112 which may be configured with a paging receiver.

When the wireless communication hub device 112 receives the SMS or page message, step 806, the device processor 301 may parse the received message to determine whether it includes a code indicating that the wireless communication hub device 112 should wake-up, determination 808. If the received message does not include the appropriate "wakeup code" (i.e., determination 808="No"), the processor 301 may simply ignore the received message, step 810. This test of the received code can guard against inadvertent activations of the wireless communication hub device 112, such as when a message is improperly routed or a wrong number is dialed.

If the processor 301 determines that the received message includes the appropriate "wakeup code" (i.e., determination 808="Yes"), and in embodiments in which the device is configured to wake up in response to receiving a payload-less SMS message, the wireless communication hub device 112 may activate its cellular transceiver 303 to exchange the network signaling messages 702 necessary to establish a cellular data communication link with a cellular wireless network 130. If a local wireless router 135 with access to the Internet 114 is available, the wireless communication hub device 112 may negotiate a communication link with the wireless router instead. Once connected to the cellular wireless network 130 (or a local wireless router 135), the wireless communication hub device 112 may place a data call to the service platform server 140, step 506. When a connection to the service platform server 140 is established (or as part of establishing the connection), the wireless communication hub device may provide its unique identifier to the server, thereby identifying itself, step 508 and message 858. With a communication link established between the wireless communication hub device 112 and the service platform server 140, the server and devices may proceed with communications as described above with reference to FIGS. 5, 6A, 6B and 7A, step 812.

Additional methods for activating a computing device such as the wireless communication hub device are disclosed in U.S. patent application Ser. No. 12/430,642 entitled "Apparatus and Method for Activating Computer Applications with SMS Messaging" filed Apr. 27, 2009, the entire contents of which are hereby incorporated by reference.

Figure 17:
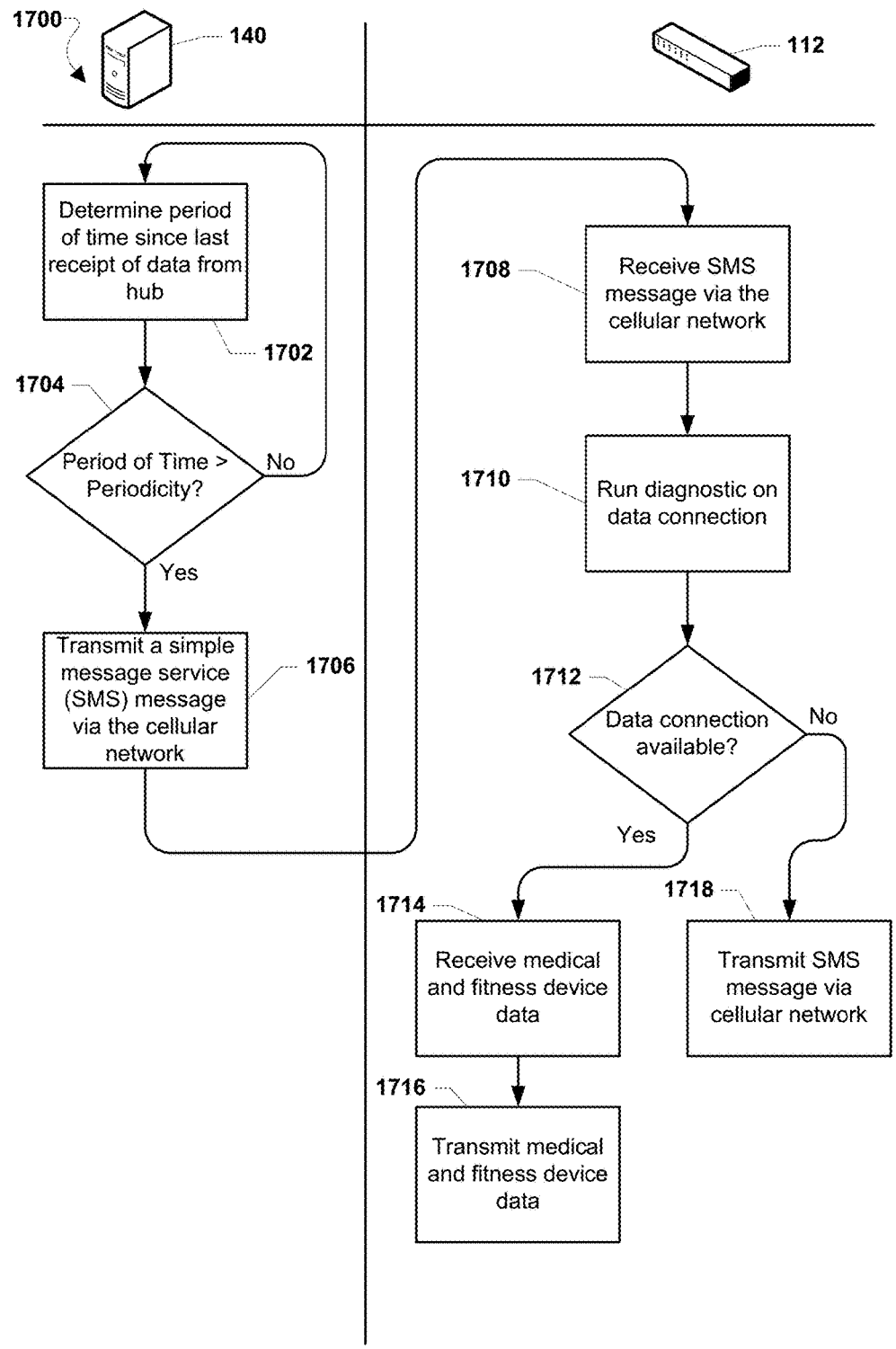
FIG. 17 is a process flow diagram illustrating an embodiment method for interacting with a wireless communication hub device via an SMS message.

FIG. 17 illustrates an embodiment method 1700 for transmitting a simple message service message (SMS) message from a service platform server 140 to the wireless communication hub device 112. At block 1702 the service platform server 140 may determine the period of time that has expires since the service platform server 140 last received data from the wireless communication hub device 112. The period of time may be determined in any manner, such as by comparing a time stamp in the last received data communication to a current clock time at the service platform server 140. At determination block 1704 the service platform server 140 may determine if the period of time is greater than a periodicity for which data should be received from the wireless communication hub device 112. The periodicity may be any amount of time, such as 10 minutes, or 30 minutes, and may be fixed value based on communication protocol requirements, or service platform server 140 operator settings. In an embodiment, the periodicity may be a value stored in a memory accessible by the service platform server 140. If the period of time is not greater than the periodicity (i.e., determination block 1704="No"), at block 1702 the service platform server 140 may determine the period of time that has expires since the service platform server 140 last received data from the wireless communication hub device 112. If the period of time is greater than the periodicity (i.e., determination block 1704="Yes") at block 1706 the service platform server 140 may transmit an SMS message via the cellular wireless network to the wireless communication hub device 112. At block 1708 the wireless communication hub device 112 may receive the SMS message via the cellular wireless network. In an embodiment, the SMS message may be a payload-less SMS message. In an alternative embodiment, the SMS message may have a payload.

At block 1710 the wireless communication hub device 112 may run a diagnostic of the data connection between the wireless communication hub device 112 and the service platform server 140. In an embodiment, the diagnostic may be run in response to an indication in the received SMS message, such as a command in the payload of an SMS message, or such as the originating phone number in a payload-less SMS message.

In another embodiment, the wireless communication hub device 112 may be configured with processor-executable instructions to perform operations to run a diagnostic on the data connection in response to any received SMS messages. In a further embodiment, the wireless communication hub 112 may be configured with processor-executable instructions to perform operations to contact another server to receive one of instructions, configuration changes, and software updates in response to any received SMS messages. In a further embodiment, the wireless communication hub 112 may be configured with processor-executable instructions to perform operations to transmit a log of data traffic transmitted from and/or received by the wireless communication hub device 112 to the service platform server 140 in response to any received SMS messages. In a further embodiment, the wireless communication hub device 112 may be configured with processor-executable instructions to perform operations to contact the service platform server 140 to report an operating condition of the wireless communication hub device 112 and/or any electronic medical or fitness device 102 in response to any received SMS messages. In a further embodiment, the wireless communication hub device 112 may be configured with processor-executable instructions to perform operations for authenticating the electronic medical or fitness device 102 and/or re-authenticating the wireless communication hub device 112 to the service platform server 140 in response to any received SMS messages. In a further embodiment, the wireless communication hub device 112 may be configured with processor-executable instructions to perform operations for verifying security settings to the service platform server 140 in response to any received SMS messages.

At determination block 1712 the wireless communication hub device 112 may determine if the data connection with the service platform server 140 is available. In an embodiment, the determination that the data connection is available may be made based on the diagnostic run at block 1710 or may be determined based on a connection test. If the data connection is available (i.e., determination block 1712="Yes"), at block 1714 the wireless communication hub device 112 may receive medical and fitness device data, such as medical and fitness device data from the medical and fitness device 102. At block 1716, the wireless communication hub device 112 may transmit the medical and fitness device data to the service platform server 140. If the data connection is not available (i.e., determination block 1712="No"), at block 1718 the wireless communication hub device 112 may transmit an SMS message via the cellular wireless network to the service platform server 140. In an embodiment, the SMS message may include a payload, for example diagnostic results. In another embodiment, the SMS message may include medical and fitness device data.

Figure 9A:
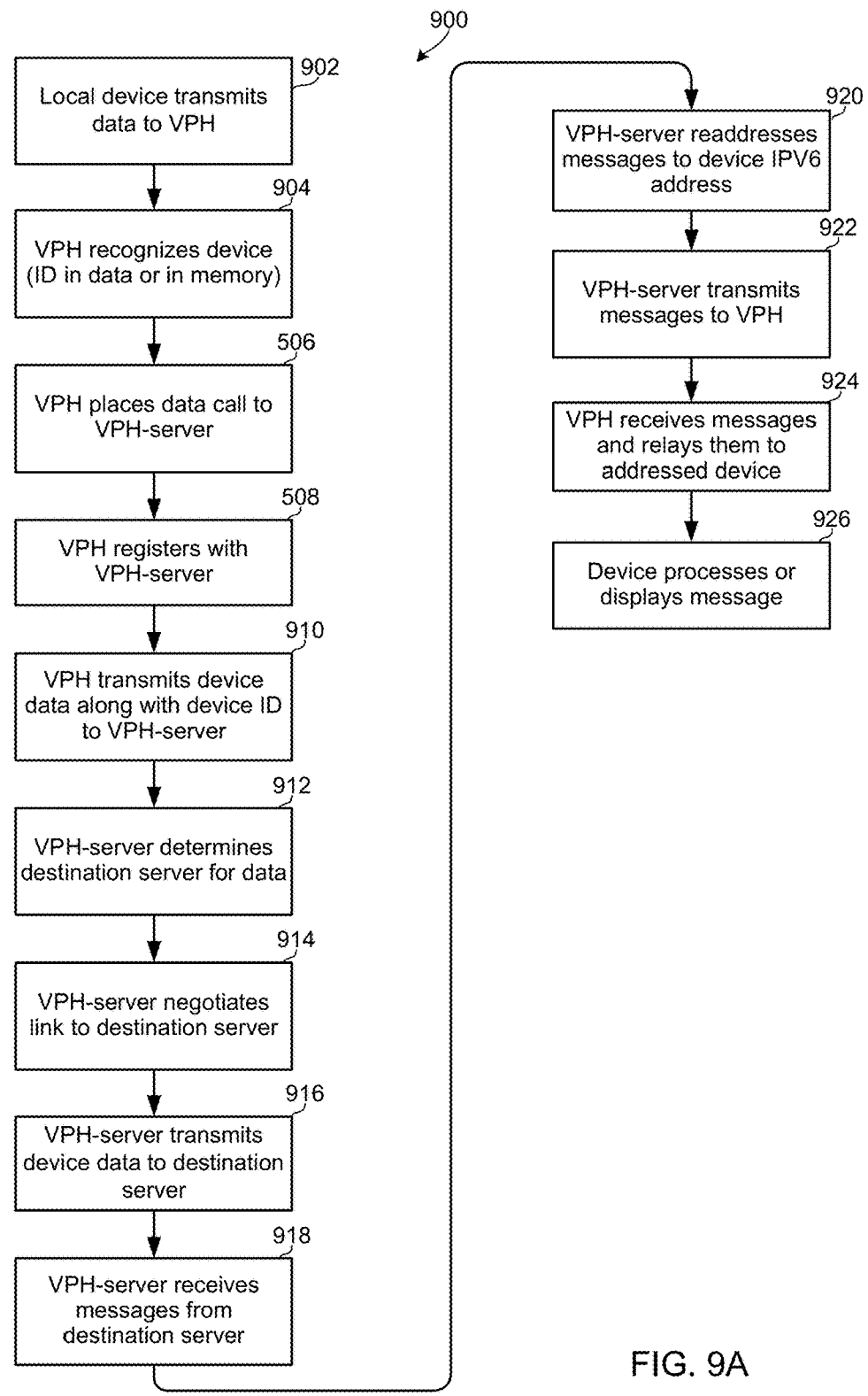
FIG. 9A is a process flow diagram of an embodiment method implemented in a wireless communication hub device for reporting data received from an electronic medical or fitness device.
Figure 9B:
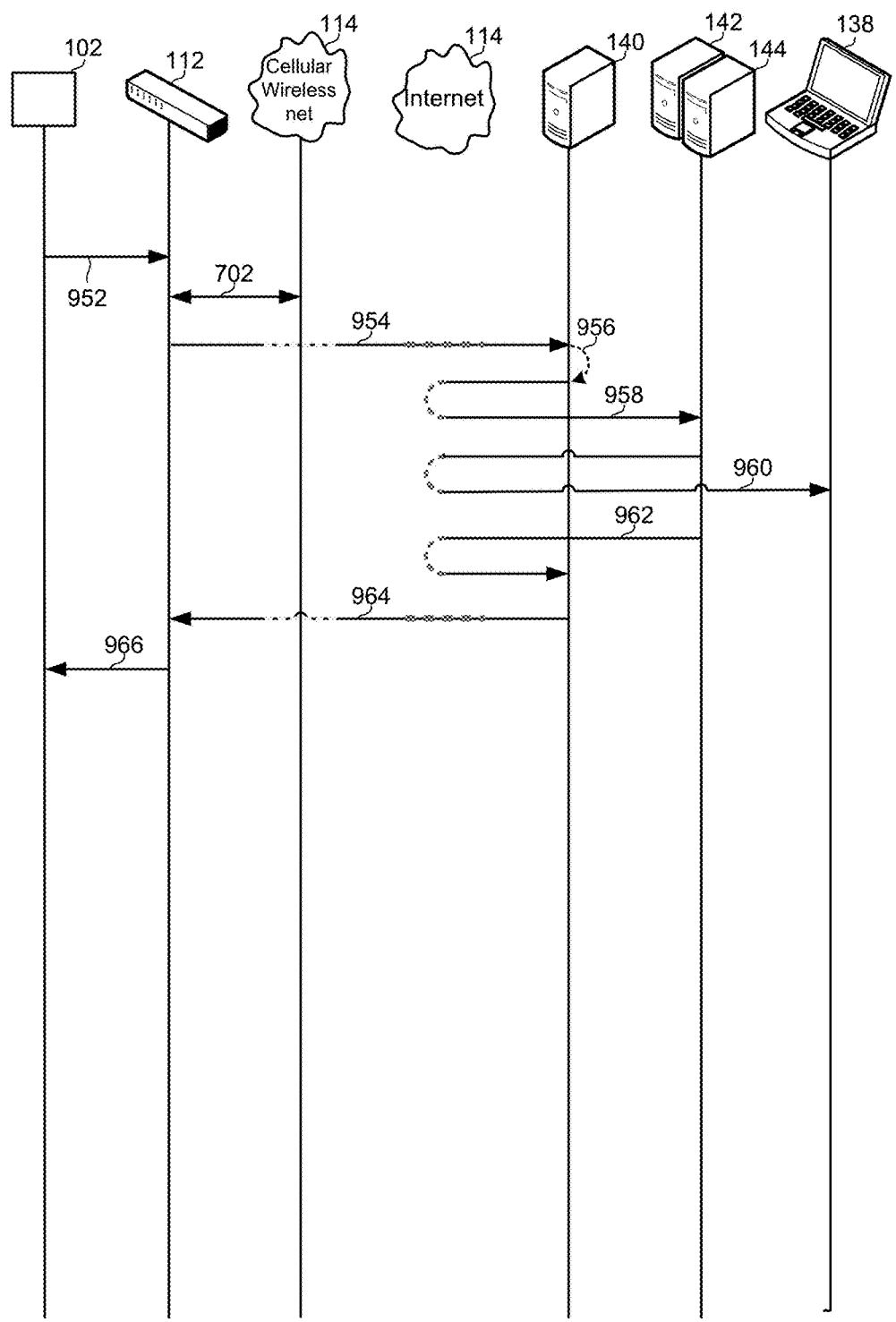
FIG. 9B is a message flow diagram illustrating messages that may be exchanged among various communication network participants during the embodiment method illustrated in FIG. 9A.

A wireless communication hub device 112 that is in a deactivated, low power, idle, or sleep mode may also be activated in response to receiving a data message from a connected electronic medical and fitness device. FIG. 9A illustrates an example method 900 for communicating data to data users initiated by a electronic medical and fitness device data push. Example messages that may be passed among system components in method 900 are illustrated in FIG. 9B. Referring to FIGS. 9A (for steps) and 9B (for messages), when an electronic medical and fitness device 102 determines that it has data that should be transmitted to an appropriate data user (e.g., a medical facility, a device manufacturer, a user, etc.) it may transmit the data to the wireless communication hub device 112 via the established communication connection. Upon receiving the data message, the wireless communication hub device 112 may recognize the particular electronic medical and fitness device providing the data. This may be accomplished based upon the particular communication port through which the data signal was received or information provided with the data message, such as a device identifier. As part of this step, the wireless communication hub device processor 301 may obtain the IPv6 address, MAC ID or other unique identifier for the reporting electronic medical and fitness device that is known to be service platform server 140 (i.e., the identifier that was reported to the server during a registration and configuration process). If a data connection is not already established with a cellular wireless network 130, the wireless communication hub device 112 may activate the cellular transceiver 303 and exchange the network signaling messages 702 necessary to establish a cellular data communication link with the cellular wireless network 130. If a local wireless router 135 with access to the Internet 114 is available, the wireless communication hub device 112 may negotiate a communication link with the wireless router instead. Once connected to the cellular wireless network 130 (or a local wireless router 135), the wireless communication hub device 112 may place a data call to the service platform server 140. When a connection to the service platform server 140 is established (or as part of establishing the connection), the wireless communication hub device 112 may provide its unique identifier to the server, thereby identifying itself, step 508. Once the wireless communication hub device 112 has registered with the service platform server 140 it may transmit the data received from the electronic medical and fitness device 102. The data message also includes the identifier for the device providing the data. The service platform server 140 may use the electronic medical and fitness device identifier to determine the appropriate processing and destination for the data. If the data is to be transmitted immediately to another destination, such as a medical or device manufacturer server 142, 144, the service platform server 140 may contact the appropriate server and negotiate an appropriate encrypted communication link via the Internet 114. Once an appropriate communication link is established, the service platform server 140 may transmit the received device data to the destination server 142, 144 via the Internet 114. The destination server 142, 144 receiving the data may then process or use the data for other purposes, such as transmitting a notification message to the user's personal computer 138 via the Internet 114.

Referring to FIGS. 9A (for steps) and 9B (for messages), when an electronic medical or fitness device 102 determines that it has data that should be transmitted to an appropriate data user (e.g., a medical facility, a device manufacturer, a user, etc.) it may transmit the data to the wireless communication hub device 112 via the established communication connection, step 902 and message 952. Upon receiving the data message, the wireless communication hub device 112 may recognize the particular electronic medical or fitness device 102 providing the data, step 904. This may be accomplished based upon the particular communication port through which the data signal was received or information provided with the data message, such as an electronic medical or fitness device 102 identifier. As part of this step, the wireless communication hub device 112 processor 301 may obtain the IPv6 address, MAC ID or other unique identifier for the reporting electronic medical or fitness device that is known to be service platform server (i.e., VPH-server) 140 (i.e., the identifier that was reported to the service platform server 140 during a registration and configuration process). If a data connection is not already established with a cellular wireless network 130, the wireless communication hub device 112 may activate the cellular transceiver 303 and exchange the network signaling messages 702 necessary to establish a cellular data communication link with the cellular wireless network 130. If a local wireless router 135 with access to the Internet 114 is available, the wireless communication hub device 112 may negotiate a communication link with the local wireless router 135 instead. Once connected to the cellular wireless network 130 (or a local wireless router 135), the wireless communication hub device 112 may place a data call to the service platform server 140, step 506. When a connection to the service platform server 140 is established (or as part of establishing the connection), the wireless communication hub device 112 may provide its unique identifier to the service platform server 140, thereby identifying itself, step 508. Once the wireless communication hub device 112 has registered with the service platform server 140 it may transmit the data received from the electronic medical or fitness device 102, step 910 and message 954. The data message transmitted in step 910 and message 954 also includes the identifier for the electronic medical or fitness device providing the data. The service platform server 140 may use the electronic medical or fitness device identifier to determine the appropriate processing and destination for the data, step 912 and processing 956. If the data is to be transmitted immediately to another destination, such as a medical or device manufacturer server 142, 144, the service platform server 140 may contact the appropriate server and negotiate an appropriate encrypted communication link via the Internet 114, step 914. Once an appropriate communication link is established, the service platform server 140 may transmit the received device data to the destination server 142, 144 via the Internet 114, step 916 and message 958. The server 142, 144 receiving the data may then process or use the data for other purposes, such as transmitting a notification message to the user's personal computer 138 via the Internet 114, message 960.

As noted above, the service platform services may be two-way, enabling data users to also transmit commands or messages back through the M2M communication hub 112 to selected electronic medical or fitness devices. This may involve a data user server 142, 144 transmitting a message 962 addressed to a particular electronic medical or fitness device to the service platform server 140, which receives the message via the Internet 114, step 918. The service platform server 140 re-addresses the message to the particular electronic medical or fitness device IPv6 address, step 920, and transmits the message to the wireless communication hub device 112 via the Internet 114, step 922 and message 964. The wireless communication hub device 112 receives the messages and relays them onto the addressed the electronic medical or fitness device, step 924 and message 966. The addressed electronic medical or fitness device then processes or displays the message, step 926.

A practical implementation example may clarify the processing described above with reference to FIGS. 9A and 9B. Since sudden weight gain can be an indicator of some serious medical conditions, providing such information to a medical facility may be useful for advising patients when they need to take medication or see a doctor immediately. To enable such early warning with minimal effort by patients, an electronic bathroom scale may be configured as an electronic medical or fitness device with a wireless (or wired) transceiver that couples to a wireless communication hub device 112 to transmit weight readings whenever a user starts on the scale. The scale, the wireless communication hub device 112, and/or the service platform server 140 may be configured (e.g., as part of a registration process) to promptly forward scale readings to a medical facility server 142 that is tracking a patient's weight. When a user steps on the scale, the weight reading may be automatically transmitted to a destination server 142 that can process the information without any action or involvement on the part of the user. If the medical facility server 142 detects a sudden change in weight that may indicate a condition requiring a medical intervention (e.g., taking a medication or visiting a doctor), the server 142 may transmit a message to be displayed on an appropriate electronic medical or fitness device (e.g., the weight scale) that the user is likely to see. Thus, the medical facility server 142 may transmit a message using the service platform services so that it is receives by an electronic medical or fitness device (such as an LCD display, a digital picture frame, or other device with a display) informing the user to take the proper precautions.

Figure 18:
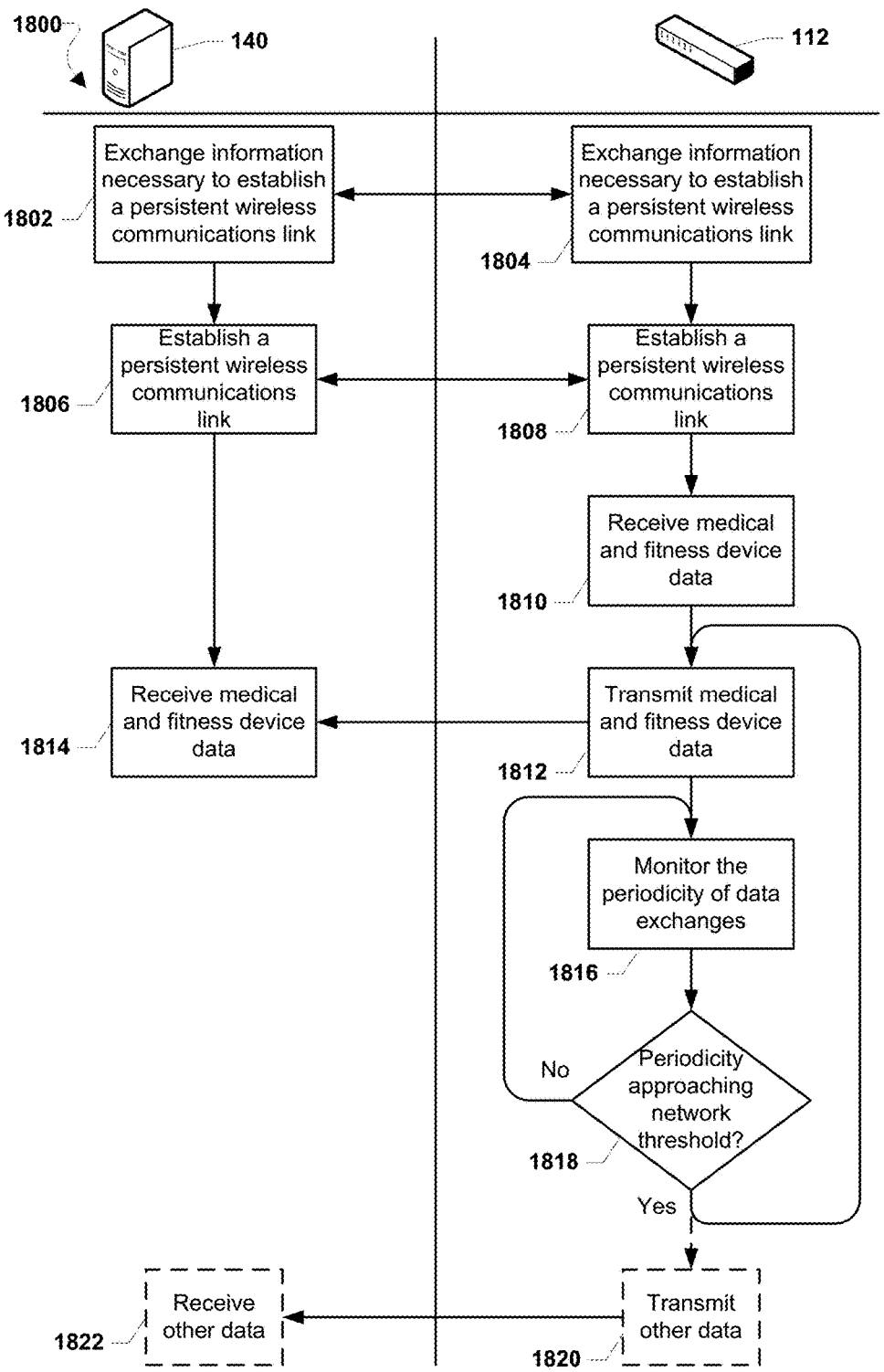
FIG. 18 is a process flow diagram illustrating an embodiment method for maintaining a persistent wireless communication link.

FIG. 18 illustrates an embodiment method 1800 for enabling the wireless communication hub device 112 to establish a persistent wireless communications link with the service platform server 140. In blocks 1802 and 1804 the wireless communication hub device 112 and the service platform server 140 may exchange information necessary to establish a persistent wireless communications link between each other. In blocks 1806 and 1808 the wireless communication hub device 112 and the service platform server 140 may establish a persistent wireless communications link with each other. A persistent wireless communications link may be a communications link that is kept open regardless of the rate of data sent over the wireless communication link. In block 1810 the wireless communication hub device 112 may receive medical and fitness device data from the medical and fitness device 102 as discussed above. At block 1812 the wireless communication hub device 112 may transmit medical and fitness device data to the service platform server 140 as discussed above. At block 1814 the service platform server 140 may receive the medical and fitness device data.

At block 1816 the wireless communication hub device 112 may monitor the periodicity of data exchanges with the service platform server 140. As an example, the wireless communication hub device 112 may compare a time stamp associated with the last transmission of the wireless communication hub device 112 to the current wireless communication hub device 112 time. At determination block 1818 the wireless communication hub device 112 may determine if the periodicity is approaching a network threshold. As an example, the wireless communication hub device 112 may compare a network threshold, such as the maximum time allowed between transmissions before a communication link is deemed dormant (which may be stored in a memory 302), to the time period since the last data transmission. If the period since the last data transmission is approaching the network threshold (i.e., determination block 1818="Yes"), at block 1812 the wireless communication hub device 112 may transmit the medical and fitness device data to the service platform server 140. If the period since the last data transmission is not approaching the network threshold (i.e., determination block 1818="No"), at block 1816 the wireless communication hub device 112 may monitor the periodicity of data exchanges with the service platform server 140. In this manner, the persistent wireless communications link may be maintained despite network thresholds for activity because the persistent wireless communications link may not be identified as dormant by a host network. By not being identified as dormant, the persistent wireless communications link may be less at risk for being automatically broken or closed by the host network. In an optional embodiment, if the period since the last data transmission is approaching the network threshold (i.e., determination block 1818="Yes"), at block 1820 the wireless communication hub device 112 may transmit data other than medical and fitness device data to the service platform server 140. The other data may be any data, such as a test message, that may serve to keep the persistent wireless communication link active. At block 1822 the service platform server 140 may receive the other data.

Figure 19:
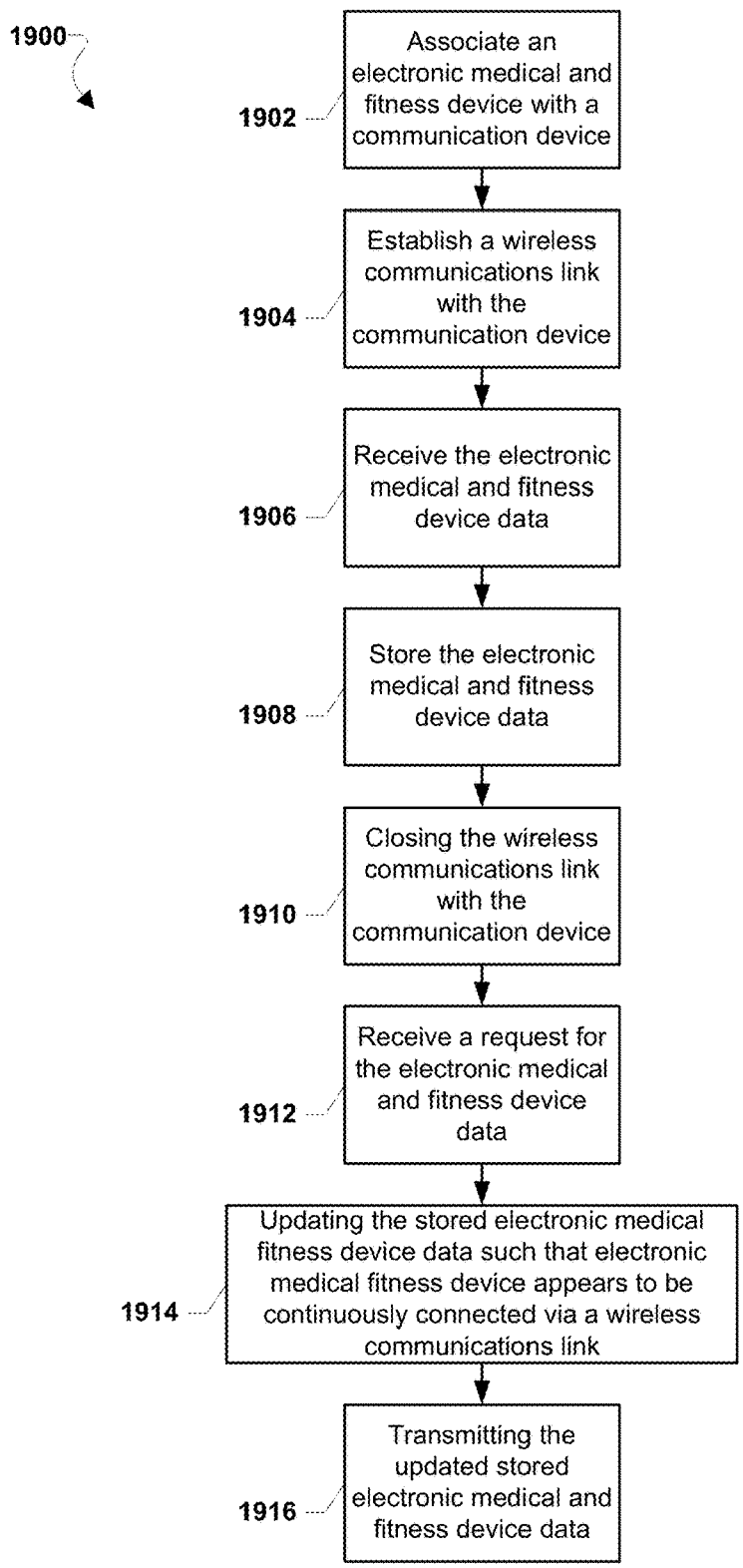
FIG. 19 is a process flow diagram illustrating an embodiment method for enabling the appearance of persistent connections with electronic medical or fitness devices.

FIG. 19 illustrates an embodiment method 1900 for enabling the appearance that the electronic medical and fitness device 102 is continuously connected to another device (e.g., a physician's personal computer 138) accessing the electronic medical and fitness device via the service platform server 140, without the need to maintain a constant communication link between the electronic medical and fitness device 102 and the wireless communication hub device 112. At block 1902 the service platform server 140 may associate an electronic medical and fitness device 102 with a communication device, such as the wireless communication hub device 112. At block 1904 the service platform server 140 may establish a wireless communications link with the communication device (e.g., the wireless M2M communications hub 112). At block 1906 the service platform server 140 may receive the electronic medical and fitness data from the communication device (e.g., the wireless M2M communications hub 112) via the wireless communications link. At block 1908 the service platform server 140 may store the electronic medical and fitness device data. In an embodiment, the electronic medical or fitness device data may include an electronic medical or fitness device identifier. The service platform server 140 may compare the received electronic medical or fitness device identifier to a database of electronic medical or fitness device identifier associated with users to identify at least one of a user account, a partner account (e.g., account on a third party server 142) and/or a service account (e.g., a third party account on server 142) associated with the electronic medical or fitness device, and may store the medical or fitness data received from the communication hub device in a data record for the user associated with the electronic medical or fitness device. At block 1910 the service platform server 140 may close the wireless communications link with the communication device (e.g., the wireless M2M communications hub 112).

At block 1912 the service platform server 140 may receive a request for the electronic medical and fitness device data from another device (e.g., the physician's personal computer 138). At block 1914 the service platform server 140 may update the stored electronic medical and fitness device data such that the electronic medical or fitness device appears to be continuously connected via a wireless communications link. As an example, the service platform server 140 may update a time stamp on the stored electronic medical and fitness device data to reflect the current service platform server 140 time. At block 1916 the service platform server 140 may transmit the updated stored electronic medical and fitness device data to the other device (e.g., the physician's personal computer 138). In this manner, the electronic medical and fitness device data received may appear to be current electronic medical and fitness device data and it may appear that the other device (e.g., the physician's personal computer 138) is continuously connected via a wireless communications link to the electronic medical and fitness device 102, though a continuous wireless communications link may not be established.

Figure 24:
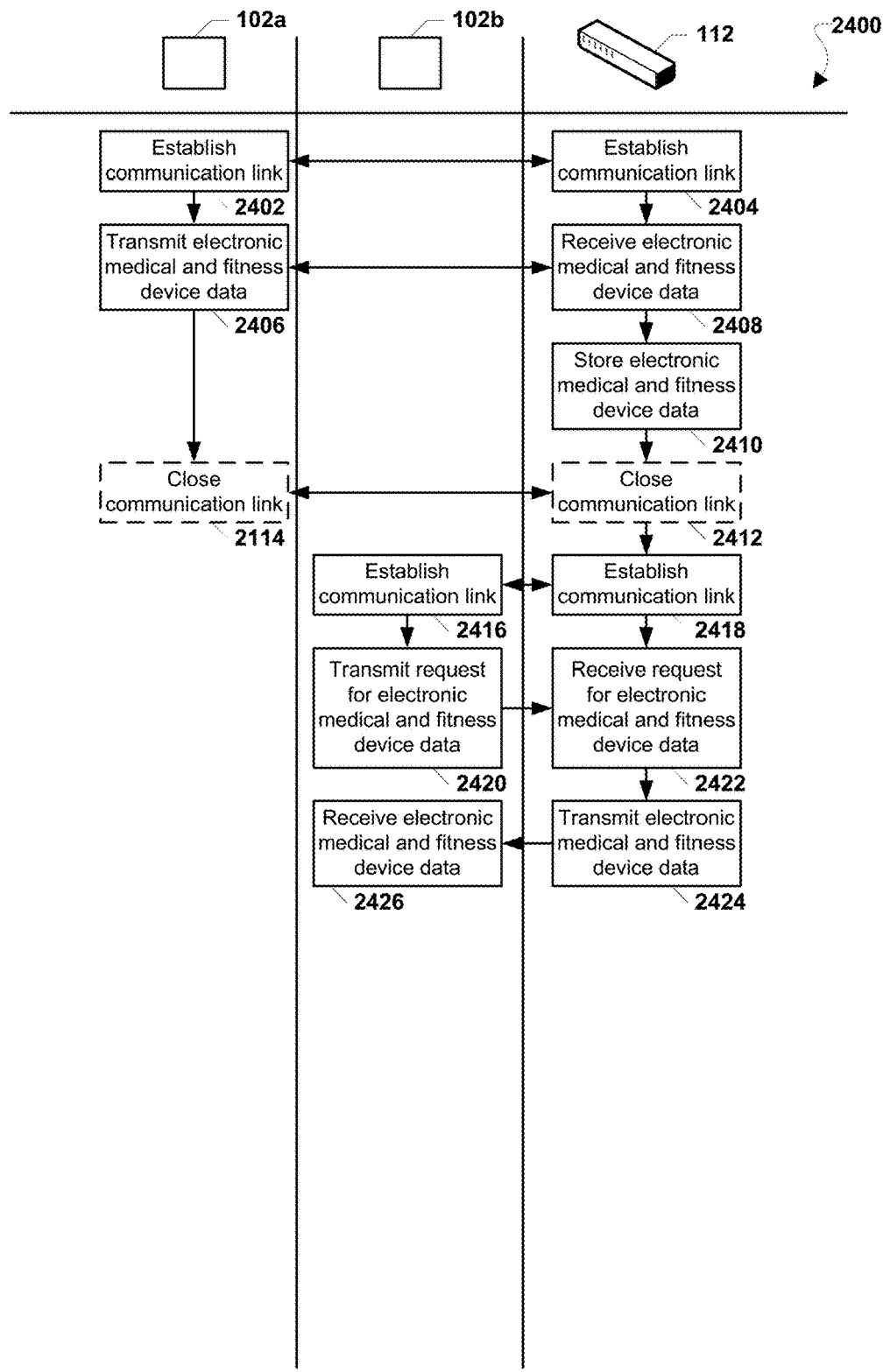
FIG. 24 is a process flow diagram illustrating an embodiment method for electronic medical or fitness device data sharing.

FIG. 24 illustrates an embodiment method 2400 for enabling two electronic medical and fitness devices 102a and 102b to exchange data. In blocks 2402 and 2404 the first electronic medical and fitness device 102a and the wireless communication hub device 112 may establish a first communication link with each other. In block 2406 the first electronic medical and fitness device 102a may transmit electronic medical and fitness device data to the wireless communication hub device 112 via the first communication link. At block 2408 the wireless communication hub device 112 may receive the electronic medical and fitness device data. At block 2410 the wireless communication hub device 112 may store the received electronic medical and fitness device data in a memory resident on the wireless communication hub device 112. In an optional embodiment, at blocks 2412 and 2114 the wireless communication hub device 112 and the first electronic medical and fitness device 102a may close the first communication. At blocks 2416 and 2418 the second electronic medical and fitness device 102b and the wireless communication hub device 112 may establish a second communication link between each other. At block 2420 the second electronic medical and fitness device 102b may transmit a request for the electronic medical and fitness device data to the wireless communication hub device 112 via the second communication link. In an embodiment, the request for the electronic medical and fitness device data may specify a specific type of data (e.g., weight or blood pressure data), a specific type of originating device (e.g., a weight scale or blood pressure monitor), and/or a specific originating device ID (e.g., the device ID for the user's specific weight scale). At block 2422 the wireless communication hub device 112 may receive the request for the medical and fitness device data. At block 2424 the wireless communication hub device 112 may transmit the electronic medical and fitness data requested, and at block 2426 the second electronic medical and fitness device 102b may receive the electronic medical and fitness device data. In this manner, a second electronic medical and fitness device 102b may access data from a first electronic medical and fitness device 102a via the wireless communication hub device 112 whether the first electronic medical and fitness device 102a may be currently, or may have been previously connected to the wireless communication hub device 112.

Figure 25:
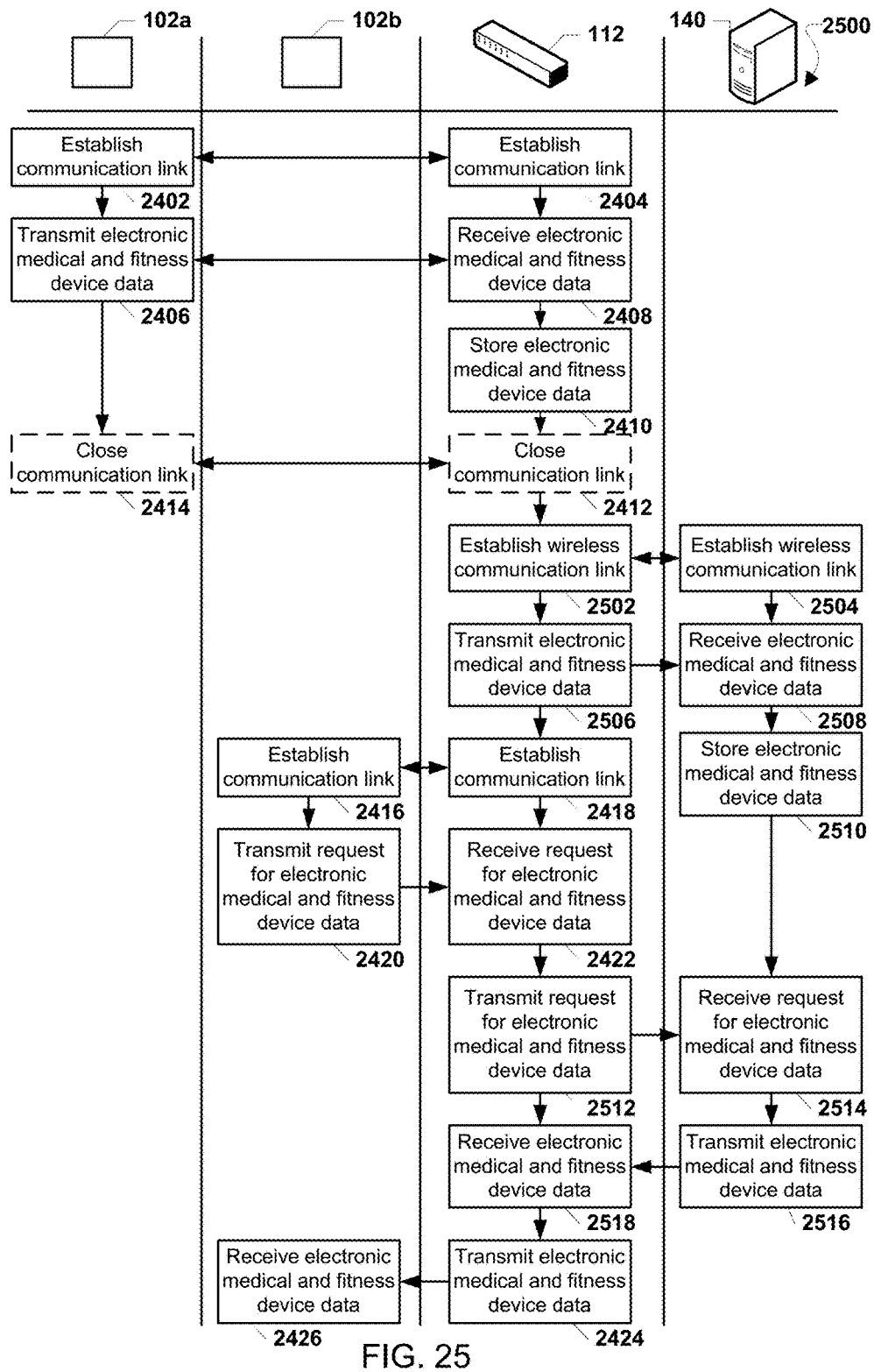
FIG. 25 is a process flow diagram illustrating another embodiment method for electronic medical or fitness device data sharing.

FIG. 25 illustrates an embodiment method 2500 for enabling two electronic medical and fitness devices 102a and 102b to exchange data similar to method 2400 described above with reference to FIG. 24, except that the wireless communication hub device 112 may exchange electronic medical and fitness data with the service platform server 140. At blocks 2402, 2406, 2408, 2410, 2412, and 2414 operations of method 2400 as described above with reference to FIG. 24 may be performed. At blocks 2502 and 2504 the wireless communication hub device 112 and may the service platform server 140 may establish a wireless communication link with each other. At block 2506 the wireless communication hub device 112 may transmit the electronic medical and fitness device data to the service platform server 140, and at block 2508 the service platform server 140 may receive the electronic medical and fitness data. At block 2510 the service platform server 140 may store the electronic medical and fitness device data. At blocks 2416, 2418, 2420, and 2422 operations of method 2400 as described above with reference to FIG. 24 may be performed. At block 2512 the wireless communication hub device 112 may transmit the request for the electronic medical and fitness device data to the service platform server 140. In an embodiment, the request may be transmitted by the wireless communication hub device 112 in response to a determination that the previously stored electronic medical and fitness device data is no longer available to the wireless communication hub device 112. At block 2514 the service platform server 140 may receive the request for electronic medical and fitness device data. At block 2516 the service platform server 140 may transmit the electronic medical and fitness device data to the wireless communication hub device 112. At block 2518 the wireless communication hub device 112 may receive the electronic medical and fitness device data. At block 2424 the wireless communication hub device 112 may transmit the electronic medical and fitness data requested, and at block 2426 the second electronic medical and fitness device 102b may receive the electronic medical and fitness device data. In this manner, two electronic medical and fitness devices 102a and 102b may exchange data via the service platform server 140.

Figure 26:
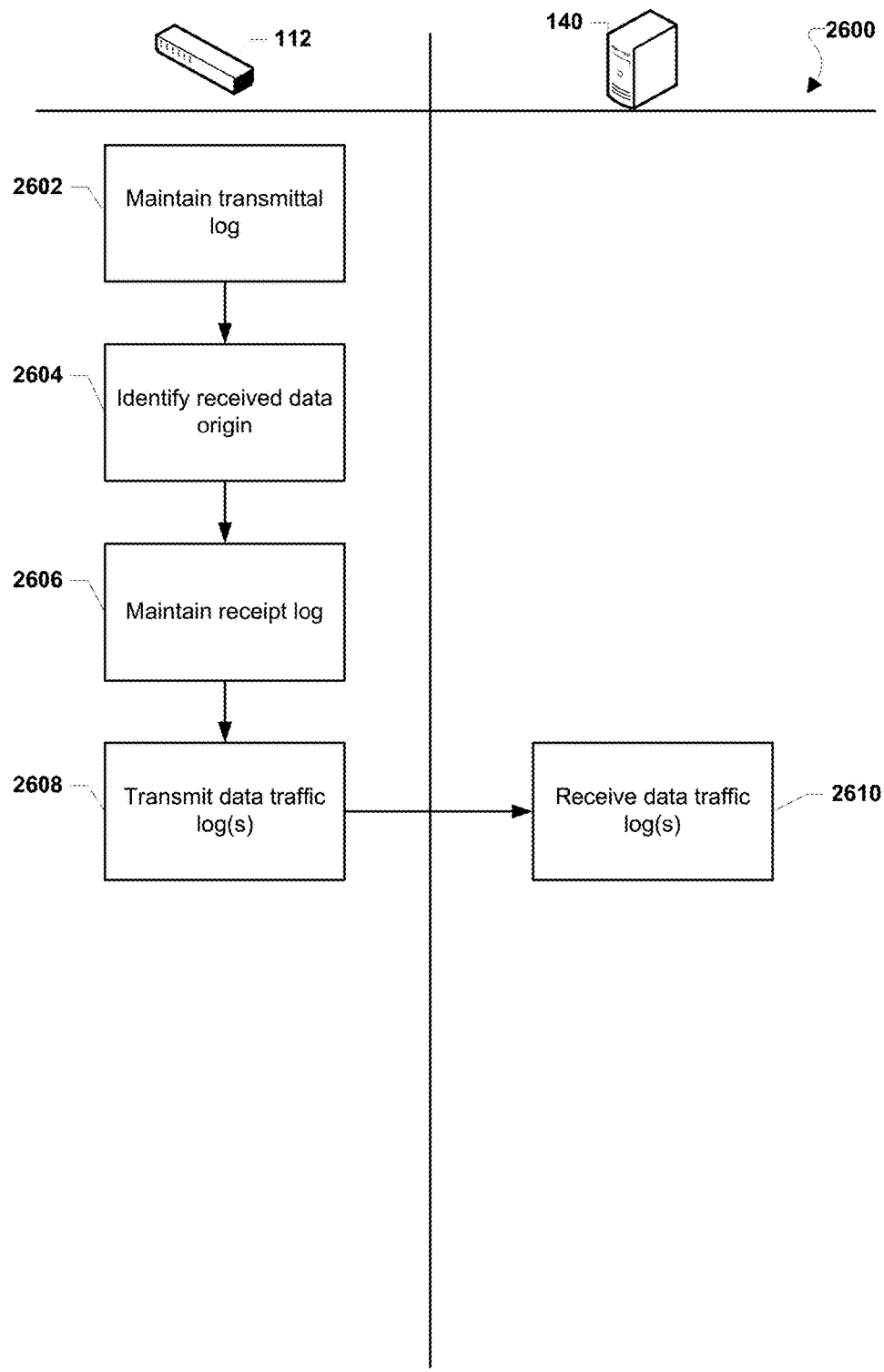
FIG. 26 is a process flow diagram illustrating an embodiment method for tracking data traffic through the wireless communication hub device.

In an embodiment, the wireless communication hub device may be a part of communications that may need to be monitored. Communications with the wireless communication hub device 112 may be carried over the cellular operator's network, and may result in a billing event for the service platform, retailers, customers and/or users associated with the wireless communication hub device 112. FIG. 26 illustrates an embodiment method 2600 for tracking data traffic through the wireless communication hub device 112. At block 2602 the wireless communication hub device 112 may maintain a transmittal log. In an embodiment, the transmittal log may be a log of all transmissions sent from the wireless communication hub device 112. The transmittal log may be any type log, such as a counter for each byte of data traffic sent from the wireless communication hub device 112. At block 2404 the wireless communication hub device 112 may identify the origin of received data traffic. In an embodiment, the wireless communication hub device 112 may parse data headers to determine the origin of received data. In this manner, data originated at the service platform server 140 may be distinguished from data originated at a customer server but transmitted via the service platform server 140. At block 2606 the wireless communication hub device 112 may maintain a receipt log. In an embodiment, the receipt log may be a log of all traffic received by the wireless communication hub device 112. In an embodiment, the receipt log may distinguish data traffic by the origin of the data traffic (e.g., data traffic originated at the service platform server 140 may be distinguished in a receipt log from data traffic originated at a customer server). The receipt log may be any type log, such as a counter for each byte of data traffic received by the wireless communication hub device 112. At block 2608 the wireless communication hub device 112 may transmit the data traffic log(s) (i.e., the transmittal log and/or the receipt log) to the service platform server 140. At block 2610 the service platform server 140 may receive the data traffic log(s). In this manner the data traffic log(s) may be utilized by the service platform server to reconcile and generate reports, generate statistics, and/or generate and resolve billing statements. In a further embodiment, SMS messages (e.g., MT SMS and/or MO SMS messages) may be tracked in conjunction with data traffic by the wireless communication hub device 112.

Figure 27:
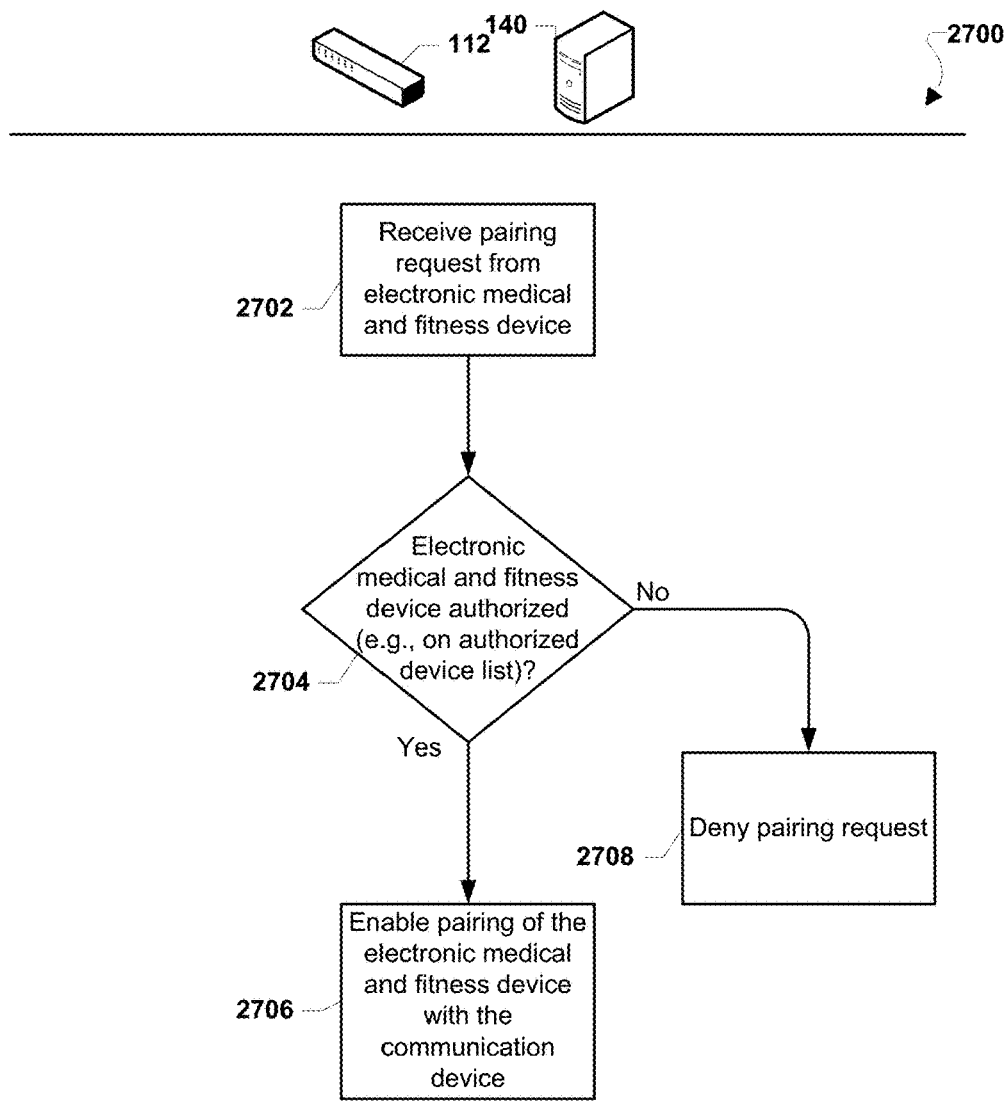
FIG. 27 is a process flow diagram illustrating an embodiment method for managing electronic medical or fitness device authorization.

FIG. 27 illustrates a method 2700 for managing device authorization which may be performed by the service platform server 140 or the wireless communication hub device 112. In an embodiment the service platform server 140 may have stored in a memory a listing of authorized electronic medical or fitness devices. In an embodiment, the wireless communication hub device 112 may have previously received a listing of authorized electronic medical or fitness devices and may have stored the listing of authorized electronic medical or fitness devices in a memory of the wireless communication hub device 112. At block 2702 the service platform server 140 or the wireless communication hub device 112 may receive a pairing request originated from the electronic medical and fitness device, such as the electronic medical and fitness device 102. In an embodiment, the pairing authorization request may include electronic medical and fitness device information, such as an electronic medical and fitness device ID and/or an electronic medical and fitness device type. At determination block 2704 the service platform server 140 or the wireless communication hub device 112 may determine if the electronic medical and fitness device is authorized to be paired with the wireless communication hub device 112. In an embodiment, authorization may be determined by comparing electronic medical and fitness device information (e.g., an electronic medical and fitness device ID) to a listing of authorized electronic medical of fitness devices (e.g., list of authorized devices). In another embodiment, authorization may be determined by authenticating the electronic medical and fitness device by comparing electronic medical and fitness device information (e.g., an electronic medical and fitness device ID and type) to an authorized electronic medical and fitness device list to determine if the device ID and type match the authorized list. If the electronic medical and fitness device is authorized (i.e., determination block 2704="Yes"), at block 2706 pairing of the electronic medical and fitness device with the communication device (e.g., wireless communication hub device 112) may be enabled by the service platform server 140 or the wireless communication hub device 112. In an embodiment, the service platform server 140 may transmit a device authorization message to the wireless communication hub device 112 authorizing communication with the discovered electronic medical or fitness device. If the electronic medical and fitness device is not authorized (i.e., determination block 2704="No"), at block 2708 the service platform server 140 or the wireless communication hub device 112 may deny the pairing request. In an embodiment, the service platform server 140 may transmit an electronic medical or fitness device authorization message to the wireless communication hub device authorizing communication and/or pairing with the discovered electronic medical or fitness device.

Figure 28:
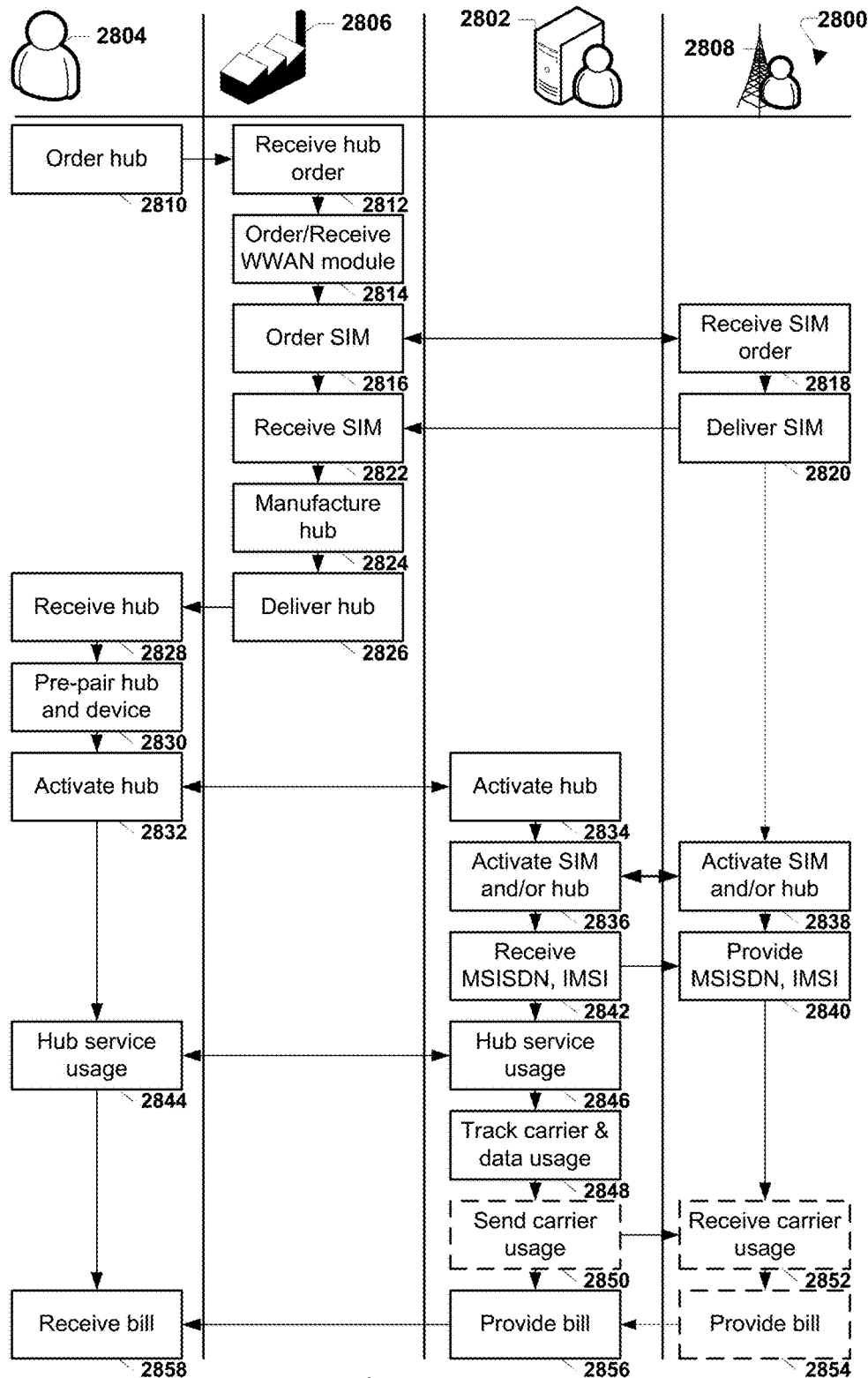
FIG. 28 is a process flow diagram illustrating an embodiment method for procurement, provisioning, activation, and billing of a wireless communication hub device.

FIG. 28 illustrates an embodiment method 2800 for procurement, provisioning, activation, and billing of a wireless communication hub device according to the various embodiments for use with a UMTS communication network. At block 2810 a customer server operator 2804 may order a wireless communication hub device. The customer server operator 2804 may be a retailer of wireless communication hub devices, an end user of wireless communication hub devices, and or the operator of a server (i.e., customer server) that utilizes wireless communication hub devices to receive/manage electronic medical and fitness devices and/or electronic medical and fitness device data. At block 2812 a wireless communication hub device manufacturer 2806 may receive the wireless communication hub device order. At block 2806 the wireless communication hub device manufacturer 2806 may order/receive a WWAN module for the wireless communication hub device. At block 2816 the wireless communication hub device manufacturer 2806 may order a subscriber identity module (SIM) card for the wireless communication hub device. At block 2818 the cellular operator/carrier 2808 may receive the SIM order. In an embodiment, the wireless communication hub device manufacturer 2806 may order the SIM card directly from a cellular operator/carrier 2808, or alternatively may order then from a SIM card manufacturer who may receive SIM information from the cellular operator/carrier 2808 for inclusion in the SIM cards. In an embodiment the SIM cards store the necessary credentials for the wireless communication hub device to operate on the cellular operator/carrier's 2808 network. At block 2820 the cellular operator/carrier 2808 may deliver the SIM card. At block 2822 the wireless communication hub device manufacturer 2806 may receive the SIM card. At block 2824 the wireless communication hub device manufacturer 2806 may manufacture the wireless communication hub device including the WWAN module and SIM card. At block 2826 the wireless communication hub device manufacturer 2806 may deliver the wireless communication hub device and at block 2828 the customer server operator 2804 may receive the wireless communication hub device.

At block 2830 the customer server operator 2804 may pre-pair the wireless communication hub device with an electronic medical and fitness device (e.g., a heart rate monitor). At blocks 2832 and 2834 the customer server operator 2804 and service platform server operator 2802 may activate the wireless communication hub device. In an embodiment, a customer server may communicate with the service platform server to authorize the wireless M2M communication huh, such as by sending wireless communication hub device information to the service platform server. At blocks 2836 and 2838 the service platform server operator 2802 and the cellular operator/carrier 2808 may activate the SIM and/or the wireless communication hub device. In an embodiment, the service platform server may interact with a server of the cellular operator/carrier 2808 to activate the SIM and/or the wireless communication hub device. At block 2840 the cellular operator/carrier 2808 may provide a MSISDN and/or IMSI for the wireless communication hub device. At block 2842 the service platform server operator 2802 may receive the MSISDN and/or IMSI. At blocks 2844 and 2846 the customer server operator 2804 and service platform server operator 2802 may utilize the wireless communication hub device, for example by sending electronic medical and fitness device data from the wireless communication hub device to the service platform server and on to the customer server. At block 2848 the service platform server operator 2802 may track cellular carrier network and data traffic usage by the wireless communication hub device. At block 2856 the service platform server operator 2802 may provide a bill to the customer server operator 2804. In an embodiment, the bill may be provided through billing services, such as a carrier usage monitoring service, fraud monitoring service, and/or a billing entity. At block 2858 the customer server operator 2804 may receive the bill. In an optional embodiment, the service platform server operator 2802 may send cellular carrier network usage information to the cellular operator/carrier 2808. At block 2852 the cellular operator/carrier 2808 may receive the cellular carrier network usage information, and at block 2854 the cellular operator/carrier 2808 may provide a bill to the service platform server operator 2802. In an alternative embodiment the cellular operator/carrier 2808 may directly bill the customer server operator 2804.

Figure 29:
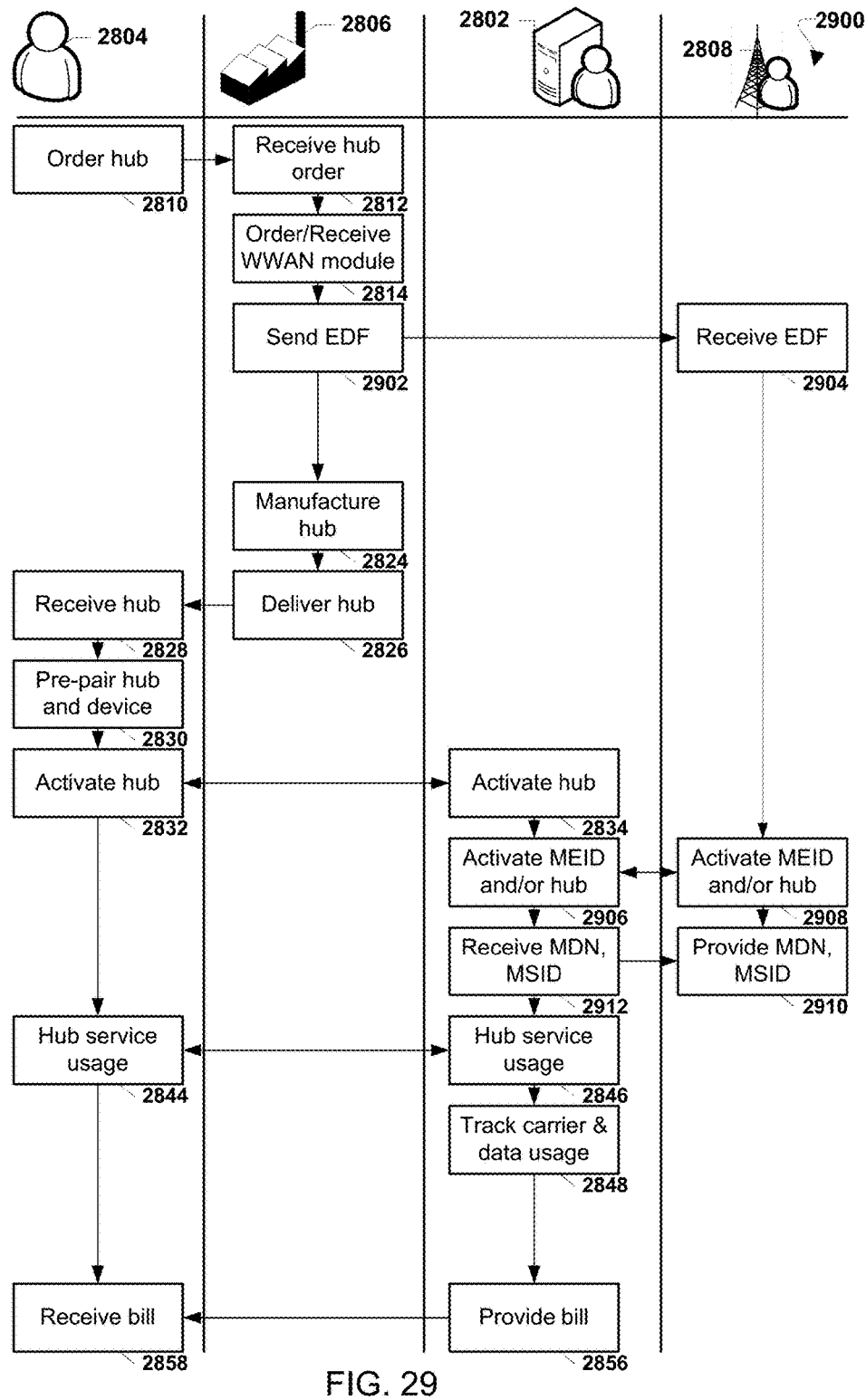
FIG. 29 is a process flow diagram illustrating another embodiment method for procurement, provisioning, activation, and billing of a wireless communication hub device.

FIG. 29 illustrate another embodiment method 2900 for procurement, provisioning, activation, and billing of a wireless communication hub device according to the various embodiments similar to method 2800 described above with reference to FIG. 28, except that method 2900 may be used with a CDMA communication network. At blocks 2810, 2812, and 2814, operations of method 2800 may be performed as described above with reference to FIG. 28. At block 2902 the wireless communication hub device manufacturer 2806 may send the EDF (i.e., WANN ID) to the cellular operator/carrier 2808. At block 2904 the cellular operator/carrier 2808 may receive the EDF. At blocks 2824, 2826, 2828, 2830, 2832, and 2834, operations of method 2800 may be performed as described above with reference to FIG. 28. At blocks 2906 and 2908 the service platform server operator 2802 and the cellular operator/carrier 2808 may activate the MEID and/or the wireless communication hub device. In an embodiment, the service platform server may interact with a server of the cellular operator/carrier 2808 to activate the MEID and/or the wireless communication hub device. At block 2910 the cellular operator/carrier 2808 may provide a MDN and/or MSID for the wireless communication hub device. At block 2912 the service platform server operator 2802 may receive the MDN and/or the MSID. At blocks 2844, 2846, 2848, 2856, and 2858, operations of method 2800 may be performed as described above with reference to FIG. 28.

Figure 30:
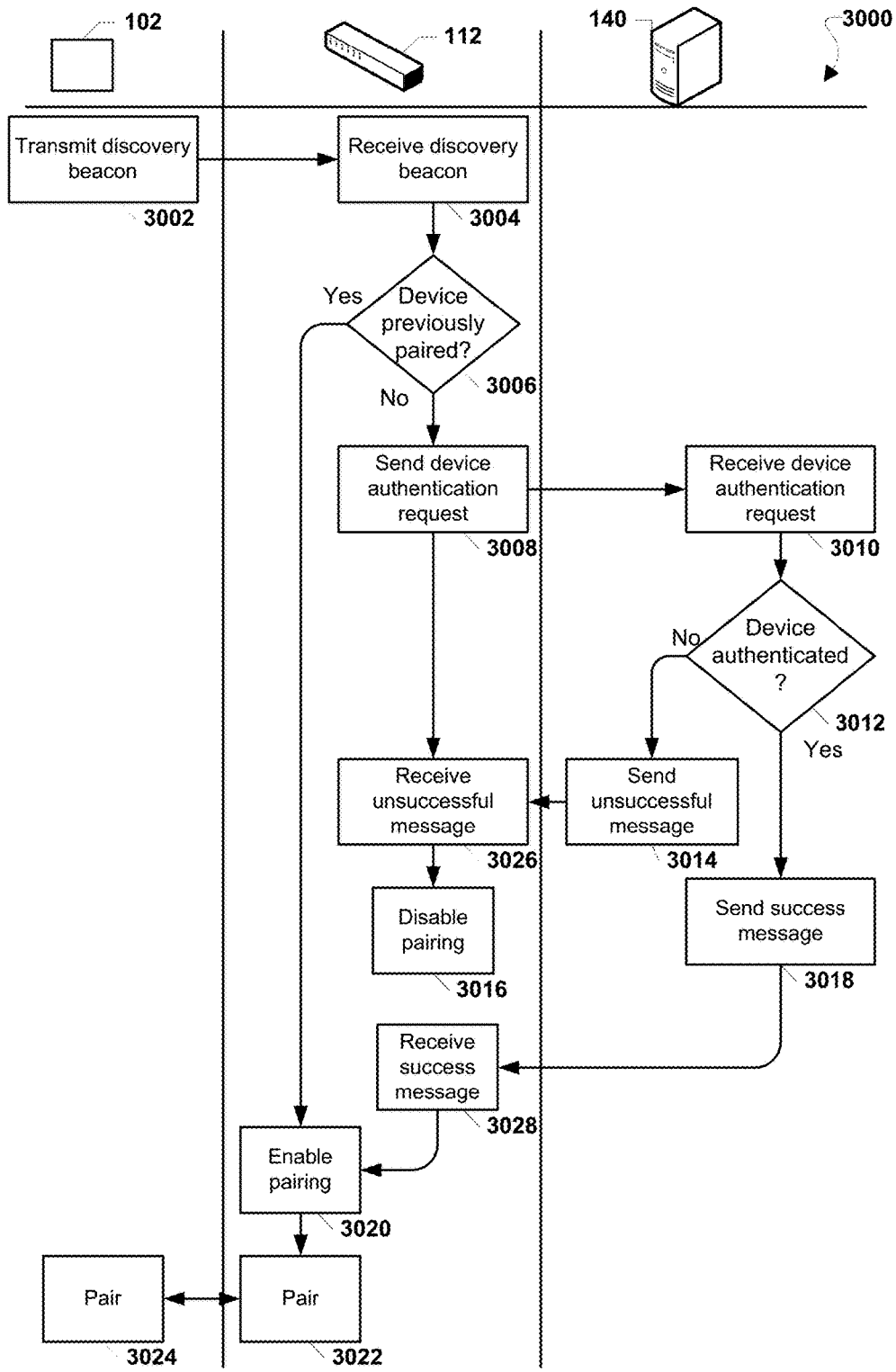
FIG. 30 is a process flow diagram illustrating an embodiment method for authenticating an electronic medical or fitness device.

FIG. 30 illustrates an embodiment method 3000 for authenticating an electronic medical and fitness device 102 through a service platform server 140. At block 3002 the electronic medical and fitness device 102 may transmit a discovery beacon. In an embodiment, the discovery beacon may be transmitted in response to a received query or may be periodically transmitted by the electronic medical and fitness device 102. In this manner, electronic medical or fitness devices coupled to the wireless communication hub device 112 may be discovered. In an embodiment, a discovery beacon may include electronic medical and fitness device 102 identification information (e.g., electronic medical or fitness device identifier) and/or device parameters. At block 3004 the wireless communication hub device 112 may receive the discovery beacon. At determination block 3006 the wireless communication hub device 112 may determine if the electronic medical and fitness device 102 was previously paired with the wireless communication hub device 112. In an embodiment, the determination of previous pairing may be made, at least in part, on electronic medical and fitness device 102 information contained in the discovery beacon. If the electronic medical and fitness device 102 was previously paired with the wireless communication hub device 112 (i.e., determination block 3006="Yes"), at block 3020 the wireless communication hub device 112 may enable pairing between with the electronic medical and fitness device 102. At block 3022 and 3024 the electronic medical and fitness device 102 and the wireless communication hub device may pair with each other.

If the electronic medical and fitness device 102 was not previously paired with the wireless communication hub device 112 (i.e., determination block 3006="No"), at block 3008 the wireless communication hub device 112 may send a device authentication request to the service platform server 140. In an embodiment by sending the device authentication request the wireless communication hub device 112 may be identifying each discovered electronic medical or fitness device to the service platform server 140. At block 3010 the service platform server 140 may receive the authentication request. In an embodiment, the authentication request may include electronic medical and fitness device 102 identification information (e.g., an identifier of the electronic medical or fitness device) and/or device parameters. At determination block 3012 the service platform server 140 may determine if the electronic medical and fitness device 102 is authenticated. In an embodiment, the service platform server 140 may compare electronic medical and fitness device 102 information (e.g., ID and device parameter) to an authorized electronic medical and fitness device list (e.g., a "white list") to determine if the electronic medical and fitness device 102 information is on the authorized list and/or if the information provided matches the information on the list. Alternatively, or in addition, the service platform server 140 may compare identifier information to a list of identifiers which are specifically not authorized or precluded (e.g., a "black list") to determine when the electronic or fitness device should not be authorized for pairing.

If the electronic medical and fitness device 102 is authenticated (i.e., determination block 3012="Yes"), at block 3018 the service platform server 140 may send a "success" message to the wireless communication hub device 112. At block 3028 the wireless communication hub device 112 may receive the "success" message. At block 3020 the wireless communication hub device 112 may enable pairing between with the electronic medical and fitness device 102. At block 3022 and 3024 the electronic medical and fitness device 102 and the wireless communication hub device 112 may pair with each other. If the electronic medical and fitness device 102 is not authenticated (i.e., determination block 3012="No"), at block 3014 the service platform server 140 may send an "unsuccessful message" to the wireless communication hub device 112. At block 3026 the wireless communication hub device 112 may receive the "unsuccessful" message. At block 3016 the wireless communication hub device 112 may disable pairing with the electronic medical and fitness device 102. In a further embodiment, a wireless communication hub device 112 may be a "service all" type hub and the service process server 140 may authenticate an electronic medical and fitness device 102 if simply the device type parameter matches an authorized device type list and/or authentication.

Figure 10:
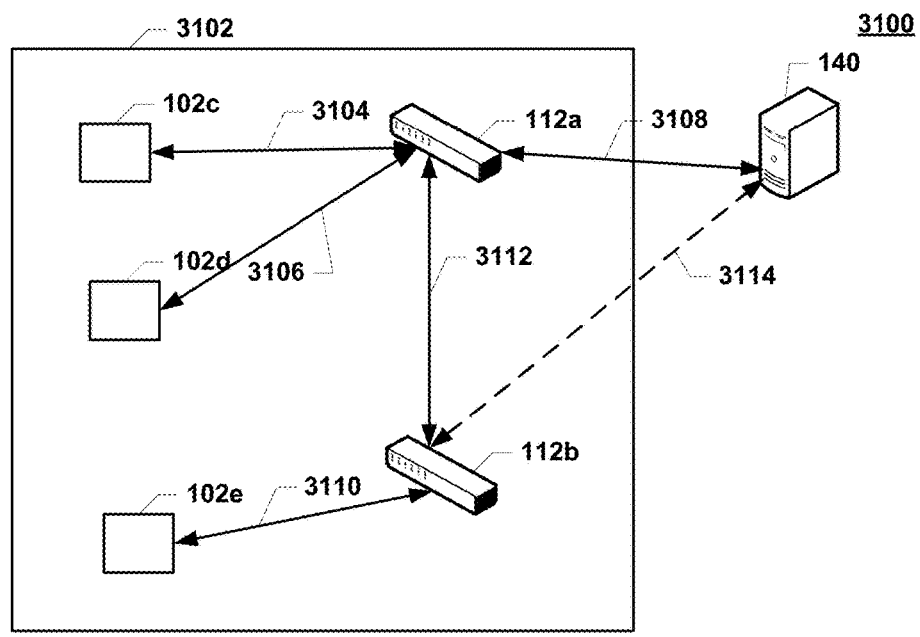
FIG. 10 is a communication system block diagram illustrating another embodiment communication system suitable for use with various embodiments.

FIG. 10 is a component block diagram illustrating a communication system 3100 with multiple-wireless communication hub devices 112a, 112b enabled by the various embodiments. In a geographic location 3102 (e.g., a user's house) wireless communication hub devices 112a, 112b, and electronic medical and fitness devices 102c, 102d, and 102e may be operating. Electronic medical and fitness devices 102c, 102d, and 102e may communicate with wireless communication hub devices 112a, and 112b, respectively, via communication pathways 3104, 3106, and 3110, respectively. In an embodiment, wireless communication hub devices 112a and 112b may communicate via communication pathway 3112. In an embodiment, one wireless communication hub device 112a may be a master hub and wireless communication hub device 112b may be a slave hub. Electronic medical and fitness devices 102e may send its electronic medical and fitness data to wireless communication hub device 112b. In the master/slave embodiment, the wireless communication hub device 112b may not have a communication link established with the service platform server 140, but rather must send and/or receive data with wireless communication hub device 112 which may then send and/or receive data with the service platform server 140 via communication pathway 3108. In an alternative embodiment, wireless communication hub device 112b may have its own communication pathway 3114 with the service platform server 140 and may send/receive its own data with the service platform server 140 via communication pathway 3114. In this manner, one wireless communication hub device 112a or 112b may be a master and the other a slave, or both may be equals. In this manner, the communication pathway 3112 established between the wireless communication hub devices 112a and 112b may serve as a backup connection pathway to the service platform server 140 and/or enable local data sharing at the geographic location 3102. In a further embodiment, electronic medical and fitness devices 102c, 102d, and 102e may be pre-paired with both wireless communication hub devices 112a and 112b, thus the electronic medical and fitness devices 102c, 102d, and 102e may be enabled to roam between the wireless communication hub devices 112a and 112b without requiring re-authentication by the service process server 140. In a further embodiment, wireless communication hub devices 112a and 112b may not be in the same geographic location 3102.

Figure 11:
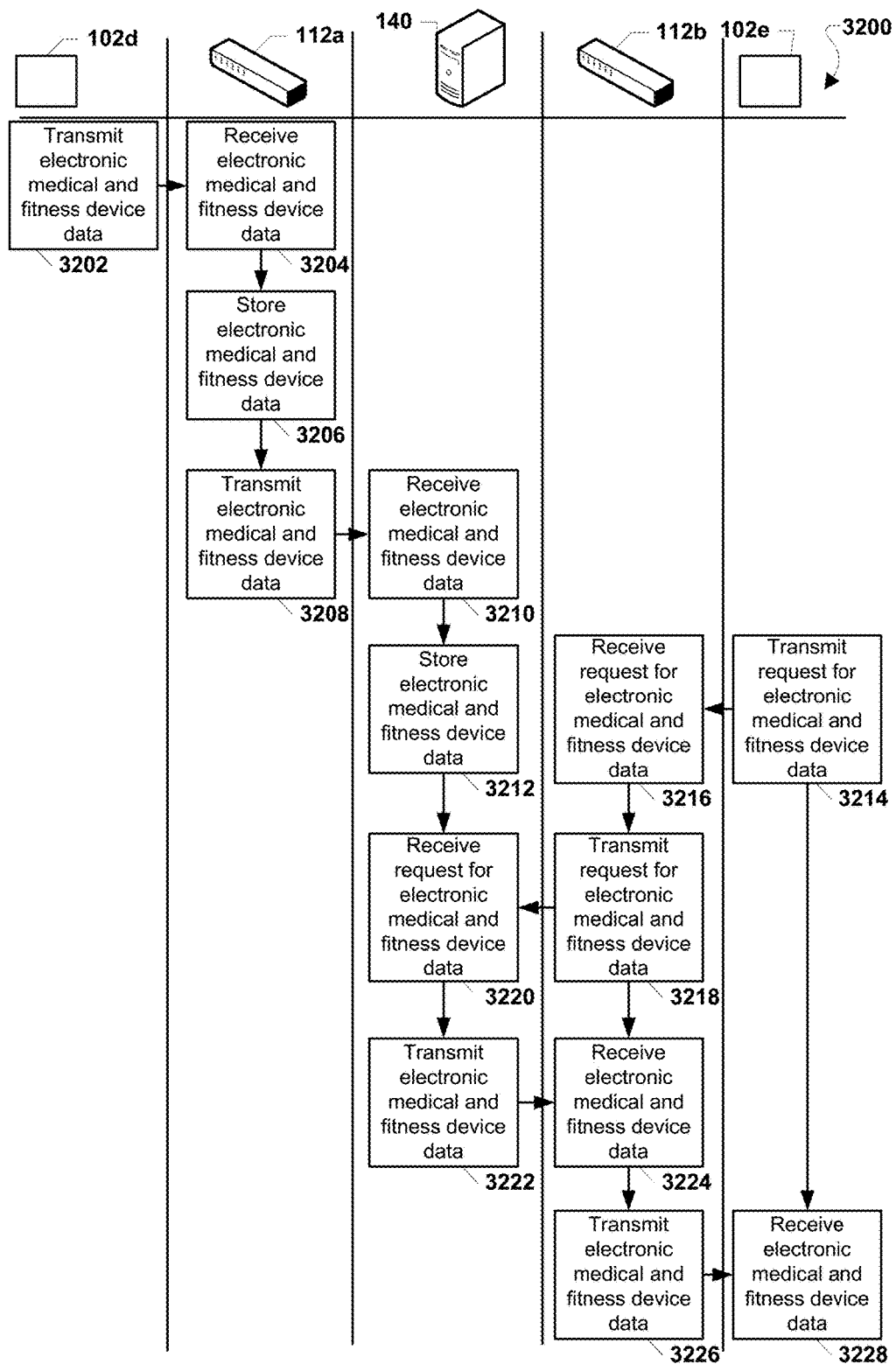
FIG. 11 is a process flow diagram illustrating an embodiment method for interconnected wireless communication hub device communication.

FIG. 11 illustrates an embodiment method 3200 enabling multi-wireless communication hub device 112a, 112b multi-electronic medical and fitness device 102d, 102e data sharing. In method 3200 the respective electronic medical and fitness devices 102d, 102e, may have previously established communication pathways with their respective wireless communication hub devices 112a, 112b. Additionally, the respective wireless communication hub devices 112a, 112b may have previously established communication pathways with the service platform server 140. At block 3202 electronic medical and fitness device 102d may transmit electronic medical and fitness device data to the wireless communication hub device 112a. At block 3204 the wireless communication hub device 112a may receive the electronic medical and fitness device data, and at block 3206 may store the electronic medical and fitness device data. At block 3208 the wireless communication hub device 112 may transmit the electronic medical and fitness device data to the service platform server 140. At block 3212 the service platform server 140 may store the electronic medical and fitness device data. At block 3214 the electronic medical and fitness device 102e may transmit a request for electronic medical and fitness device data. In an embodiment the request may identify the originating electronic medical and fitness device, a time period, quantity, etc. At block 3216 the wireless communication hub device 112b may receive the request. At block 3218 the wireless communication hub device 112b may transmit the request to the service platform server 140. At block 3220 the service platform server may receive the request. In an embodiment, the service platform server 140 may retrieve the requested electronic medical and fitness device from a memory. At block 3222 the service platform server 140 may transmit the electronic medical and fitness device data to the wireless communication hub device 112b. At block 3224 the wireless communication hub device 112b may receive the electronic medical and fitness device data. At block 3226 the wireless communication hub device 112b may transmit the electronic medical and fitness device data to the electronic medical and fitness device 102e. At block 3228 the electronic medical and fitness device 102e may receive the electronic medical and fitness device data.

Figure 12:
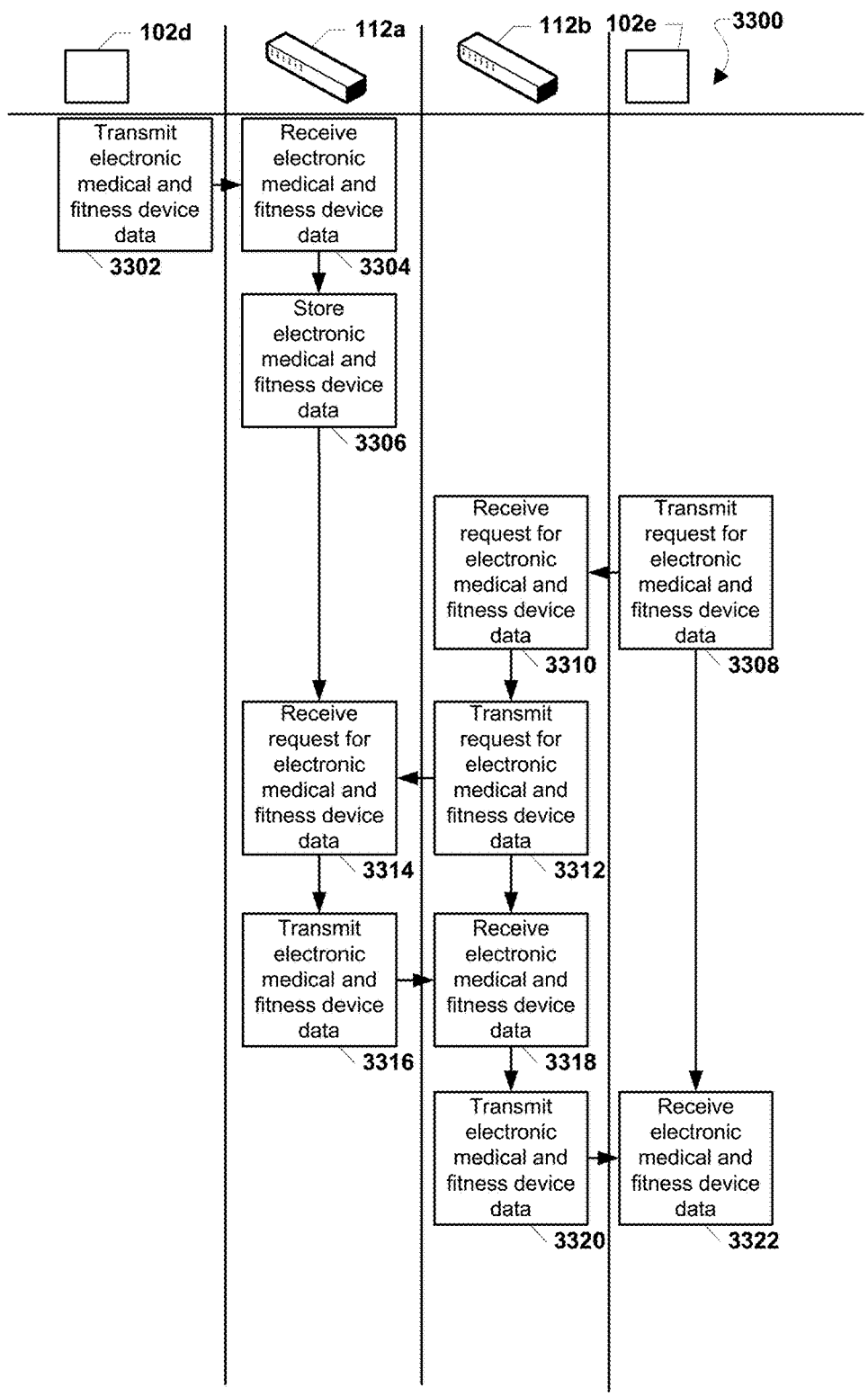
FIG. 12 is a process flow diagram illustrating another embodiment method for interconnected wireless communication hub device communication.

FIG. 12 illustrates an embodiment method 3300 enabling multi-wireless communication hub device 112a, 112b multi-electronic medical and fitness device 102d, 102e data sharing without data sharing communications to a service platform server. In method 3300 the respective electronic medical and fitness devices 102d, 102e, may have previously established communication pathways with their respective wireless communication hub devices 112a, 112b. Additionally, the respective wireless communication hub devices 112a, 112b may have previously established a communication pathway with each other. At block 3302 electronic medical and fitness device 102d may transmit electronic medical and fitness device data to the wireless communication hub device 112a. At block 3304 the wireless communication hub device 112a may receive the electronic medical and fitness device data, and at block 3306 may store the electronic medical and fitness device data. At block 3308 the electronic medical and fitness device 102e may transmit a request for electronic medical and fitness device data. In an embodiment the request may identify the originating electronic medical and fitness device, a time period, quantity, etc. At block 3310 the wireless communication hub device 112b may receive the request. At block 3310 the wireless communication hub device 112b may transmit the request to wireless communication hub device 112a. At block 3312 the wireless communication hub device 112a may receive the request. In an embodiment, the wireless communication hub device 112a may retrieve the requested electronic medical and fitness device from a memory. At block 3316 the wireless communication hub device 112a may transmit the electronic medical and fitness device data to the wireless communication hub device 112b. At block 3318 the wireless communication hub device 112b may receive the electronic medical and fitness device data. At block 3320 the wireless communication hub device 112b may transmit the electronic medical and fitness device data to the electronic medical and fitness device 102e. At block 3322 the electronic medical and fitness device 102e may receive the electronic medical and fitness device data.

Figure 13:
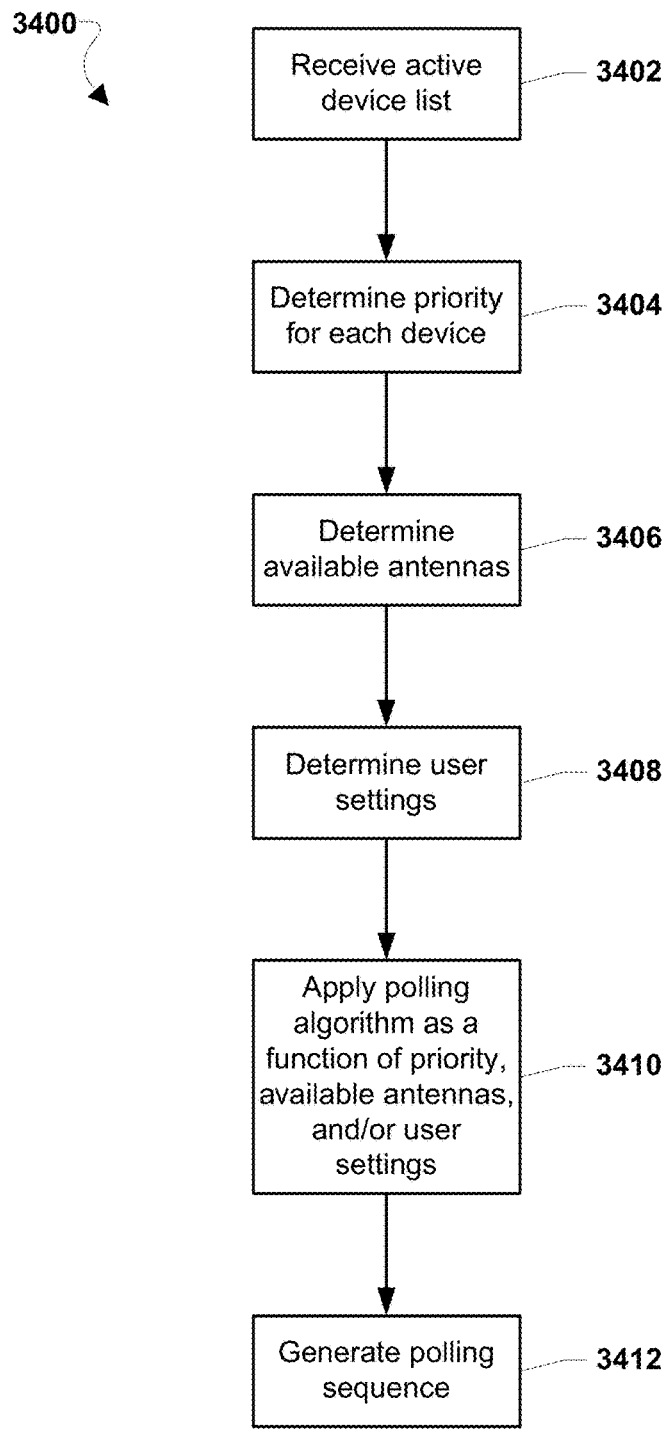
FIG. 13 is a process flow diagram illustrating an embodiment method for generating a polling sequence.

FIG. 13 illustrates an embodiment method 3400 for managing device polling by a wireless communication hub device. In an embodiment the method 3400 may be implemented by a service platform server and the polling sequence may be provided to a wireless communication hub device. At block 3402 the service process server may receive an active device list. In an embodiment, an active device list may be a list of all active electronic medical and fitness devices paired with a wireless communication hub device. At block 3404 the service process server may determine the priority for each device. In an embodiment, device priority may be determined based on the device type (e.g., heart rate monitors may be given a higher priority and weight scales may be given a lower priority) and/or sampled data importance (e.g., glucose meter for a diabetic may be given the highest priority). Also, device priority may be specified by a user, by the service platform server, or a third party (e.g., a physician) accessing the service platform server. At block 3406 the service platform server may determine the available antennas on the wireless communication hub device and/or the active devices. At block 3408, the service platform server may determine the user settings related to device polling. As an example, user settings may include user priority settings for devices, user antenna restrictions, user settings related to cost of transmission (e.g., power saving settings and/or money saving settings), preset polling algorithm selections, etc. At block 3410 a polling algorithm may be applied as a function of priority, available antennas, and/or user settings. Based on the applied polling algorithm, at block 3412 a polling sequence may be generated. In an embodiment, the service platform server may transmit the polling sequence to the wireless communication hub device for execution. In an alternative embodiment, the method 3400 may be implemented locally by a wireless communication hub device.

In an embodiment, the wireless communication hub device and an electronic medical and fitness device may be pre-paired before registration and use with the service platform server. Prior to bundling the wireless communication hub device and electronic medical and fitness device together to form a kit, the electronic medical and fitness device and the wireless communication hub device may be pre-paired. The pre-pairing registration may be performed over a short-range radio interface between the electronic medical and fitness device (e.g., a Bluetooth® connection). After pairing, each of the wireless communication hub device and the electronic medical and fitness device may be provided with each other's identity and may be paired if they're on and in radio-range proximity of each other. In an embodiment, a customer server may register the pairing on the customer side and may notify the service platform server of the pairing for storing in a repository and subsequent authentication request from the wireless communication hub device.

In an embodiment, a new wireless communication hub device may be provided to a user who already is operating an existing electronic medical and fitness device. The new wireless communication hub device retailer may determine from their records or from a customer server that the user is requesting the new wireless communication hub device is already utilizing the existing electronic medical and fitness device in their home and that the existing electronic medical and fitness device is capable of operating with the new wireless communication hub device. The retailer may register the pairing of the user's existing electronic medical and fitness device and the new wireless communication hub device at a customer server and the customer server may notify the service platform server of the pairing for storing in a repository and subsequent authentication request from the wireless communication hub device. The retailed may only ship the new wireless communication hub device (rather than a kit including an electronic medical and fitness device) to the user.

In an embodiment, a new electronic medical and fitness device not previously registered to a user may be registered with the service platform server, the wireless communication hub device, and/or a customer server. In an embodiment, a user may obtain a new electronic medical and fitness device from an indirect channel, such as not from a device/hub retailer or customer server operator. The user may need to resister the new electronic medical and fitness device to an existing wireless communication hub device. The user may contact the retailer/customer server operator by phone or web-portal to register the new electronic medical and fitness device. The retailer/customer server operator may register the new electronic medical and fitness device. The retailer/customer server operator may register the pairing of the new electronic medical and fitness device and the user's existing wireless communication hub device at the customer server. The customer server may notify the service platform server of the pairing for storing in a repository and subsequent authentication request from the wireless communication hub device.

In an embodiment, a new wireless communication hub device may be activated. The retailed/customer may register the new wireless communication hub device at the customer server. The customer server may notify the service platform server of the newly registered wireless communication hub device and provide the appropriate information to register and activate the new wireless communication hub device (e.g., the wireless communication hub device's serial number, SIM ID, number, etc).

In an embodiment, a wireless communication hub device may be deactivated. A retailer/customer server operator may determine that an existing wireless communication hub device in the field is not being used, or a user may request deactivation of the wireless communication hub device. The retailer/customer server operator may register the deactivation request with the customer server. The customer server will notify the service platform server of the deactivation. In an embodiment the service platform server may use an appropriate interface to a cellular operator to deactivate the wireless communication hub device, such as by deactivating the WWAN module. In an embodiment, notification of deactivation may be sent back to the customer server from the service platform server.

In an embodiment, a previously deactivated wireless communication hub device may be reactivated. A user of a previously deactivated wireless communication hub device may contact the retailer/customer server operator to request reactivation. The retailer/customer server operator may register a reactivation request with the customer server. The customer server may notify the service platform server of the reactivation request. The service platform server may perform appropriate interfaces with a cellular operator to reactivate the wireless communication hub device, such as reactivating the WWAN module. In an embodiment, notification of reactivation may be sent back to the customer server from the service platform server.

In an embodiment, a user may receive a kit containing a pre-paired wireless communication hub device and an electronic medical and fitness device. The user may open the kit and plug the wireless communication hub device into a wall-socket. The first time the wireless communication hub device powers on, the wireless communication hub device may perform self-tests and establish a data call on the cellular operator's network. The wireless communication hub device may then perform registration operations with the service platform server and exchange information with the service platform server. After receiving an acknowledgement from the service platform server the wireless M2M communications hub may be ready to perform other tasks.

In an embodiment, a wireless communication hub device may discover a USB radio dongle (e.g., ANT+) that connects to a USB port of the wireless communication hub device. The USB radio dongle may be authenticated and if successful and appropriate USB interface driver may be identified by the wireless communication hub device and used locally.

The radio dongle may now become an additional short-range radio on the wireless communication hub device and may communicate with any registered electronic medical and fitness device (e.g., ANT+ weight scale). In an embodiment, if registration is unsuccessful the radio dongle may be unusable.

In an embodiment, an electronic medical and fitness device may connect to the wireless communication hub device USB port. The wireless communication hub device may discover the electronic medical and fitness device is connected on the USB port. An appropriate USB interface driver may be identified and used locally. The USB electronic medical and fitness device may be authenticated and if successful may be used as described above with the wireless communication hub device locally.

In an embodiment, the wireless communication hub device may already be successfully registered with the service platform server and thru active search and/or listening may discover an electronic medical and fitness device in proximity. In an embodiment, the electronic medical and fitness device and the wireless communication hub device may have been pre-paired, and upon discovery the electronic medical and fitness device and the wireless communication hub device may immediately begin to communicate. In an alternative embodiment, some form of authentication of the electronic medical and fitness device may be performed by the wireless communication hub device prior to communication exchange and may be stored or sent to the service platform server. In a further embodiment, once communication with the electronic medical and fitness device is complete, the wireless communication hub device may check all other short-range radios to determine if there are other electronic medical and fitness devices that may want to communicate. In an embodiment if none are found the wireless communication hub device may come back to the first radio to start the communication session with the next electronic medical and fitness device.

In an embodiment, during electronic medical and fitness device discover the wireless communication hub device may receive pairing information from the electronic medical and fitness device. In an embodiment the wireless communication hub device may determine the electronic medical and fitness device is not on a local paired device list. The wireless communication hub device may send an electronic medical and fitness device authentication request to the service platform server. In an embodiment, the service platform server may have stored the pairing details for the electronic medical and fitness device previously received from the customer server. If the electronic medical and fitness device pairing details are stored it may send a "successful" message to the wireless communication hub device and the electronic medical and fitness device may be added to the local paired device list. If the electronic medical and fitness device pairing details are not stored on the service platform server the service platform server may send an "unsuccessful" message to the wireless communication hub device and the electronic medical and fitness device may be denied service by the wireless communication hub device.

In an embodiment, a user may be operating two wireless communication hub devices in their home, and two electronic medical and fitness devices received with each of the respective wireless communication hub devices. Each electronic medical and fitness device may be newly paired with the other wireless communication hub device as if it were a new electronic medical and fitness device as described above.

In an embodiment, communications between various electronic medical and fitness devices and the wireless communication hub device thru various radio links and USB connections may be managed by the wireless communication hub device either concurrently, in some sequential round robin, in hybrid, or other fashion.

In an embodiment, the wireless communication hub device may store electronic medical device data. The wireless communication hub device may receive a data payload containing payload data from each electronic medical and fitness device it is communicating with when a measurement on a respective electronic medical and fitness device is taken and may store the payload data locally. Utilizing some threshold and/or timer approach, the wireless communication hub device may then upload the data payload to the service platform server.

In an embodiment, the wireless communication hub device may periodically receive notifications form the service platform server over a data call (e.g., TCP/IP) and may respond accordingly. In an embodiment, the wireless communication hub device may periodically receive notification from the service platform server via a mobile terminated (MT) short message service (SMS) message. In an embodiment, to the wireless communication hub device's immediate attention, the service platform server may send a MT SMS to the wireless communication hub device for various reasons (such as to run a diagnostic check, for a pairing update, firmware/software OTA update, security check, authentication, re-authentication, other commands, a persistent data connection failure, and/or communication threshold expiration, etc). In an embodiment, in response to the MT SMS, the wireless communication hub device may immediately wake up and establish a data call with the service platform server, and process next operations as directed by the service platform server.

In an optional embodiment, the wireless communication hub device may periodically go into a low power mode. In an embodiment, the wireless M2M communication mode may not maintain a data call actively with the service platform server to conserve resources, but may periodically set up a data call with the service platform server, such as on an ad-hoc basis (e.g., stored data needs to be uploaded), on an exception basis (e.g., when receiving an SMS message), and/or on a hybrid combination of approaches.

In an embodiment, the wireless communication hub device may receive a notification to upgrade firmware/software. In an embodiment, the wireless communication hub device may establish a data call (e.g., TCP/IP) with the service platform server and the service platform server may push the upgrade build file(s) to the wireless communication hub device. In an embodiment, the wireless communication hub device may receive the upgrade build file(s) and management software on the wireless communication hub device may update the new build.

In an embodiment, an electronic medical and fitness device may utilize the wireless communication hub device to access data from other electronic medical and fitness devices currently, or previously, connected to the wireless communication hub device, or to other wireless communication hub devices (located in the same geographic location or elsewhere). In an embodiment, the other electronic medical and fitness devices may be owned/operated by the same user or may be owned/operated by different users. In an embodiment, the wireless M2M hub may have access to all shareable data on the wireless communication hub device, get data from the service platform server, request data from the service platform server stored on other wireless communication hub devices, and/or a hybrid combination of all approaches. In an embodiment, sharing and business agreements may control data shareability/availability.

In an embodiment, multiple users in a household may utilize the same electronic medical and fitness device (e.g., a weight scale, blood pressure monitor, etc.). In an embodiment, a determination as to the user currently utilizing the electronic medical and fitness device may be made. In an embodiment, the electronic medical and fitness device may determine the identity of the user. In an embodiment, user identification data may be included in the data sent from the electronic medical and fitness device to the wireless communication hub device.

In an embodiment, the wireless communication hub device may not include a battery backup, in this manner removing the wireless communication hub device from a power source (e.g., unplugging from the wall, power outage, etc) may result in all data stored on the wireless communication hub device being lost.

In an embodiment, the service platform server may store data received from an electronic medical and fitness device via a wireless communication hub device (e.g., store data payloads in an online transaction processing (OLTP) database and may upline the data (e.g., to a customer server over a web services API) based on registration (e.g., device, hub, and/or customer/user).

In an embodiment, the service platform server may receive single (and/or batch) events, commands, and/or messages from a customer server (or multiple customer servers) and forward them to an electronic medical and fitness device via a wireless communication hub device. In an embodiment, the wireless communication hub device may send a receipt acknowledgement to the service platform server may which may forward the receipt acknowledgement to the customer server that originated the event, command, and/or message. In an embodiment, if multiple events, commands, and/or messages are intended for a wireless communication hub device they may be batched to the wireless communication hub device.

In an embodiment, the service platform server may be enabled to direct wireless communication hub device diagnostic troubleshooting. In an embodiment, the troubleshooting may be accomplished remotely from the service platform server over a data call established between the service platform server and the wireless communication hub device. In an alternative embodiment, a diagnostic tool may be connected to the wireless communication hub device's USB port to enable diagnostic troubleshooting. In an embodiment, the service platform server may perform remote diagnostics to determine and/or resolve data connectivity issues with the wireless communication hub device. In an embodiment, resolution of data connectivity issues may involve the cellular operator interface and/or the wireless communication hub device operator/user interface. In an embodiment, if WWAN coverage is lost or coverage is spotty the service platform server may field the associated customer service request and resolution of the issues may involve the cellular operator interface and/or the wireless communication hub device operator/user interface.

In an embodiment, the wireless communication hub device may encapsulate device data files in a manner such that the encapsulated device data files tunnel through the gateway in a different protocol than they are received in the gateway.

Figure 14:
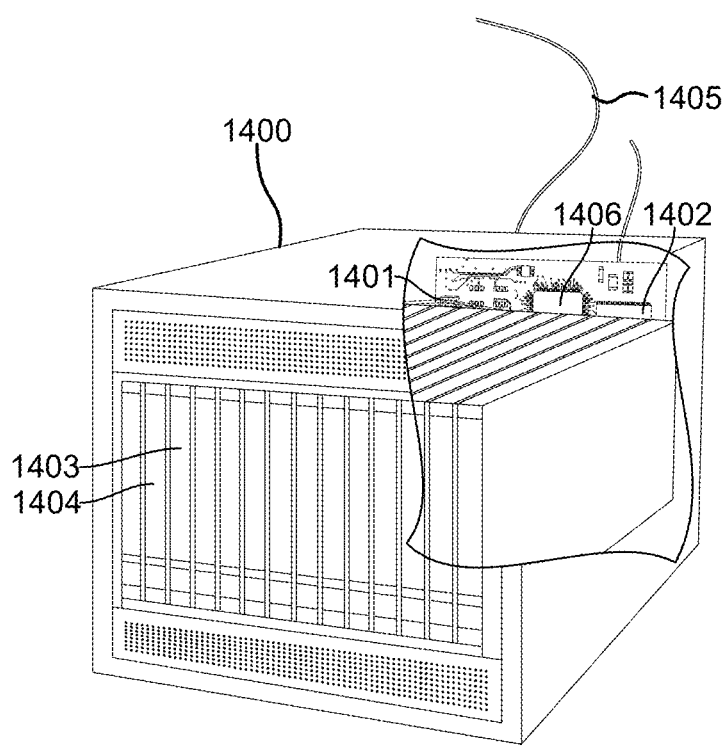
FIG. 14 is a component block diagram of a server suitable for use with various embodiments.

The embodiments described above may be implemented with any of a variety of server devices, such as the server 1400 illustrated in FIG. 14. Such a server 1400 typically includes a processor 1401 coupled to volatile memory 1402 and a large capacity nonvolatile memory, such as a disk drive 1403. The server 1400 may also include a floppy disc drive and/or a compact disc (CD) drive 1406 coupled to the processor 1401. The server 1400 may also include network access ports 1404 coupled to the processor 1401 for establishing data connections with network circuits 1405, such as the Internet.

Figure 15:
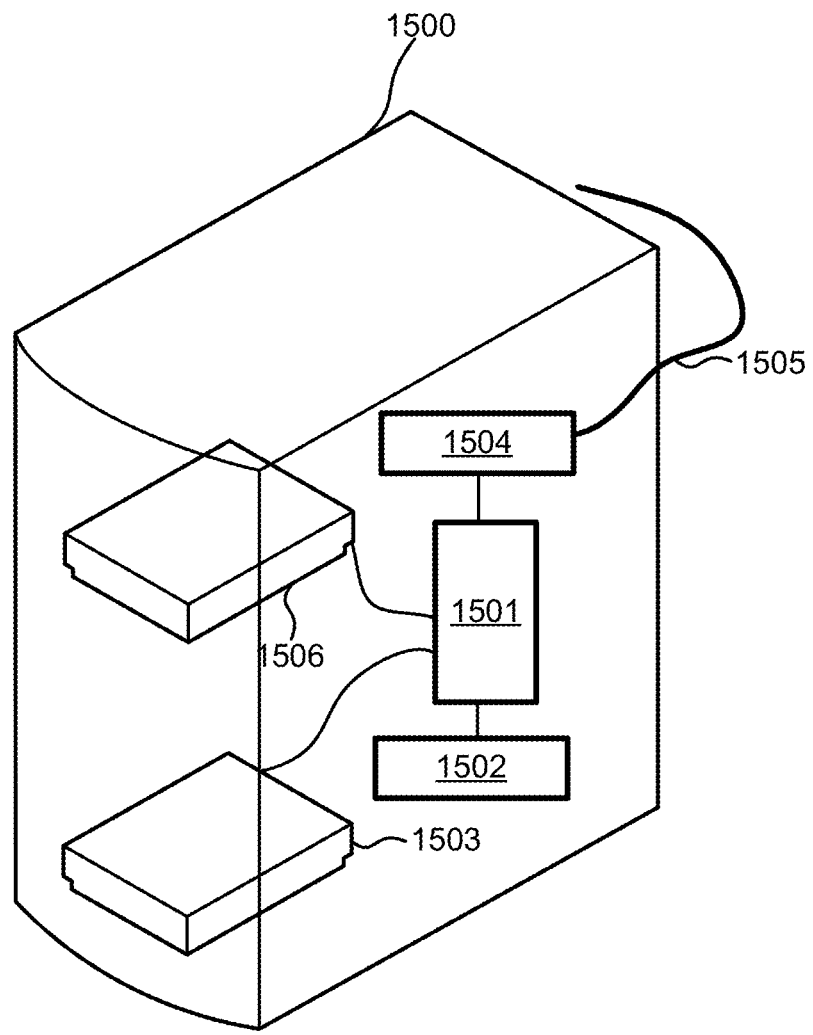
FIG. 15 is a component block diagram of another server suitable for use with the various embodiments.

The embodiments described above may be implemented with any of a variety of server devices, such as the server 1500 illustrated in FIG. 15. Such a server 1500 typically includes a processor 1501 coupled to volatile memory 1502 and a large capacity nonvolatile memory, such as a disk drive 1503. The server 1500 may also include a floppy disc drive and/or a compact disc (CD) drive 1506 coupled to the processor 1501. The server 1500 may also include network access ports 1504 coupled to the processor 1501 for establishing data connections with network circuits 1505, such as the Internet.

Figure 16:
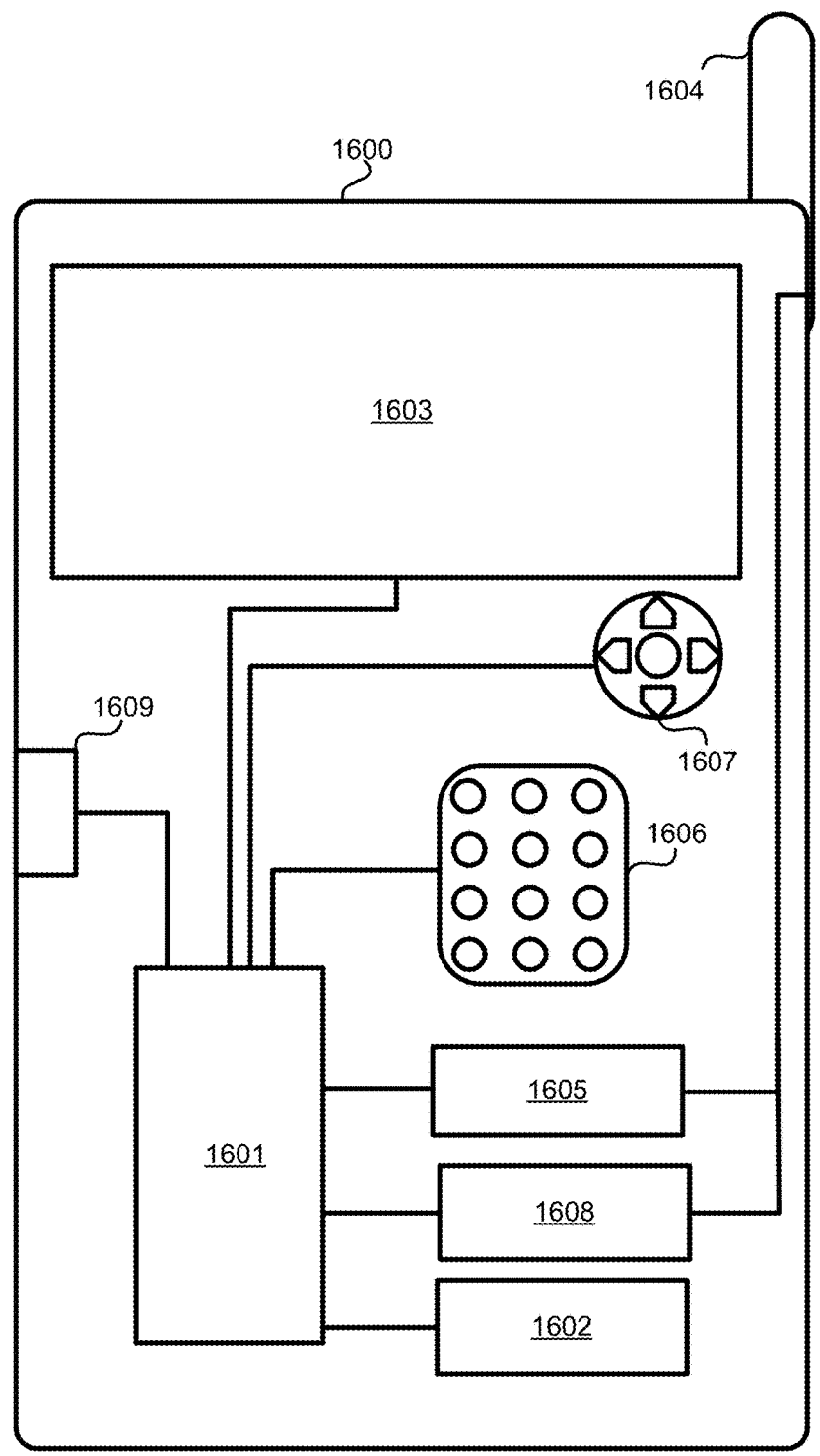
FIG. 16 is a component block diagram of a mobile device suitable for use with the various embodiments.

The embodiments may also be implemented on any of a variety of mobile devices, an example of which is illustrated in FIG. 16. For example, an exemplary mobile receiver device 1600 may include a processor 1601 coupled to internal memory 1602, a display 1603, and to a network access port 1609 (e.g., a USB port). Additionally, the mobile receiver device 1600 may have an antenna 1604 for sending and receiving electromagnetic radiation that is connected to a wireless data link and/or cellular telephone transceiver 1605 and to a local area wireless transceiver 1608, both coupled to the processor 1601. Mobile receiver devices typically also include a key pad 1606 or miniature keyboard and menu selection buttons or rocker switches 1607 for receiving user inputs.

The processors 301, 1401, 1501, 1601 in the various devices may be any programmable microprocessor, microcomputer or multiple processor chip or chips that can be configured by software instructions (applications) to perform a variety of functions, including the functions of the various embodiments described herein. In some devices, multiple processors 301, 1401, 1501, 1601 may be provided, such as one processor dedicated to wireless communication functions and one processor dedicated to running other applications. Typically, software applications may be stored in the internal memory 301, 1401, 1501, 1601 before they are accessed and loaded into the processor 301, 1401. In some mobile devices, the processor 301, 1401, 1501, 1601 may include internal memory sufficient to store the application software instructions. In some devices, the secure memory may be in a separate memory chip coupled to the processor 301, 1401, 1501, 1601. In many devices the internal memory 302, 1402, 1502, 1602 may be a volatile or nonvolatile memory, such as flash memory, or a mixture of both. For the purposes of this description, a general reference to memory refers to all memory accessible by the processor 301, 1401, 1501, 1601, including internal memory 302, 1402, 1502, 1602 removable memory plugged into the device, and memory within the processor 301, 1401, 1501, 1601 itself.

Further details regarding the various embodiments are provided in the drawings that are included in the drawings but not described above, and in the technical specifications which are attached hereto as Attachment A. Attachment A and all drawings of this application, including those not discussed above are part of this provisional application.

The foregoing method descriptions and the process flow diagrams are provided merely as illustrative examples and are not intended to require or imply that the steps of the various embodiments must be performed in the order presented. As will be appreciated by one of skill in the art the order of steps in the foregoing embodiments may be performed in any order. Words such as "thereafter," "then," "next," etc. are not intended to limit the order of the steps; these words are simply used to guide the reader through the description of the methods. Further, any reference to claim elements in the singular, for example, using the articles "a," "an" or "the" is not to be construed as limiting the element to the singular.

The various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

The hardware used to implement the various illustrative logics, logical blocks, modules, and circuits described in connection with the aspects disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but, in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration. Alternatively, some steps or methods may be performed by circuitry that is specific to a given function.

In one or more exemplary aspects, the functions described may be implemented in hardware, software, firmware, or any combination thereof. If implemented in software, the functions may be stored on or transmitted over as one or more instructions or code on a computer-readable medium. The steps of a method or algorithm disclosed herein may be embodied in a processor-executable software module executed which may reside on a non-transitory, tangible computer-readable storage medium. Non-transitory computer-readable media include any available computer storage media that may be accessed by a computer. By way of example, and not limitation, such non-transitory computer-readable media may comprise RAM, ROM, EEPROM, CD-ROM or other optical disk storage, magnetic disk storage or other magnetic storage devices, or any other medium that may be used to carry or store desired program code in the form of instructions or data structures and that may be accessed by a computer. Disk and disc, as used herein, includes compact disc (CD), laser disc, optical disc, digital versatile disc (DVD), floppy disk, and blu-ray disc where disks usually reproduce data magnetically, while discs reproduce data optically with lasers. Combinations of the above should also be included within the scope of computer-readable media. Additionally, the operations of a method or algorithm may reside as one or any combination or set of codes and/or instructions on a non-transitory processor-readable medium and/or non-transitory computer-readable medium, which may be incorporated into a computer program product.

The preceding description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the following claims and the principles and novel features disclosed herein.

What is claimed is:

1. A method for providing access to an electronic medical or fitness device, comprising:
    establishing a first wireless communications link between a communication hub device and a remote server based on registration operations performed by the communication hub device in response to the communication hub device powering on, wherein the registration operations performed by the communication hub device are performed automatically and without user interaction;
    discovering an electronic medical or fitness device which can be coupled to the communication hub device;
    determining whether an identifier of the discovered electronic medical or fitness device is listed on a local paired device list;
    establishing a second wireless communications link between the communication hub device and the discovered electronic medical or fitness device in response to determining that the identifier of the discovered electronic medical or fitness device is listed on the local paired device list;
    transmitting the identifier of the discovered electronic medical or fitness device to the remote server in response to determining that the identifier of the discovered electronic medical or fitness device is not listed on the local paired device list;
    receiving, from the remote server, both a unique internet protocol address for the discovered electronic medical or fitness device assigned by the remote server prior to the transmission of the identifier and a device authorization message at the communication hub device authorizing communication with the discovered electronic medical or fitness device when the identifier of the discovered electronic medical or fitness device is included in a listing of authorized electronic medical or fitness devices maintained in the remote server; and
    establishing the second wireless communications link between the communication hub device and the discovered electronic medical or fitness device in response to receiving the device authorization message.

2. The method of claim 1, wherein the listing of authorized electronic medical or fitness devices maintained in the remote server lists one or more medical or fitness device pre-paired with the communication hub device prior to delivery of the communication hub device to a user.

3. The method of claim 1, wherein the local paired device list is generated at the communication hub device based on a pairing of the discovered electronic medical or fitness device and the communication hub device that occurred prior to delivery of the communication hub device to a user.

4. The method of claim 3, wherein the communication hub device automatically and without user interaction establishes the first wireless communications link, discovers the electronic medical or fitness device, transmits the identifier of the discovered electronic medical or fitness device, receives the device authorization message, determines whether the identifier of the discovered electronic medical or fitness device is listed on the local paired device list, and establishes the second wireless communications link.

5. A communication hub device, comprising:
a processor, wherein the processor is configured with processor-executable instructions to perform operations to:
establish a first wireless communications link with a remote server based on registration operations performed in response to the communication hub device powering on, wherein the registration operations performed by the communication hub device are performed automatically and without user interaction;
discover an electronic medical or fitness device which can be coupled to the communication hub device;
determine whether an identifier of the discovered electronic medical or fitness device is listed on a local paired device list;
establish a second wireless communications link with the discovered electronic medical or fitness device in response to determining that the identifier of the discovered electronic medical or fitness device is listed on the local paired device list;
transmit the identifier of the discovered electronic medical or fitness device to the remote server in response to determining that the identifier of the discovered electronic medical or fitness device is not listed on the local paired device list;
receive, from the remote server, both a unique internet protocol address for the discovered electronic medical or fitness device assigned by the remote server prior to the transmission of the identifier and a device authorization message authorizing communication with the discovered electronic medical or fitness device when the identifier of the discovered electronic medical or fitness device is included in a listing of authorized electronic medical or fitness devices maintained in the remote server; and
establish the second wireless communications link with the discovered electronic medical or fitness device in response to receiving the device authorization message.

6. The communication hub device of claim 5, wherein the listing of authorized electronic medical or fitness devices maintained in the remote server lists one or more medical or fitness device pre-paired with the communication hub device prior to delivery of the communication hub device to a user.

7. The communication hub device 5, wherein the local paired device list is generated at the communication hub device based on a pairing of the discovered electronic medical or fitness device and the communication hub device that occurred prior to delivery of the communication hub device to a user.

8. The communication hub device of claim 7, wherein the processor is configured with processor-executable instructions to perform operations to automatically without user interaction establish the first wireless communications link, discover the electronic medical or fitness device, transmit the identifier of the discovered electronic medical or fitness device, receive the device authorization message, determine whether the identifier of the discovered electronic medical or fitness device is listed on the local paired device list, and establish the second wireless communications link.

9. A non-transitory processor readable medium having stored thereon processor-executable instructions configured to cause a processor of a communication hub device to perform operations comprising
establishing a first wireless communications link with a remote server based on registration operations performed by the communication hub device automatically and without user interaction in response to the communication hub device powering on;
discovering an electronic medical or fitness device which can be coupled to the communication hub device;
determining whether an identifier of the discovered electronic medical or fitness device is listed on a local paired device list; and
establishing a second wireless communications link with the discovered electronic medical or fitness device in response to determining that the identifier of the discovered electronic medical or fitness device is listed on the local paired device list;
transmitting the identifier of the discovered electronic medical or fitness device to the remote server in response to determining that the identifier of the discovered electronic medical or fitness device is not listed on the local paired device list;
receiving, from the remote server, both a unique internet protocol address for the discovered electronic medical or fitness device assigned by the remote server prior to the transmission of the identifier and a device authorization message authorizing communication with the discovered electronic medical or fitness device when the identifier of the discovered electronic medical or fitness device is included in a listing of authorized electronic medical or fitness devices maintained in the remote server; and
establishing the second wireless communications link with the discovered electronic medical or fitness device in response to receiving the device authorization message.

10. The non-transitory processor readable medium of claim 9, wherein the listing of authorized electronic medical or fitness devices maintained in the remote server lists one or more medical or fitness device pre-paired with the communication hub device prior to delivery of the communication hub device to a user.

11. The non-transitory processor readable medium of claim 9, wherein the stored processor-executable instructions are configured to cause a processor of a communication hub device to perform operations such that the local paired device list is generated at the communication hub device based on a pairing of the discovered electronic medical or fitness device and the communication hub device that occurred prior to delivery of the communication hub device to a user.

12. The non-transitory processor readable medium of claim 11, wherein the stored processor-executable instructions are configured to cause a processor of a communication hub device to perform operations such that the communication hub device automatically and without user interaction establishes the first wireless communications link, discovers the electronic medical or fitness device, transmits the identifier of the discovered electronic medical or fitness device, receives the device authorization message, determines whether the identifier of the discovered electronic medical or fitness device is listed on the local paired device list, and establishes the second wireless communications link.

13. A communication hub device, comprising:
  means for establishing a first wireless communications link with a remote server based on registration operations performed in response to the communication hub device powering on, wherein the registration operations performed by the communication hub device are performed automatically and without user interaction;
  means for discovering an electronic medical or fitness device which can be coupled to the communication hub device;
  means for determining whether an identifier of the discovered electronic medical or fitness device is listed on a local paired device list; and
  means for establishing a second wireless communications link between the communication hub device and the discovered electronic medical or fitness device in response to determining that the identifier of the discovered electronic medical or fitness device is listed on the local paired device list;
  means for transmitting the identifier of the discovered electronic medical or fitness device to the remote server in response to determining that the identifier of the discovered electronic medical or fitness device is not listed on the local paired device list;
  means for receiving, from the remote server, both a unique internet protocol address for the discovered electronic medical or fitness device assigned by the remote server prior to the transmission of the identifier and a device authorization message authorizing communication with the discovered electronic medical or fitness device when the identifier of the discovered electronic medical or fitness device is included in a listing of authorized electronic medical or fitness devices maintained in the remote server; and
  means for establishing the second wireless communications link with the discovered electronic medical or fitness device in response to receiving the device authorization message.

14. The communication hub device of claim 13, wherein the listing of authorized electronic medical or fitness devices maintained in the remote server lists one or more medical or fitness device pre-paired with the communication hub device prior to delivery of the communication hub device to a user.

15. The communication hub device of claim 13, wherein the local paired device list is generated at the communication hub device based on a pairing of the discovered electronic medical or fitness device and the communication hub device that occurred prior to delivery of the communication hub device to a user.

16. The communication hub device of claim 15, wherein the communication hub device automatically and without user interaction establishes the first wireless communications link, discovers the electronic medical or fitness device, transmits the identifier of the discovered electronic medical or fitness device, receives the device authorization message, determines whether the identifier of the discovered electronic medical or fitness device is listed on the local paired device list, and establishes the second wireless communications link.

* * * * *